US008349831B2

(12) United States Patent
Coulter et al.

(10) Patent No.: US 8,349,831 B2
(45) Date of Patent: Jan. 8, 2013

(54) CALCIUM RECEPTOR MODULATING AGENTS

(75) Inventors: Thomas S. Coulter, Wantage (GB);
Adam James Davenport, Didcot (GB);
Christopher H. Fotsch, Thousand Oaks, CA (US); Chiara Ghiron, Siena (IT);
Paul E. Harrington, Camarillo, CA (US); Michael Gerard Kelly, Thousand Oaks, CA (US); Steve Fong Poon, South Pasadena, CA (US); Andrew Tasker, Simi Valley, CA (US); Ning Xi, Thousand Oaks, CA (US); Qing Ping Zeng, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 1017 days.

(21) Appl. No.: 11/977,777

(22) Filed: Oct. 25, 2007

(65) Prior Publication Data
US 2008/0221101 A1   Sep. 11, 2008

Related U.S. Application Data

(60) Provisional application No. 60/854,909, filed on Oct. 26, 2006.

(51) Int. Cl.
| A61K 31/5377 | (2006.01) |
| A61K 31/137 | (2006.01) |
| C07C 211/29 | (2006.01) |
| A61P 13/12 | (2006.01) |
| A61P 9/00 | (2006.01) |
| C07D 401/04 | (2006.01) |

(52) U.S. Cl. ............... 514/235.5; 514/655; 544/131; 564/336

(58) Field of Classification Search .................. None
See application file for complete search history.

(56) References Cited

U.S. PATENT DOCUMENTS

| 6,011,068 A | 1/2000 | Nemeth et al. |
| 6,031,003 A | 2/2000 | Nemeth et al. |
| 6,211,244 B1 | 4/2001 | Van Wagenen et al. |
| 6,313,146 B1 | 11/2001 | Van Wagenen et al. |
| 6,403,832 B1 | 6/2002 | Oikawa et al. |
| 6,407,111 B1 | 6/2002 | Bös et al. |
| 6,414,002 B1 | 7/2002 | Cheng et al. |
| 6,436,152 B1 | 8/2002 | Chassot et al. |
| 6,894,190 B2 | 5/2005 | Oikawa et al. |
| 6,908,935 B2 | 6/2005 | Kelly et al. |
| 7,084,167 B2 | 8/2006 | Ruat et al. |
| 7,157,498 B2 | 1/2007 | Dauban et al. |
| 2007/0225296 A1 | 9/2007 | Miyazaki et al. |

FOREIGN PATENT DOCUMENTS

| EP | 1074539 | 2/2001 |
| EP | 01882684 | 1/2008 |
| JP | 2002030050 | 1/2002 |
| WO | WO-02/059080 | * 8/2002 |
| WO | WO 03/099776 | 12/2003 |
| WO | WO 2004/030669 | 4/2004 |
| WO | WO 2008/035381 | 3/2008 |

OTHER PUBLICATIONS

Didiuk et al., Bioorg Med Chem Lett, 2009, 19, 4555-4559.*
Weinberg et al., caplus an 2009:887863.*
Brown, Edward M., et al., "Neomycin Mimics the Effects of High Extracellular Calcium Concentrations on Parathyroid Function in Dispersed Bovine Parathyroid Cells," *Endocrinology*, vol. 128, No. 6, 3047-3054, 1991.
Chen, Chu J. and Brown, Edward M., "The Diltiazem Analog TA-3090 Mimics the Actions of High Extracellular $Ca^{2+}$ on Parathyroid Function in Dispersed Bovine Parathyroid Cells," *Journal of Bone and Mineral Research*, vol. 5, No. 6, 581-587, 1990.
Dauban, Philippe, et al., "$N^1$-Arylsulfonyl-$N^2$-(1-aryl)ethyl-3-phenylpropane-1,2-diamines as Novel Calcimimetics Acting on the Calcium Sensing Receptor," *Biorg. Med. Chem. Lett.* 10, 2001-2004, 2000.
Garrett, James E., et al., "Calcitonin-Secreting Cells of the Thyroid Express an Extracellular Calcium Receptor Gene," *Endocrinology*, vol. 136, No. 11, 5202-5211, 1995.
Garrett, James E., et al., "Molecular Cloning and Functional Expression of Human Parathyroid Calcium Receptor cDNAs," *Journal of Biological Chemistry*, vol. 270, No. 21, 12919-12925, 1995.
Nemeth, E.F., "Regulation of Cytosolic Calcium by Extracellular Divalent Cations in C-cells and Parathyroid Cells," *Cell Calcium*, vol. 11, 323-327, 1990.
Nemeth, Edward F., et al., "Calcimimetics with Potent and Selective Activity on the Parathyroid Calcium Receptor," *Pharmacology*, vol. 95, 4040-4045, Mar. 1998. Svensson, Leif A., and Tunek, Anders, "The Design and Bioactivation of Presystematically Stable Prodrugs," *Drug Metabolism Reviews*, 19(2), 165-194, 1988.
Zaidi, Mone, et al., "Intracellular Calcium in the Control of Osteoclast Function," *Biochemical and Biophysical Research Communications*, vol. 167, No. 2, 807-812 Mar. 16, 1990.
Zaidi, Mone, "Calcium Receptors" on Eukaryotic Cells with Special Reference to the Osteoclast, *Bioscience Reports*, vol. 10, No. 6, 493-507, 1990.

* cited by examiner

*Primary Examiner* — Sun Jae Loewe
(74) *Attorney, Agent, or Firm* — Olga Mekhovich

(57) ABSTRACT

The present invention relates generally to compounds represented in Formula I, pharmaceutical compositions comprising them and methods of treating of diseases or disorders related to the function of the calcium sensing receptor. The invention also relates to processes for making such compounds and to intermediates useful in these processes.

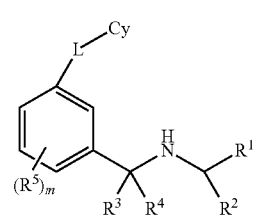

10 Claims, No Drawings

CALCIUM RECEPTOR MODULATING AGENTS

CROSS-REFERENCE

This application claims the benefit of priority of U.S. Provisional Patent Application No. 60/854,909, which was filed on Oct. 26, 2006.

FIELD OF THE INVENTION

This invention relates generally to the field of medicine and, more specifically, to calcium receptor modulating compounds and pharmaceutical compositions comprising them.

BACKGROUND OF THE INVENTION

Extracellular calcium ion concentration is involved in a variety of biological processes, such as blood clotting, nerve and muscle excitability and bone formation (Cell Calcium 11:319, 1990). One of the key elements of this regulation is the calcium receptor known as the Ca sensing receptor or CaSR. Calcium ion receptors, which are present on the membranes of various cells in the body, such as parathyroid and kidney cells (Nature 366:574, 1993; J. Bone Miner. Res. 9, Supple. 1, s282, 1994; J. Bone Miner. Res. 9, Supple. 1, s409, 1994; Endocrinology 136:5202, 1995), are important to the regulation of the extracellular calcium ion concentration. For example, concentration of extracellular calcium ion regulates the bone resorption by osteoclasts (Bioscience Reports 10:493, 1990), secretion of parathyroid hormone (PTH) from parathyroid cells and secretion of calcitonin from C-cells (Cell Calcium 11:323, 1990). Parathyroid cells thus have at their surface the calcium sensing receptor (CaSR), which detects changes in extracellular calcium concentration and initiates the functional response of this cell, which is a modulation of the secretion of the parathyroid hormone (PTH). Secretion of PTH increases extracellular calcium ion concentration by acting on various cells, such as bone and kidney cells, and the extracellular calcium ion concentration reciprocally inhibits the secretion of PTH by acting on parathyroid cells. The reciprocal relationship between calcium concentration and PTH level is an essential mechanism for calcium homeostasis maintenance.

The cloning of the calcium receptor by Brown in 1993 consequently demonstrated two possible signalling pathways for this G protein coupled receptor: one pathway by activation of the Gi protein (sensitive to the pertussis toxin) which stimulates phospholipase C and inhibits adenylate cyclase; the other pathway by activating the Gq protein responsible for mobilising intracellular calcium. These two signalling pathways, either independently of one another or together, can be activated so as to trigger the associated biological effect. On its extracellular portion, the calcium receptor is a low affinity receptor which is stimulated by millimolar concentrations of agonists, in particular the calcium ion $Ca^{2+}$. In addition, this receptor can also be activated by some divalent metals (magnesium) or trivalent metals (gadolinium, lanthanum, etc.) or else by polycationic compounds such as neomycin or spermine.

Several classes of calcimimetic compounds have been disclosed for regulating extracellular calcium ion concentration, particularly for reducing or inhibiting secretion of PTH. For example, U.S. Pat. Nos. 6,908,935, 6,011,068 and 5,981,599 disclose arylalkylamines that are calcium receptor active molecules. EP 933354; WO 0021910, WO 96/12697; WO 95/11221; WO 94/18959; WO 93/04373; Endocrinology 128:3047, 1991; Biochem. Biophys. Res. Commun. 167:807, 1990; J. Bone Miner. Res. 5:581, 1990; and Nemeth et al., "Calcium-binding Proteins in Health and Disease," Academic Press, Inc., pp. 33-35 (1987) disclose various agents that interact with calcium receptors.

Dauban et al., Bioorg. Med. Chem. Let. 10:2001-4, 2000, disclose various N1-arylsulfonyl-N2-(1-aryl)ethyl-3-phenyl-propane-1,2-diamine compounds as calcimimetics acting on the calcium sensing receptor.

Oikawa et al., in U.S. Pat. No. 6,403,832, and publication No. US2002/143212, describes aryl amine compounds useful as chiral intermediates in the synthesis of optically active propionic acid derivatives. Chassot et al., U.S. Pat. No. 6,436,152, describes arylalkylamine compounds useful as hair dye precursor compounds.

Bös et al., U.S. Pat. No. 6,407,111, describes phenyl substituted pyridine and benzene derivates that are antagonistic to the NK-1 receptor.

SUMMARY OF THE INVENTION

The present invention relates to selected calcimimetic compounds and pharmaceutically acceptable salts thereof. In one aspect, the invention compounds advantageously reduce or inhibit PTH secretion. Therefore, this invention also encompasses pharmaceutical compositions, methods for reducing or inhibiting PTH secretion and methods for treatment or prophylaxis of diseases associated with bone disorders, such as osteoporosis, or associated with excessive secretion of PTH, such as hyperparathyroidism. The subject invention also relates to processes for making such compounds as well as to intermediates useful in such processes.

The compounds of the invention are represented by the following general structure:

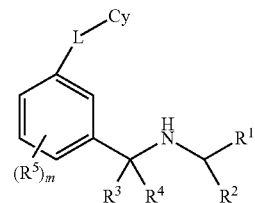

I or a stereoisomer, a tautomer, a solvate, a pharmaceutically acceptable salt, or a prodrug thereof, wherein the variables are defined in Detailed Description below. In one aspect, the invention provides compounds of Formula I, wherein $R^1$ is phenyl substituted by 0, 1, 2 or 3 substituents selected from $C_{1-6}$alkyl, halogen, $C_{1-4}$haloalkyl, —$OC_{1-6}$alkyl, cyano and nitro. In another aspect, $R^1$ can be naphthyl substituted by 0, 1, 2 or 3 substituents selected from $C_{1-6}$alkyl, halogen, $C_{1-4}$haloalkyl, —$OC_{1-6}$alkyl, cyano and nitro. In one aspect, $R^3$ can be H. In another aspect, $R^4$ can be H.

In one aspect, $R^5$ can be H or halogen. In one aspect, halogen can be Cl. In another aspect, $R^5$ can be methoxy. In a further aspect, $R^5$ can be substituted or unsubstituted piperidyl, wherein the substituents can be selected from halogen, —$OR^b$, —$NR^aR^d$, —$C(=O)OR^c$, —$C(=O)NR^aR^d$, —$OC(=O)R^c$, —$NR^aC(=O)R^c$, cyano, nitro, —$NR^aS(=O)_nR^c$ or —$S(=O)_nNR^aR^d$.

The invention provides compounds of Formula I, wherein L can be —$NR^aC(=O)$—. In one aspect, $R^a$ is H. The invention further provides compounds of Formula I, wherein L can be —$NR^aC(=O)OR^c$—. In one aspect, L can be —S—. In another aspect, L can be —NR$^d$C(=O)NR$^d$—. In one aspect, R$^d$ can be H. In another aspect, L can be S(=O)$_n$—. In a further aspect, L can be —NR$^d$C$_{1-6}$alkyl-.

The invention further provides compounds of Formula I, wherein Cy can be optionally substituted heterocyclyl. In one aspect, Cy can be aryl or heteroaryl. In one aspect, Cy can be optionally substituted phenyl. In one aspect, Cy can be optionally substituted pyridyl. In one aspect, Cy can be optionally substituted isoxazolyl, optionally substituted thiophenyl, optionally substituted imidazolyl, optionally substituted thiadiazolyl, optionally substituted pyrazolyl, optionally substituted furanyl, or optionally substituted oxadiazolyl.

In one aspect, the invention provides compounds, stereoisomers, tautomers, solvates, pharmaceutically acceptable salts, or prodrug thereof, wherein the compounds are selected from the group consisting of:

(R)—N-(2-Chloro-5-((1-(3-chlorophenyl)ethylamino)methyl)phenyl)-5-methylisoxazole-3-carboxamide;
N-(2-chloro-5-((((1R)-1-phenylethyl)amino)methyl)phenyl) acetamide;
N-(2-chloro-5-((((1R)-1-phenylethyl)amino)methyl)phenyl)-2-furancarboxamide;
N-(2-chloro-5-((((1R)-1-phenylethyl)amino)methyl)phenyl)-1,3-dimethyl-1H-pyrazole-5-carboxamide;
N-(2-chloro-5-((((1R)-1-phenylethyl)amino)methyl)phenyl)-3-phenylpropanamide,
2-chloro-N-(2-chloro-5-((((1R)-1-phenylethyl)amino)methyl)phenyl)acetamide;
N-(2-chloro-5-((((1R)-1-phenylethyl)amino)methyl)phenyl)-2,2-dimethylpropanamide;
N-(2-chloro-5-((((1R)-1-phenylethyl)amino)methyl)phenyl) benzamide;
N-(2-chloro-5-((((1R)-1-phenylethyl)amino)methyl)phenyl)-2-thiophenecarboxamide;
N-(2-chloro-5-((((1R)-1-phenylethyl)amino)methyl)phenyl)-5-isoxazolecarboxamide;
N-(2-chloro-5-((((1R)-1-phenylethyl)amino)methyl)phenyl)-5-methyl-3-isoxazolecarboxamide;
N-(2-chloro-5-((((1R)-1-phenylethyl)amino)methyl)phenyl)-2-pyridinecarboxamide;
N-(2-chloro-5-((((1R)-1-phenylethyl)amino)methyl)phenyl)-3-pyridinecarboxamide;
N-(2-chloro-5-((((1R)-1-phenylethyl)amino)methyl)phenyl)-4-pyridinecarboxamide; phenylmethyl (2-chloro-5-((((1R)-1-phenylethyl)amino)methyl)phenyl)carbamate;
N-(2-chloro-5-((((1R)-1-phenylethyl)amino)methyl)phenyl)-2,5-dimethyl-1,3-oxazole-4-carboxamide;
N-(2-chloro-5-((((1R)-1-phenylethyl)amino)methyl)phenyl)-4-methyl-1,2,3-thiadiazole-5-carboxamide;
N-(2-chloro-5-((((1R)-1-phenylethyl)amino)methyl)phenyl)-5-(2-methyl-1,3-thiazol-4-yl)-3-isoxazolecarboxamide;
N-(2-chloro-5-((((1R)-1-phenylethyl)amino)methyl)phenyl)-N'-phenylurea;
N-(2-chloro-5-((((1R)-1-phenylethyl)amino)methyl)phenyl)-1-(1,1-dimethylethyl)-5-methyl-1H-pyrazole-3-carboxamide;
N-(2-chloro-5-((((1R)-1-phenylethyl)amino)methyl)phenyl)-5-phenyl-3-isoxazolecarboxamide;
6-chloro-N-(2-chloro-5-((((1R)-1-phenylethyl)amino)methyl)phenyl)-3-pyridinecarboxamide;
N-(2-chloro-5-((((1R)-1-phenylethyl)amino)methyl)phenyl)-3-thiophenecarboxamide;
N-(2-chloro-5-((((1R)-1-phenylethyl)amino)methyl)phenyl)-5-(2-pyridinyl)-2-thiophenecarboxamide;
N-(2-chloro-5-((((1R)-1-phenylethyl)amino)methyl)phenyl)-5-phenyl-2-thiophenecarboxamide;
N-(2-chloro-5-((((1R)-1-(1-naphthalenyl)ethyl)amino)methyl)phenyl)-2-pyridinecarboxamide;
(R)—N-(4-Chloro-3-nitrobenzyl)-1-(3-chlorophenyl)ethanamine;
(R)—N-(4-Chloro-3-(phenylthio)benzyl)-1-(3-chlorophenyl)ethanamine;
(R)—N-(4-chloro-3-(phenylsulfonyl)benzyl)-1-(3-chlorophenyl)ethanamine;
(R)-2-Chloro-5-((1-(3-chlorophenyl)ethylamino)methyl)benzenesulfonamide;
(R)—N-(4-Methoxy-3-(morpholinosulfonyl)benzyl)-1-(3-chlorophenyl)ethanamine;
(R)—N-(4-chloro-3-(morpholinosulfonyl)benzyl)-1-(3-chlorophenyl)ethanamine;
(R)—N-(2-Chloro-5-((1-phenylethylamino)methyl)phenyl)-2-(pyrrolidin-1-yl)acetamide;
(R)—N-(2-chloro-5-((1-phenylethylamino)methyl)phenyl)-6-(dimethylamino)nicotinamide;
N-(2-chloro-5-((((1R)-1-phenylethyl)amino)methyl)phenyl)-6-(4-morpholinyl)-3-pyridinecarboxamide;
N-(2-chloro-5-((((1R)-1-phenylethyl)amino)methyl)phenyl)-6-(4-methyl-1-piperazinyl)-3-pyridinecarboxamide;
N-(2-chloro-5-((((1R)-1-phenylethyl)amino)methyl)phenyl)-6-((2-(dimethylamino) ethyl)amino)-3-pyridinecarboxamide;
N-(2-chloro-5-((((1R)-1-phenylethyl)amino)methyl)phenyl)-6-(methylamino)-3-pyridinecarboxamide;
N-(2-chloro-5-((((1R)-1-phenylethyl)amino)methyl)phenyl)-6-(phenylamino)-3-pyridinecarboxamide;
N-(2-chloro-5-((((1R)-1-phenylethyl)amino)methyl)phenyl)-6-((phenylmethyl)amino)-3-pyridinecarboxamide;
N-(2-chloro-5-((((1R)-1-phenylethyl)amino)methyl)phenyl)-6-((2-phenylethyl)amino)-3-pyridinecarboxamide;
(R)-1-(2-(5-methylisoxazole-3-carboxamido)-4-((1-phenylethylamino)methyl)phenyl)piperidine-4-carboxamide;
(R)-1-(2-Chloro-5-((1-phenylethylamino)methyl)phenyl)piperidine-4-carboxamide;
(R)-2-Chloro-5-((1-phenylethylamino)methyl)-N-(pyridin-2-ylmethyl)benzenamine;
(1R)—N-(3-(1H-Benzo[d]imidazol-1-yl)-4-chlorobenzyl)-1-phenylethanamine;
(1R)—N-(4-chloro-3-(1H-1,2,4-triazol-1-yl)benzyl)-1-phenylethanamine;
((1R)—N-(4-Chloro-3-((1-methylpiperidin-3-yl)methoxy)benzyl)-1-(3-chlorophenyl)ethanamine;
(R)-methyl 2-(2-chloro-5-((1-(3-chlorophenyl)ethylamino) methyl)phenoxy)acetate;
(R)—N-(3-((1,2,4-oxadiazol-3-yl)methoxy)-4-chlorobenzyl)-1-(3-chlorophenyl)ethanamine;
(R)—N-(4-chloro-3-((5-methylisoxazol-3-yl)methoxy)benzyl)-1-(3-chlorophenyl)ethanamine;
(R)—N-(4-chloro-3-((1-methyl-1H-imidazol-2-yl)methoxy)benzyl)-1-(3-chlorophenyl)ethanamine;
(R)—N-(3-((5-tert-butyl-1,2,4-oxadiazol-3-yl)methoxy)-4-chlorobenzyl)-1-(3-chlorophenyl)ethanamine;
(R)-methyl 2-((2-chloro-5-((1-(3-chlorophenyl)ethylamino) methyl)phenoxy)methyl)oxazole-4-carboxylate;
(R)—N-(4-chloro-3-(6-methylpyridazin-3-yloxy)benzyl)-1-(3-chlorophenyl)ethanamine;
(R)—N-(4-chloro-3-(2-morpholinoethoxy)benzyl)-1-(3-chlorophenyl)ethanamine;
(R)—N-(4-chloro-3-(pyridin-2-ylmethoxy)benzyl)-1-(3-chlorophenyl)ethanamine;
5-((2-chloro-5-(((R)-1-(3-chlorophenyl)ethylamino)methyl) phenoxy)methyl)oxazolidin-2-one;
(R)—N-(4-chloro-3-((3,5-dimethylisoxazol-4-yl)methoxy) benzyl)-1-(3-chlorophenyl)ethanamine;

1-(2-Chloro-5-(((R)-1-(3-chlorophenyl)ethylamino)methyl)phenoxy)propan-2-ol;
(1R)—N-(4-chloro-3-(1-(pyridin-2-yl)ethoxy)benzyl)-1-(3-chlorophenyl)ethanamine;
(1R)—N-(4-Chloro-3-(1-(methylsulfonyl)pyrrolidin-3-yloxy)benzyl)-1-(3-chlorophenyl)ethanamine;
(R)-2-(2-Chloro-5-((1-(3-chlorophenyl)ethylamino)methyl)phenoxy)acetic acid;
(R)-2-((2-Chloro-5-((1-(3-chlorophenyl)ethylamino)methyl)phenoxy)methyl)oxazole-4-carboxylic acid;
N-(2-Chloro-5-(1-((R)-1-(3-chlorophenyl)ethylamino)ethyl)phenyl)-5-methylisoxazole-3-carboxamide;
(R)—N-(3-(4-Methoxyphenyl)-4,5-dimethoxybenzyl)-1-phenylethanamine;
(R)—N-(4-Methoxy-3-(pyrrolidin-1-yl)benzyl)-1-(3-fluorophenyl)ethanamine;
(3-Cyclopentyloxy-4-methoxy-benzyl)-[(S)-1-(3-methoxy-phenyl)-ethyl]-amine;
(3-Cyclopentyloxy-4-methoxy-benzyl)-[(R)-1-(4-methoxy-phenyl)-ethyl]-amine;
(3-Cyclopentyloxy-4-methoxy-benzyl)-((R)-1-p-tolyl-ethyl)-amine;
(3-Cyclopentyloxy-4-methoxy-benzyl)-((R)-1-naphthalen-1-yl-ethyl)-amine;
(3-Cyclopentyloxy-4-methoxy-benzyl)-((R)-1-phenyl-ethyl)-amine;
[3-(Cyclohex-2-enyloxy)-4-methoxy-benzyl]-[(R)-1-(4-methoxy-phenyl)-ethyl]-amine;
[3-(Cyclohex-2-enyloxy)-4-methoxy-benzyl]-((R)-1-p-tolyl-ethyl)-amine;
[3-(Cyclohex-2-enyloxy)-4-methoxy-benzyl]-((R)-1-naphthalen-1-yl-ethyl)-amine;
[3-(Cyclohex-2-enyloxy)-4-methoxy-benzyl]-((R)-1-phenyl-ethyl)-amine;
[(R)-1-(4-Methoxy-phenyl)-ethyl]-[3-(2-phenoxy-ethoxy)-benzyl]-amine;
[3-(2-Phenoxy-ethoxy)-benzyl]-((S)-1-phenyl-ethyl)-amine;
[(S)-1-(3-Methoxy-phenyl)-ethyl]-[3-(pyridin-2-ylmethoxy)-benzyl]-amine;
((S)-1-Naphthalen-1-yl-ethyl)-[3-(pyridin-2-ylmethoxy)-benzyl]-amine;
5-Methyl-isoxazole-3-carboxylic acid {3-[((S)-1-p-tolyl-ethylamino)-methyl]-phenyl}-amide;
5-Methyl-isoxazole-3-carboxylic acid {3-[((S)-1-naphthalen-1-yl-ethylamino)-methyl]-phenyl}-amide;
5-Methyl-isoxazole-3-carboxylic acid {3-[((S)-1-phenyl-ethylamino)-methyl]-phenyl}-amide;
Thiophene-2-carboxylic acid (3-{[(S)-1-(3-methoxy-phenyl)-ethylamino]-methyl}-phenyl)-amide;
Thiophene-2-carboxylic acid {3-[((S)-1-naphthalen-1-yl-ethylamino)-methyl]-phenyl}-amide;
5-Methyl-isoxazole-3-carboxylic acid (3-{[(S)-1-(3-methoxy-phenyl)-ethylamino]-methyl}-phenyl)-amide;
1-{4-[2-(3-{[(S)-1-(3-Methoxy-phenyl)-ethylamino]-methyl}-phenoxy)-ethyl]-piperazin-1-yl}-ethanone;
1-[4-(2-{3-[((S)-1-Naphthalen-1-yl-ethylamino)-methyl]-phenoxy}-ethyl)-piperazin-1-yl]-ethanone;
4-Acetyl-piperazine-1-carboxylic acid 2-(3-{[(S)-1-(3-methoxy-phenyl)-ethylamino]-methyl}-phenoxy)-ethyl ester;
4-Acetyl-piperazine-1-carboxylic acid 2-{3-[((S)-1-naphthalen-1-yl-ethylamino)-methyl]-phenoxy}-ethyl ester;
1-{4-[3-(3-{[(S)-1-(3-Methoxy-phenyl)-ethylamino]-methyl}-phenoxy)-propyl]-piperazin-1-yl}-ethanone;
1-[4-(3-{3-[((S)-1-Naphthalen-1-yl-ethylamino)-methyl]-phenoxy}-propyl)-piperazin-1-yl]-ethanone;
[(S)-1-(3-Methoxy-phenyl)-ethyl]-{3-[2-(4-phenyl-piperazin-1-yl)-ethoxy]-benzyl}-amine;
((S)-1-Naphthalen-1-yl-ethyl)-{3-[2-(4-phenyl-piperazin-1-yl)-ethoxy]-benzyl}-amine;
N-(3-{[(S)-1-(3-Methoxy-phenyl)-ethylamino]-methyl}-phenyl)-2-pyrrolidin-1-yl-acetamide;
N-{3-[((S)-1-Naphthalen-1-yl-ethylamino)-methyl]-phenyl}-2-pyrrolidin-1-yl-acetamide;
Furan-2-yl-[4-(2-{3-[((S)-1-naphthalen-1-yl-ethylamino)-methyl]-phenoxy}-ethyl)-piperazin-1-yl]-methanone;
1-{4-[2-(2-Methoxy-5-{[(S)-1-(3-methoxy-phenyl)-ethylamino]-methyl}-phenoxy)-ethyl]-piperazin-1-yl}-ethanone;
1-[4-(2-{2-Methoxy-5-[((R)-1-naphthalen-1-yl-ethylamino)-methyl]-phenoxy}-ethyl)-piperazin-1-yl]-ethanone;
Furan-2-yl-{4-[2-(2-methoxy-5-{[(S)-1-(3-methoxy-phenyl)-ethylamino]-methyl}-phenoxy)-ethyl]-piperazin-1-yl}-methanone;
{4-Methoxy-3-[2-(4-pyrimidin-2-yl-piperazin-1-yl)-ethoxy]-benzyl}-((R)-1-naphthalen-1-yl-ethyl)-amine;
4-(Furan-2-carbonyl)-piperazine-1-carboxylic acid 2-(2-methoxy-5-{[(S)-1-(3-methoxy-phenyl)-ethylamino]-methyl}-phenoxy)-ethyl ester;
[(S)-1-(3-Methoxy-phenyl)-ethyl]-{3-[2-(4-pyrimidin-2-yl-piperazin-1-yl)-ethoxy]-benzyl}-amine;
4-(Furan-2-carbonyl)-piperazine-1-carboxylic acid 2-(3-{[(S)-1-(3-methoxy-phenyl)-ethylamino]-methyl}-phenoxy)-ethyl ester;
{3-[2-(4-Benzo[1,3]dioxol-5-ylmethyl-piperazin-1-yl)-ethoxy]-benzyl}-[(R)-1-(4-methoxy-phenyl)-ethyl]-amine;
Furan-2-yl-{4-[2-(3-{[(S)-1-(3-methoxy-phenyl)-ethylamino]-methyl}-phenoxy)-ethyl]-piperazin-1-yl}-methanone;
[(S)-1-(3-Methoxy-phenyl)-ethyl]-[3-(morpholine-4-sulfonyl)-benzyl]-amine;
[3-(Morpholine-4-sulfonyl)-benzyl]-((S)-1-naphthalen-1-yl-ethyl)-amine;
[3-(Morpholine-4-sulfonyl)-benzyl]-((S)-1-phenyl-ethyl)-amine;
((S)-1-Naphthalen-1-yl-ethyl)-[3-(piperidine-1-sulfonyl)-benzyl]-amine;
((S)-1-Phenyl-ethyl)-[3-(piperidine-1-sulfonyl)-benzyl]-amine; and
N-{2-Methoxy-5-[((R)-1-naphthalen-1-yl-ethylamino)-methyl]-phenyl}-N-methyl-benzamide.

In one aspect, the invention provides pharmaceutical compositions comprising compounds of Formula I, solvates, prodrugs and pharmaceutically acceptable salts thereof and a pharmaceutically acceptable diluent or carrier.

In one aspect, the invention provides methods of using compounds of Formula I, or solvates, prodrugs and pharmaceutically acceptable salts thereof for the treatment of osteoporosis or hyperparathyroidism. In another aspect, the compounds of Formula I can be used for the treatment of vascular calcification. In a further aspect, compounds of Formula I can be used for the treatment of abnormal intestinal motility. In one aspect, abnormal intestinal motility can be diarrhea. In one aspect, the compounds of Formula I can be used for the treatment of malassimilation or malnutrition.

The invention further provides processes of making compounds of Formula I comprising the step of reacting a compound having the structure

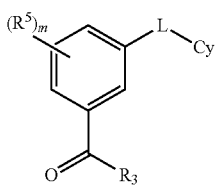

with an amine having the structure

to obtain the product.

DETAILED DESCRIPTION OF THE INVENTION

I. Definitions

"Treating" or "treatment" of a disease includes: (1) preventing the disease, i.e., causing the clinical symptoms of the disease not to develop in a subject that may be or has been exposed to the disease or conditions that may cause the disease, or predisposed to the disease but does not yet experience or display symptoms of the disease, (2) inhibiting the disease, i.e., arresting or reducing the development of the disease or any of its clinical symptoms, or (3) relieving the disease, i.e., causing regression of the disease or any of its clinical symptoms.

The phrase "therapeutically effective amount" is the amount of the compound of the invention that will achieve the goal of prevention of the disorder or improvement in disorder severity and the frequency of incidence. The improvement in disorder severity includes the reversal of the disease, as well as slowing down the progression of the disease.

As used herein, "calcium sensing receptor" or "CaSR" refers to the G-protein-coupled receptor responding to changes in extracellular calcium and/or magnesium levels. Activation of the CaSR produces rapid, transient increases in cytosolic calcium concentration by mobilizing calcium from thapsigargin-sensitive intracellular stores and by increasing calcium influx though voltage-insensitive calcium channels in the cell membrane (Brown et al., Nature 366: 575-580, 1993; Yamaguchi et al., *Adv Pharmacol* 47: 209-253, 2000).

Unless otherwise specified, the following definitions apply to terms found in the specification and claims:

The term "alkyl" by itself or as part of another substituent, means, unless otherwise stated, a straight or branched chain, or cyclic, saturated hydrocarbon having the indicated number of carbon atoms (i.e., $C_1$-$C_8$ means one to eight carbons). For example, ($C_1$-$C_8$) alkyl is meant to include, but is not limited to methyl, ethyl, propyl, isopropyl, butyl, sec-butyl, tert-butyl, pentyl, isopentyl, neopentyl, hexyl, isohexyl, cyclohexyl, cyclohexylmethyl, cyclopropylmethyl and neohexyl.

The term "alkenyl" as used herein refers to a straight or branched chain unsaturated hydrocarbon having the indicated number of carbon atoms (i.e., $C_2$-$C_8$ means two to eight carbons) and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene.

The term "alkylene" refers to a divalent alkyl group (e.g., an alkyl group attached to two other moieties, typically as a linking group). Examples of a ($C_1$-$C_8$) alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. The term "alkenylene" refers to a divalent alkenyl group (e.g., an alkenyl group attached to two other moieties, typically as a linking group). Examples of a ($C_2$-$C_8$) alkenylene group include —CH=CH—, —$CH_2$CH=CH—, —$CH_2$CH=CH$CH_2$—, as well as branched versions thereof.

Typically, an alkyl, alkenyl, alkylene, or alkenylene group will have from 1 to 24 carbon atoms, with those groups having 10 or fewer carbon atoms being preferred in the present invention. A "lower alkyl" "lower alkenyl" or "lower alkylene" is a shorter chain alkyl or alkylene group, generally having eight or fewer carbon atoms.

The term "heteroatom" is meant to include oxygen (O), nitrogen (N), sulfur (S) and silicon (Si).

The term "cycloalkyl" by itself or in combination with other terms, represents, unless otherwise stated, cyclic version of "alkyl". Thus, the term "cycloalkyl" is meant to be included in the terms "alkyl". Examples of cycloalkyl include cyclopentyl, cyclohexyl, 1-cyclohexenyl, 3-cyclohexenyl, cycloheptyl, cyclobutylene, cyclohexylene and the like.

The term "aryl" as used herein refers to a 6- to 14-membered monocyclic, bicyclic or tricyclic aromatic hydrocarbon ring system. Examples of an aryl group include phenyl and naphthyl.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl. A heteroaryl group can be unsubstituted or optionally substituted with one or more substituents as described herein below.

The terms "arylalkyl" and "heteroarylalkyl" are meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like). "Heteroarylalkyl" is meant to include those radicals in which a heteroaryl group is attached to an alkyl group.

The term "heterocycle", "heterocyclic residue" or "heterocyclyl" as used herein refer to 3- to 14-membered ring systems which are either saturated, unsaturated, or aromatic, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic and tricyclic ring systems may encompass a heterocycle or heteroaryl fused to a benzene ring. The heterocycle may be attached via any heteroatom or carbon atom. Heterocycles include heteroaryls, heterocycloalkyls, and heterocycloalkenyls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "alkoxy" as used herein refers to an —O-alkyl group. For example, an alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl. The term "alkoxyalkyl" refers to an alkoxy group appended to an alkyl radical. The term "aryloxy" as used herein refers to an —O-aryl group. The term "alkoxyaryl" refers to an alkoxy group attached to an aryl radical.

The term "amino" refers to a chemical functionality —NR'R", wherein R' and R' are independently hydrogen, alkyl or aryl.

The term "aminoalkyl," as used herein, refers to an alkyl group (typically one to eight carbon atoms) wherein one or more of the $C_1$-$C_8$ alkyl group's hydrogen atoms is replaced with an amine of formula —$N(R^d)_2$, wherein each occurrence of $R^d$ is independently —H or ($C_1$-$C_8$)alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like. The term "alkylamino" refers to an amino group wherein one or more hydrogen atoms is replaced with an alkyl group. Similarly, the term "dialkylamino" refers to an amino group having two attached alkyl groups that can be the same or different.

The term "halo" or "halogen" as used herein refers to —F, —Cl, —Br or —I.

The term "haloalkyl," as used herein, refers to a $C_1$-$C_6$ alkyl group wherein one or more of the $C_1$-$C_6$ alkyl group's hydrogen atoms is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "protected" with respect to hydroxyl groups, amine groups, carboxyl groups and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., ($3^{rd}$ Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The compounds of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of the compounds of the invention, including tautomeric forms of the compound.

Certain compounds of the invention may have asymmetric centers and therefore exist in different enantiomeric and diastereomeric forms. A compound of the invention can be in the form of an optical isomer or a diastereomer. Accordingly, the invention encompasses calcium-sensing receptor modulators and their uses as described herein in the form of their optical isomers, and mixtures thereof, including a racemic mixture. Optical isomers of the calcium-sensing receptor modulators can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester, but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, e.g., cancer therapeutic agents, research reagents, e.g., assay reagents, and diagnostic agents, e.g., in vivo imaging agents. All isotopic variations of the compounds of the invention, whether radioactive or not, are intended to be encompassed within the scope of the invention.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

II. Compounds that Modulate Calcium Sensing Receptor and Pharmaceutical Compositions Comprising them, Administration and Dosage As used herein, the term "calcimimetic compound" or "calcimimetic" refers to a compound that binds to calcium sensing receptors and induces a conformational change that reduces the threshold for calcium sensing receptor activation by the endogenous ligand $Ca^{2+}$. These calcimimetic compounds can also be considered allosteric modulators of the calcium receptors.

In one aspect, a calcimimetic can have one or more of the following activities: it evokes a transient increase in internal calcium, having a duration of less than 30 seconds (for example, by mobilizing internal calcium); it evokes a rapid increase in $[Ca^{2+}]_i$ occurring within thirty seconds; it evokes a sustained increase (greater than thirty seconds) in $[Ca^{2+}]_i$ (for example, by causing an influx of external calcium); evokes an increase in inositol-1,4,5-triphosphate or diacylglycerol levels, usually within less than 60 seconds; and inhibits dopamine- or isoproterenol-stimulated cyclic AMP formation. In one aspect, the transient increase in $[Ca^{2+}]_i$ can be abolished by pretreatment of the cell for ten minutes with 10 mM sodium fluoride or with an inhibitor of phospholipase C, or the transient increase is diminished by brief pretreatment (not more than ten minutes) of the cell with an activator of protein kinase C, for example, phorbol myristate acetate (PMA), mezerein or (−) indolactam V.

While the compounds of the invention are believed to exert their effects by interacting with the calcium sensing receptor (CaSR), the mechanism of action by which the compounds act is not a limiting embodiment of the invention. For example, compounds of the invention may interact with calcium sensing receptors other than CaSR.

Compounds contemplated by the invention include, but are not limited to, the exemplary compounds provided herein.

In certain embodiments, the calcimimetic compound is chosen from compounds of Formula I or a stereoisomer, a tautomer, a solvate, a pharmaceutically acceptable salt, or a prodrug thereof:

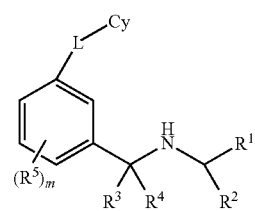

I wherein R¹ is phenyl, benzyl, naphthyl or a saturated or unsaturated 5- or 6-membered heterocyclic ring containing 1, 2 or 3 atoms selected from N, O and S, with no more than 2 of the atoms selected from O and S, wherein the phenyl, benzyl, naphthyl or heterocyclic ring are substituted by 0, 1, 2 or 3 substituents selected from $C_{1-6}$alkyl, halogen, $C_{1-4}$haloalkyl, —$OC_{1-6}$alkyl, cyano and nitro;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, —$OC_{1-6}$alkyl, —$NR^aR^d$, $NR^aC(=O)R^d$, substituted or unsubstituted pyrrolidinyl, substituted or unsubstituted azetidinyl, or substituted or unsubstituted piperidyl, wherein the substituents can be selected from halogen, —$OR^b$, —$NR^aR^d$, —$C(=O)OR^c$, —$C(=O)NR^aR^d$, —$OC(=O)R^c$, —$NR^aC(=O)R^c$, cyano, nitro, —$NR^aS(=O)_nR^c$ or —$S(=O)_nNR^aR^d$;

L is —O—, —$OC_{1-6}$alkyl-, —$C_{1-6}$alkylO—, —N($R^a$)($R^d$)—, —$NR^aC(=O)$—, —$C(=O)$—, —$C(=O)NR^d$$C_{1-6}$alkyl-, —$C_{1-6}$alkyl-$C(=O)NR^d$—, —$NR^dC(=O)NR^d$—, —$NR^dC(=O)NR^dC_{1-6}$alkyl-, —$NR^aC(=O)R^c$—, —$NR^aC(=O)OR^c$—, —$OC_{1-6}$alkyl-$C(=O)O$—, —$NR^d$$C_{1-6}$alkyl-, —$C_{1-6}$alkyl$NR^d$, —S—, —$S(=O)_n$—, $NR^aS(=O)_n$, or —$S(=O)_nN(R^a)$—;

Cy is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $R^6$, $C_{1-8}$alkyl, $C_{1-4}$haloalkyl, halogen, cyano, nitro, —$OC_{1-6}$alkyl, —$NR^aR^d$, $NR^dC(=O)R^d$, —$C(=O)OR^c$, —$C(=O)NR^aR^d$, —$OC(=O)R^c$, —$NR^aC(=O)R^c$, —$NR^aS(=O)_mR^c$ or —$S(=O)_mNR^aR^d$;

$R^a$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $C_{1-8}$alkyl, $C_{1-4}$haloalkyl, halogen, cyano, nitro, —$OC_{1-6}$alkyl, —$NR^aR^d$, $NR^dC(=O)R^d$, —$C(=O)OR^c$, —$C(=O)NR^aR^d$, —$OC(=O)R^c$, —$NR^aC(=O)R^c$, —$NR^aS(=O)_mR^c$ or —$S(=O)_mNR^aR^d$;

$R^a$ is, independently, at each instance, H, $C_{1-4}$haloalkyl, $C_{1-6}$alkyl, $C_{1-6}$alkenyl, $C_{1-6}$alkylaryl or aryl$C_{1-6}$alkyl:

$R^b$ is, independently, at each instance, $C_{1-8}$alkyl, $C_{1-4}$haloalkyl, phenyl, benzyl, naphthyl or a saturated or unsaturated 5- or 6-membered heterocyclic ring containing 1, 2 or 3 atoms selected from N, O and S, with no more than 2 of the atoms selected from O and S, wherein the phenyl, benzyl, naphthyl or heterocyclic ring are substituted by 0, 1, 2 or 3 substituents selected from $C_{1-6}$alkyl, halogen, $C_{1-4}$haloalkyl, —$OC_{1-6}$alkyl, cyano and nitro;

$R^c$ is, independently, at each instance, $C_{1-8}$alkyl, $C_{1-4}$haloalkyl, phenyl or benzyl;

$R^d$ is, independently, at each instance, H, $C_{1-6}$alkyl, $C_{1-6}$alkenyl, phenyl, benzyl, naphthyl or a saturated or unsaturated 5- or 6-membered heterocycle ring containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —$C(=O)R^c$, —$OR^b$, —$NR^aR^b$, —$C(=O)OR^c$, —$C(=O)NR^aR^b$, —$OC(=O)R^c$, —$NR^aC(=O)R^c$, —$NR^aS(=O)_nR^c$ and —$S(=O)_mNR^aR^a$;

m is 1 or 2;

n is 1 or 2;

provided that if L is —O— or —$OC_{1-6}$alkyl-, then Cy is not phenyl.

In one aspect, the invention provides compounds of Formula I, wherein R¹ is phenyl substituted by 0, 1, 2 or 3 substituents selected from $C_{1-6}$alkyl, halogen, $C_{1-4}$haloalkyl, —$OC_{1-6}$alkyl, cyano and nitro. In another aspect, $R^1$ can be naphthyl substituted by 0, 1, 2 or 3 substituents selected from $C_{1-6}$alkyl, halogen, $C_{1-4}$haloalkyl, —$OC_{1-6}$alkyl, cyano and nitro. In one aspect, $R^3$ can be H. In another aspect, $R^4$ can be H.

In one aspect, $R^5$ can be H or halogen. In one aspect, halogen can be Cl. In another aspect, $R^5$ can be methoxy. In a further aspect, $R^5$ can be substituted or unsubstituted piperidyl, wherein the substituents can be selected from halogen, —$OR^b$, —$NR^aR^d$, —$C(=O)OR^c$, —$C(=O)NR^aR^d$, —$OC(=O)R^c$, —$NR^aC(=O)R^c$, cyano, nitro, —$NR^aS(=O)_nR^c$ or —$S(=O)_nNR^aR^d$.

The invention provides compounds of Formula I, wherein L can be —$NR^aC(=O)$—. In one aspect, $R^a$ is H. The invention further provides compounds of Formula I, wherein L can be —$NR^aC(=O)OR^c$—. In one aspect, L can be —S—. In another aspect, L can be —$NR^dC(=O)NR^d$—. In one aspect, $R^d$ can be H. In another aspect, L can be $S(=O)_n$—. In a further aspect, L can be —$NR^dC_{1-6}$alkyl-.

The invention further provides compounds of Formula I, wherein Cy can be optionally substituted heterocyclyl. In one aspect, Cy can be optionally substituted aryl or heteroaryl. In one aspect, Cy can be optionally substituted phenyl. In one aspect, Cy can be optionally substituted pyridyl. In another aspect, Cy can be optionally substituted isoxazolyl, optionally substituted thiophenyl, optionally substituted imidazolyl, optionally substituted thiadiazolyl, optionally substituted pyrazolyl, optionally substituted furanyl, or optionally substituted oxadiazolyl.

In one aspect, the invention provides compounds, stereoisomers, tautomers, solvates, pharmaceutically acceptable salts, or prodrugs thereof, wherein the compounds are selected from the group consisting of:

(R)—N-(2-Chloro-5-((1-(3-chlorophenyl)ethylamino)methyl)phenyl)-5-methylisoxazole-3-carboxamide;

N-(2-chloro-5-((((1R)-1-phenylethyl)amino)methyl)phenyl)acetamide;

N-(2-chloro-5-((((1R)-1-phenylethyl)amino)methyl)phenyl)-2-furancarboxamide;

N-(2-chloro-5-((((1R)-1-phenylethyl)amino)methyl)phenyl)-1,3-dimethyl-1H-pyrazole-5-carboxamide;

N-(2-chloro-5-((((1R)-1-phenylethyl)amino)methyl)phenyl)-3-phenylpropanamide, 2-chloro-N-(2-chloro-5-((((1R)-1-phenylethyl)amino)methyl)phenyl)acetamide;

N-(2-chloro-5-((((1R)-1-phenylethyl)amino)methyl)phenyl)-2,2-dimethylpropanamide;

N-(2-chloro-5-((((1R)-1-phenylethyl)amino)methyl)phenyl)benzamide;

N-(2-chloro-5-((((1R)-1-phenylethyl)amino)methyl)phenyl)-2-thiophenecarboxamide;

N-(2-chloro-5-((((1R)-1-phenylethyl)amino)methyl)phenyl)-5-isoxazolecarboxamide;

N-(2-chloro-5-((((1R)-1-phenylethyl)amino)methyl)phenyl)-5-methyl-3-isoxazolecarboxamide;

N-(2-chloro-5-((((1R)-1-phenylethyl)amino)methyl)phenyl)-2-pyridinecarboxamide;

N-(2-chloro-5-((((1R)-1-phenylethyl)amino)methyl)phenyl)-3-pyridinecarboxamide;
N-(2-chloro-5-((((1R)-1-phenylethyl)amino)methyl)phenyl)-4-pyridinecarboxamide; phenylmethyl (2-chloro-5-((((1R)-1-phenylethyl)amino)methyl)phenyl)carbamate;
N-(2-chloro-5-((((1R)-1-phenylethyl)amino)methyl)phenyl)-2,5-dimethyl-1,3-oxazole-4-carboxamide;
N-(2-chloro-5-((((1R)-1-phenylethyl)amino)methyl)phenyl)-4-methyl-1,2,3-thiadiazole-5-carboxamide;
N-(2-chloro-5-((((1R)-1-phenylethyl)amino)methyl)phenyl)-5-(2-methyl-1,3-thiazol-4-yl)-3-isoxazolecarboxamide;
N-(2-chloro-5-((((1R)-1-phenylethyl)amino)methyl)phenyl)-N'-phenylurea;
N-(2-chloro-5-((((1R)-1-phenylethyl)amino)methyl)phenyl)-1-(1,1-dimethylethyl)-5-methyl-1H-pyrazole-3-carboxamide;
N-(2-chloro-5-((((1R)-1-phenylethyl)amino)methyl)phenyl)-5-phenyl-3-isoxazolecarboxamide;
6-chloro-N-(2-chloro-5-((((1R)-1-phenylethyl)amino)methyl)phenyl)-3-pyridinecarboxamide;
N-(2-chloro-5-((((1R)-1-phenylethyl)amino)methyl)phenyl)-3-thiophenecarboxamide;
N-(2-chloro-5-((((1R)-1-phenylethyl)amino)methyl)phenyl)-5-(2-pyridinyl)-2-thiophenecarboxamide;
N-(2-chloro-5-((((1R)-1-phenylethyl)amino)methyl)phenyl)-5-phenyl-2-thiophenecarboxamide;
N-(2-chloro-5-((((1R)-1-(1-naphthalenyl)ethyl)amino)methyl)phenyl)-2-pyridinecarboxamide;
(R)—N-(4-Chloro-3-nitrobenzyl)-1-(3-chlorophenyl)ethanamine;
(R)—N-(4-Chloro-3-(phenylthio)benzyl)-1-(3-chlorophenyl)ethanamine;
(R)—N-(4-chloro-3-(phenylsulfonyl)benzyl)-1-(3-chlorophenyl)ethanamine;
(R)-2-Chloro-5-((1-(3-chlorophenyl)ethylamino)methyl)benzenesulfonamide;
(R)—N-(4-Methoxy-3-(morpholinosulfonyl)benzyl)-1-(3-chlorophenyl)ethanamine;
(R)—N-(4-chloro-3-(morpholinosulfonyl)benzyl)-1-(3-chlorophenyl)ethanamine;
(R)—N-(2-Chloro-5-((1-phenylethylamino)methyl)phenyl)-2-(pyrrolidin-1-yl)acetamide;
(R)—N-(2-chloro-5-((1-phenylethylamino)methyl)phenyl)-6-(dimethylamino)nicotinamide;
N-(2-chloro-5-((((1R)-1-phenylethyl)amino)methyl)phenyl)-6-(4-morpholinyl)-3-pyridinecarboxamide;
N-(2-chloro-5-((((1R)-1-phenylethyl)amino)methyl)phenyl)-6-(4-methyl-1-piperazinyl)-3-pyridinecarboxamide;
N-(2-chloro-5-((((1R)-1-phenylethyl)amino)methyl)phenyl)-6-((2-(dimethylamino) ethyl)amino)-3-pyridinecarboxamide;
N-(2-chloro-5-((((1R)-1-phenylethyl)amino)methyl)phenyl)-6-(methylamino)-3-pyridinecarboxamide;
N-(2-chloro-5-((((1R)-1-phenylethyl)amino)methyl)phenyl)-6-(phenylamino)-3-pyridinecarboxamide;
N-(2-chloro-5-((((1R)-1-phenylethyl)amino)methyl)phenyl)-6-((phenylmethyl)amino)-3-pyridinecarboxamide;
N-(2-chloro-5-((((1R)-1-phenylethyl)amino)methyl)phenyl)-6-((2-phenylethyl)amino)-3-pyridinecarboxamide;
(R)-1-(2-(5-methylisoxazole-3-carboxamido)-4-((1-phenylethylamino)methyl)phenyl)piperidine-4-carboxamide;
(R)-1-(2-Chloro-5-((1-phenylethylamino)methyl)phenyl)piperidine-4-carboxamide;
(R)-2-Chloro-5-((1-phenylethylamino)methyl)-N-(pyridin-2-ylmethyl)benzenamine;
(1R)—N-(3-(1H-Benzo[d]imidazol-1-yl)-4-chlorobenzyl)-1-phenylethanamine;
(1R)—N-(4-chloro-3-(1H-1,2,4-triazol-1-yl)benzyl)-1-phenylethanamine;
((1R)—N-(4-Chloro-3-((1-methylpiperidin-3-yl)methoxy)benzyl)-1-(3-chlorophenyl)ethanamine;
(R)-methyl 2-(2-chloro-5-((1-(3-chlorophenyl)ethylamino)methyl)phenoxy)acetate;
(R)—N-(3-((1,2,4-oxadiazol-3-yl)methoxy)-4-chlorobenzyl)-1-(3-chlorophenyl)ethanamine;
(R)—N-(4-chloro-3-((5-methylisoxazol-3-yl)methoxy)benzyl)-1-(3-chlorophenyl)ethanamine;
(R)—N-(4-chloro-3-((1-methyl-1H-imidazol-2-yl)methoxy)benzyl)-1-(3-chlorophenyl)ethanamine;
(R)—N-(3-((5-tert-butyl-1,2,4-oxadiazol-3-yl)methoxy)-4-chlorobenzyl)-1-(3-chlorophenyl)ethanamine;
(R)-methyl 2-((2-chloro-5-((1-(3-chlorophenyl)ethylamino)methyl)phenoxy)methyl)oxazole-4-carboxylate;
(R)—N-(4-chloro-3-(6-methylpyridazin-3-yloxy)benzyl)-1-(3-chlorophenyl)ethanamine;
(R)—N-(4-chloro-3-(2-morpholinoethoxy)benzyl)-1-(3-chlorophenyl)ethanamine;
(R)—N-(4-chloro-3-(pyridin-2-ylmethoxy)benzyl)-1-(3-chlorophenyl)ethanamine;
5-((2-chloro-5-(((R)-1-(3-chlorophenyl)ethylamino)methyl)phenoxy)methyl)oxazolidin-2-one;
(R)—N-(4-chloro-3-((3,5-dimethylisoxazol-4-yl)methoxy)benzyl)-1-(3-chlorophenyl)ethanamine;
1-(2-Chloro-5-(((R)-1-(3-chlorophenyl)ethylamino)methyl)phenoxy)propan-2-ol;
(1R)—N-(4-chloro-3-(1-(pyridin-2-yl)ethoxy)benzyl)-1-(3-chlorophenyl)ethanamine;
(1R)—N-(4-Chloro-3-(1-(methylsulfonyl)pyrrolidin-3-yloxy)benzyl)-1-(3-chlorophenyl)ethanamine;
(R)-2-(2-Chloro-5-((1-(3-chlorophenyl)ethylamino)methyl)phenoxy)acetic acid;
(R)-2-((2-Chloro-5-((1-(3-chlorophenyl)ethylamino)methyl)phenoxy)methyl)oxazole-4-carboxylic acid;
N-(2-Chloro-5-(1-((R)-1-(3-chlorophenyl)ethylamino)ethyl)phenyl)-5-methylisoxazole-3-carboxamide;
(R)—N-(3-(4-Methoxyphenyl)-4,5-dimethoxybenzyl)-1-phenylethanamine;
(R)—N-(4-Methoxy-3-(pyrrolidin-1-yl)benzyl)-1-(3-fluorophenyl)ethanamine;
(3-Cyclopentyloxy-4-methoxy-benzyl)-[(S)-1-(3-methoxyphenyl)-ethyl]-amine;
(3-Cyclopentyloxy-4-methoxy-benzyl)-[(R)-1-(4-methoxyphenyl)-ethyl]-amine;
(3-Cyclopentyloxy-4-methoxy-benzyl)-((R)-1-p-tolyl-ethyl)-amine;
(3-Cyclopentyloxy-4-methoxy-benzyl)-((R)-1-naphthalen-1-yl-ethyl)-amine;
(3-Cyclopentyloxy-4-methoxy-benzyl)-((R)-1-phenyl-ethyl)-amine;
[3-(Cyclohex-2-enyloxy)-4-methoxy-benzyl]-[(R)-1-(4-methoxy-phenyl)-ethyl]-amine;
[3-(Cyclohex-2-enyloxy)-4-methoxy-benzyl]-((R)-1-p-tolyl-ethyl)-amine;
[3-(Cyclohex-2-enyloxy)-4-methoxy-benzyl]-((R)-1-naphthalen-1-yl-ethyl)-amine;
[3-(Cyclohex-2-enyloxy)-4-methoxy-benzyl]-((R)-1-phenyl-ethyl)-amine;
[(R)-1-(4-Methoxy-phenyl)-ethyl]-[3-(2-phenoxy-ethoxy)-benzyl]-amine;
[3-(2-Phenoxy-ethoxy)-benzyl]-((S)-1-phenyl-ethyl)-amine;

[(S)-1-(3-Methoxy-phenyl)-ethyl]-[3-(pyridin-2-yl-methoxy)-benzyl]-amine;
((S)-1-Naphthalen-1-yl-ethyl)-[3-(pyridin-2-ylmethoxy)-benzyl]-amine;
5-Methyl-isoxazole-3-carboxylic acid {3-[((S)-1-p-tolyl-ethylamino)-methyl]-phenyl}-amide;
5-Methyl-isoxazole-3-carboxylic acid {3-[((S)-1-naphthalen-1-yl-ethylamino)-methyl]-phenyl}-amide;
5-Methyl-isoxazole-3-carboxylic acid {3-[((S)-1-phenyl-ethylamino)-methyl]-phenyl}-amide;
Thiophene-2-carboxylic acid (3-{[(S)-1-(3-methoxy-phenyl)-ethylamino]-methyl}-phenyl)-amide;
Thiophene-2-carboxylic acid {3-[((S)-1-naphthalen-1-yl-ethylamino)-methyl]-phenyl}-amide;
5-Methyl-isoxazole-3-carboxylic acid (3-{[(S)-1-(3-methoxy-phenyl)-ethylamino]-methyl}-phenyl)-amide;
1-{4-[2-(3-{[(S)-1-(3-Methoxy-phenyl)-ethylamino]-methyl}-phenoxy)-ethyl]-piperazin-1-yl}-ethanone;
1-[4-(2-{3-[((S)-1-Naphthalen-1-yl-ethylamino)-methyl]-phenoxy}-ethyl)-piperazin-1-yl]-ethanone;
4-Acetyl-piperazine-1-carboxylic acid 2-(3-{[(S)-1-(3-methoxy-phenyl)-ethylamino]-methyl}-phenoxy)-ethyl ester;
4-Acetyl-piperazine-1-carboxylic acid 2-{3-[((S)-1-naphthalen-1-yl-ethylamino)-methyl]-phenoxy}-ethyl ester;
1-{4-[3-(3-{[(S)-1-(3-Methoxy-phenyl)-ethylamino]-methyl}-phenoxy)-propyl]-piperazin-1-yl}-ethanone;
1-[4-(3-{3-[((S)-1-Naphthalen-1-yl-ethylamino)-methyl]-phenoxy}-propyl)-piperazin-1-yl]-ethanone;
[(S)-1-(3-Methoxy-phenyl)-ethyl]-{3-[2-(4-phenyl-piperazin-1-yl)-ethoxy]-benzyl}-amine;
((S)-1-Naphthalen-1-yl-ethyl)-{3-[2-(4-phenyl-piperazin-1-yl)-ethoxy]-benzyl}-amine;
N-(3-{[(S)-1-(3-Methoxy-phenyl)-ethylamino]-methyl}-phenyl)-2-pyrrolidin-1-yl-acetamide;
N-{3-[((S)-1-Naphthalen-1-yl-ethylamino)-methyl]-phenyl}-2-pyrrolidin-1-yl-acetamide;
Furan-2-yl-[4-(2-{3-[((S)-1-naphthalen-1-yl-ethylamino)-methyl]-phenoxy}-ethyl)-piperazin-1-yl]-methanone;
1-{4-[2-(2-Methoxy-5-{[(S)-1-(3-methoxy-phenyl)-ethylamino]-methyl}-phenoxy)-ethyl]-piperazin-1-yl}-ethanone;
1-[4-(2-{2-Methoxy-5-[((R)-1-naphthalen-1-yl-ethylamino)-methyl]-phenoxy}-ethyl)-piperazin-1-yl]-ethanone;
Furan-2-yl-{4-[2-(2-methoxy-5-{[(S)-1-(3-methoxy-phenyl)-ethylamino]-methyl}-phenoxy)-ethyl]-piperazin-1-yl}-methanone;
{4-Methoxy-3-[2-(4-pyrimidin-2-yl-piperazin-1-yl)-ethoxy]-benzyl}-((R)-1-naphthalen-1-yl-ethyl)-amine;
4-(Furan-2-carbonyl)-piperazine-1-carboxylic acid 2-(2-methoxy-5-{[(8)-1-(3-methoxy-phenyl)-ethylamino]-methyl}-phenoxy)-ethyl ester;
[(5)-1-(3-Methoxy-phenyl)-ethyl]-{3-[2-(4-pyrimidin-2-yl-piperazin-1-yl)-ethoxy]-benzyl}-amine;
4-(Furan-2-carbonyl)-piperazine-1-carboxylic acid 2-(3-{[(S)-1-(3-methoxy-phenyl)-ethylamino]-methyl}-phenoxy)-ethyl ester;
{3-[2-(4-Benzo[1,3]dioxol-5-ylmethyl-piperazin-1-yl)-ethoxy]-benzyl}-[(R)-1-(4-methoxy-phenyl)-ethyl]-amine;
Furan-2-yl-{4-[2-(3-{[(S)-1-(3-methoxy-phenyl)-ethylamino]-methyl}-phenoxy)-ethyl]-piperazin-1-yl}-methanone;
[(S)-1-(3-Methoxy-phenyl)-ethyl]-[3-(morpholine-4-sulfonyl)-benzyl]-amine;
[3-(Morpholine-4-sulfonyl)-benzyl]-((S)-1-naphthalen-1-yl-ethyl)-amine;
[3-(Morpholine-4-sulfonyl)-benzyl]-((S)-1-phenyl-ethyl)-amine;
((S)-1-Naphthalen-1-yl-ethyl)-[3-(piperidine-1-sulfonyl)-benzyl]-amine;
((S)-1-Phenyl-ethyl)-[3-(piperidine-1-sulfonyl)-benzyl]-amine; and
N-{2-Methoxy-5-[((R)-1-naphthalen-1-yl-ethylamino)-methyl]-phenyl}-N-methyl-benzamide.

A. Preparation of Compounds

Methods A-H below provide exemplary synthetic methods for the preparation of the compounds of the present invention. One of skill in the art will understand that additional methods are also useful. In other words, the compounds of the invention can be made using organic synthesis using starting materials, reagents and reactions well known in the art.

Certain compounds of the invention may be conveniently prepared by a general process outlined in Method A.

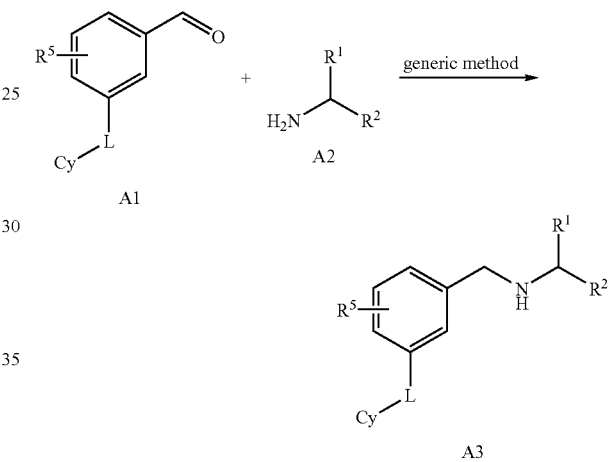

Method A: the aldehyde A1 was dissolved in methanol and the amine A2 is added. The reaction is shaken for 24 hours or until imine formation was complete (as monitored by LCMS), then solid supported borohydride is added (prepared according to Kabalka, G. W.; Wadgaonkar, P. P.; Chatla, N.; Synth. Commun.; (1990), 20 (2), 293-299) and the mixture was shaken for 24 hours or until reduction is complete (as monitored by LCMS). Dichloromethane is then added followed by Wang-aldehyde resin (4-benzyloxybenzaldehyde, polymer-bound) and the mixture is shaken for further 24 hours. The resins were filtered off and the solvents were evaporated under reduced pressure, to afford an oil which is purified by column chromatography (usually Hexane/AcOEt 7/3 or DCM/MeOH 95/5). The free-base oil was then treated with 1.5-2.5 1N HCl in diethyl ether and the solvents were evaporated under reduced pressure to afford the mono or bis-HCl salt of product A3.

Method B: the aldehyde A1 was dissolved in methanol and the amine A2 was added. The reaction was heated to reflux for 10 minutes then left to cool overnight until imine formation was complete (as monitored by LCMS). Solid supported cyanoborohydride is added (prepared according to Sande, A. R.; Jagadale, M. H.; Mane, R. B.; Salunkhe, M. M.; Tetrahedron Lett. (1984), 25(32), 3501-4) and the mixture was heated at 50° C. for 15 hours or until reduction was complete (as monitored by LCMS). Dichloromethane (ca 3 mL) was then added followed by Wang-aldehyde resin (4-benzyloxybenzaldehyde, polymer-bound) and the mixture is shaken for further 24 hours. The resins were filtered off and the solvents were evaporated under reduced pressure, to afford an oil which is purified by column chromatography (usually Hexane/AcOEt 7/3 or DCM/MeOH 95/5). The free-base oil is then treated with 1.5-2.5 1N HCl in diethyl ether and the solvents are evaporated under reduced pressure to afford the mono or bis-HCl salt of product A3.

Method C: The aldehyde A1 was dissolved in 1,2-dichloroethane and the amine A2 was added, followed by acetic acid and finally sodium triacetoxyborohydride. The mixture was stirred overnight or until complete by TLC; upon reaction completion, the mixture was diluted with ethyl acetate, washed with saturated NaHCO$_3$ then with saturated brine, and finally dried over sodium sulphate. The solvents were evaporated under reduced pressure, to afford an oil which is purified by column chromatography on silica gel (usually Hexane/AcOEt 7/3 or DCM/MeOH 95/5). The free-base oil was then treated with 1.5-2.5 equivalents 1N HCl in diethyl ether and the solvents were evaporated under reduced pressure to afford the mono or bis-HCl salt of product A3.

solvent (for example toluene, benzene, chlorobenzene, 1,4-dioxane or the like), followed by aqueous workup yields the $R^3$ substituted $R^4$ amine A7. Reductive coupling of the amine A7 with an aldehyde or ketone A8 according to Method C affords the final product A9.

Method E: Compounds wherein only one of $R^3$ and $R^4$ is hydrogen can be prepared by reacting the α-monosubstituted carboxylic acid obtained by reacting an appropriately substituted phenylacetic acid A4 with a strong base such as lithium diisopropylamide and then with an alkylating agent of formula $R^3$—X as described above, with diphenylphosphoryl azide in a refluxing solvent such as, for example, toluene, benzene, chlorobenzene, 1,4-dioxane, etc. followed by an aqueous workup to yield a mono-α-substituted amine A7. This amine can then be reacted with an aldehyde or ketone A8 according to Method C to obtain the final product A9.

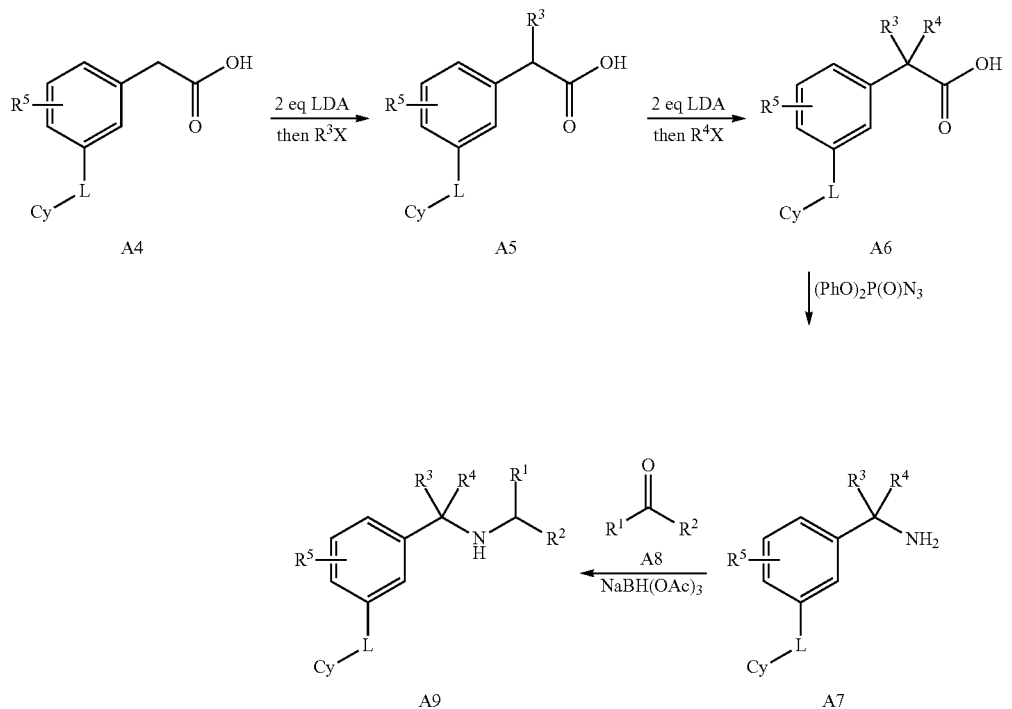

Method D: Compounds wherein both $R^3$ and $R^4$ are other than hydrogen can be prepared by combining an appropriately substituted phenylacetic acid A4 with a strong base such as lithium diisopropylamide or the like at a temperature between −78 and 20° C. to yield a red dianion. The dianion is then reacted with an alkylating agent of formula $R^3$—X, wherein X is a halide, a sulfonate, or other suitable leaving group to provide an $R^3$ substituted compound A5. Treatment of the compound thus obtained with a strong base such as lithium diisopropylamide or the like at a temperature between −78 and 20° C. yields a second red dianion, which is reacted with an alkylating agent of formula $R^4$—X, wherein X is a halide, a sulfonate, or other suitable leaving group to yield the $R^3$, $R^4$ disubstituted compound A6. Treatment of the resultant carboxylic acid with diphenylphosphoryl azide in a refluxing

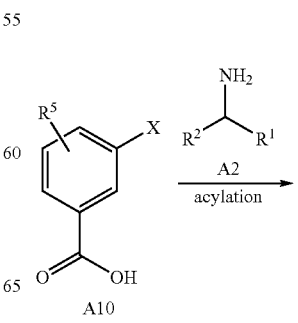

-continued

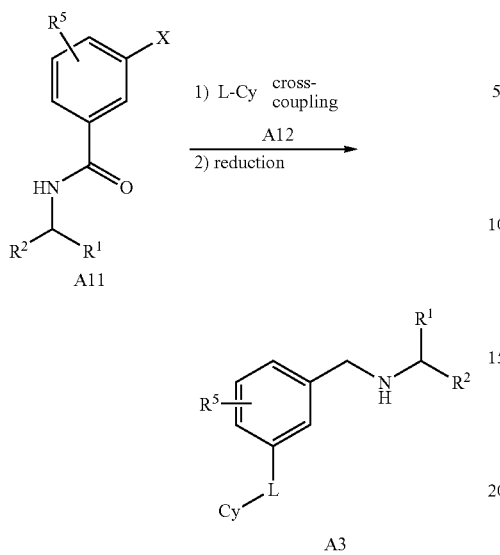

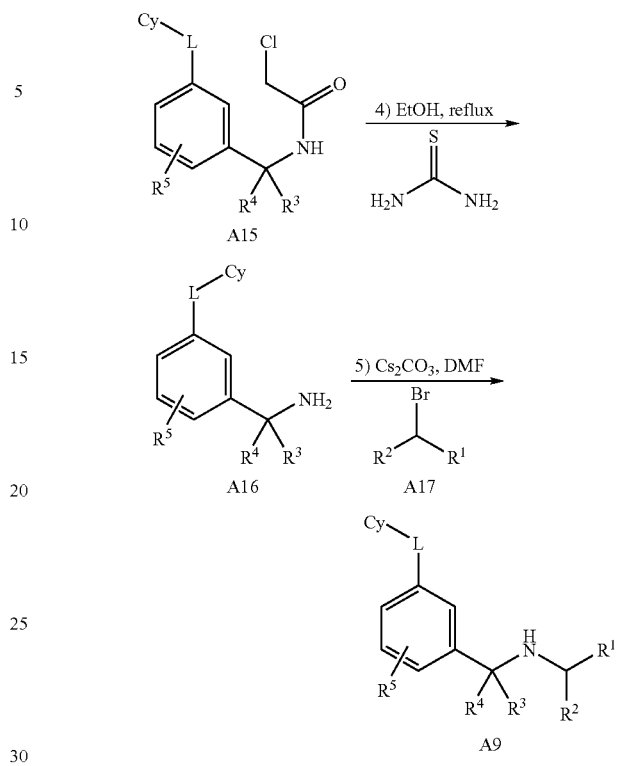

Method F: Acid A10 was dissolved in dimethylformamide at room temperature. 1-Hydroxybenzotriazole hydrate and 1-[3-dimethylamino)propyl]-3-ethylcarbodiimide hydrochloride are added. After 30 min, amine A2 was added and the reaction was allowed to stir overnight. After aqueous work-up, purification by column chromatography on silica gel (usually Hexane/AcOEt 4/1) affords amide A11. Amide A11, cross-coupling partner A12, sodium 2-methylpropan-2-olate, $Pd_2(dba)_3$, 2-(diphenylphosphino)-1-(2-(diphenylphosphino)naphthalen-1-yl)naphthalene, and toluene were combined. Nitrogen was bubbled through the solution for 10 min and the reaction mixture is heated to 80° C. After stirring overnight, aqueous work-up followed by purification by column chromatography on silica gel (usually Hexane/AcOEt 1/1) affords the coupled product. The coupled product was dissolved in THF and 1 M borane in THF is added. After heating to reflux for several days, the reaction mixture was quenched with saturated $NaHCO_3$. Aqueous work-up followed by purification by column chromatography on silica gel (usually AcOEt) affords amine A3.

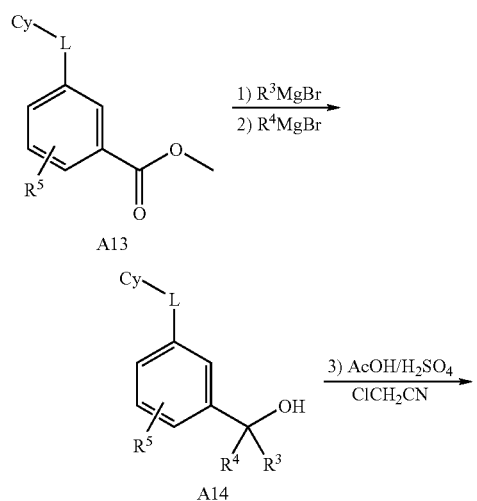

Method G: Ester A13 was dissolved in diethyl ether. The solution is cooled to −78° C. and excess $R^3MgBr$ was added. (Note: if $R^3 \neq R^4$, then one equivalent of $R^3MgBr$ can be added followed by one equivalent of $R^4MgBr$). The reaction mixture was warmed to room temperature and quenched with saturated $NH_4Cl$. Aqueous work-up followed by purification by column chromatography on silica gel (usually Hexane/AcOEt 4/1) affords tertiary alcohol A14. To tertiary alcohol A14 at 0° C. was added 2-chloroacetonitrile, acetic acid, and sulfuric acid. The reaction mixture was warmed to room temperature and stirred for several hours. Aqueous work-up followed by purification by column chromatography on silica gel (usually Hexane/AcOEt 1/1) affords amide A15. Amide A15 was dissolved in ethanol/acetic acid (5:1). Thiourea was added and the reaction mixture is heated to reflux overnight. After aqueous work-up, purification by flash column chromatography on silica gel (usually DCM/MeOH 20/1) affords amine A16. Amine A16 and bromide A17 were combined and dimethylformamide and cesium carbonate were added. The reaction mixture was heated to 40° C. overnight. Aqueous work-up followed by purification by flash column chromatography on silica gel (usually Hexane/AcOEt 4/1) affords amine A9.

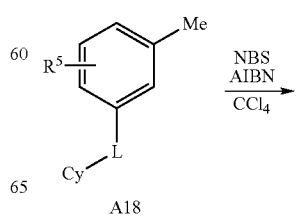

-continued

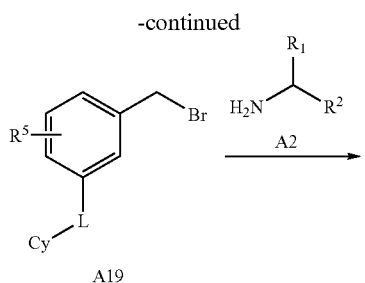

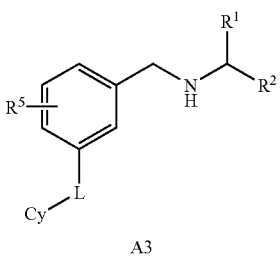

Method H: To a solution of A18 in CCl$_4$ was added N-bromosuccinimide and 2,2'-azobis(2-methylpropionitrile). The reaction mixture was heated to reflux overnight. After aqueous work-up, a solution of the crude reaction mixture in AcOEt was filtered through a pad of silica gel and concentrated to afford bromide A19 which was used without further purification. To a solution of bromide A19 in THF was added amine A2. The reaction mixture was stirred at room temperature for 3 d. After aqueous work-up, purification by flash column chromatography on silica gel (usually Hexane/AcOEt 1/1) affords amine A3.

Regarding the molecular structures set forth in Methods A-H above, one of skill in the art will readily appreciate that precursors and intermediates having aryl groups other than phenyl, e.g. naphthyl, can be used to practice the synthetic methods.

B. Pharmaceutical Compositions and Administration

Compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methansulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al. *J. Pharm. Sci.* 66: 1, 1977. In certain embodiments of the invention salts of hydrochloride and salts of methanesulfonic acid can be used.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the calcium receptor-active compound in the compositions useful in the invention can range from about 0.1 mg to about 180 mg, for example from about 5 mg to about 180 mg, or from about 1 mg to about 100 mg of the calcimimetic compound per subject. In some aspects, the therapeutically effective amount of calcium receptor-active compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a calcium receptor-active compound to a subject alone, the compound administered will normally be present as an active ingredient in a pharmaceutical composition. Thus, a pharmaceutical composition of the invention may comprise a therapeutically effective amount of at least one calcimimetic compound, or an effective dosage amount of at least one calcimimetic compound.

As used herein, an "effective dosage amount" is an amount that provides a therapeutically effective amount of the calcium receptor-active compound when provided as a single dose, in multiple doses, or as a partial dose. Thus, an effective dosage amount of the calcium receptor-active compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the calcimimetic compound is administered by administering a portion of the composition.

Alternatively, a pharmaceutical composition in which two or more unit dosages, such as in tablets, capsules and the like, are required to administer an effective amount of the calcium receptor-active compound may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

III. Therapeutic Uses of the Compounds of the Invention

Compounds and compositions of the present application which act on calcium receptors may thus be used, in one aspect, for the treatment or prevention of diseases or disorders linked with abnormal physiological behaviour of inorganic ion receptors and, in particular, of calcium receptors such as membrane calcium receptors capable of binding extracellular calcium. Thus, the compounds and compositions of the present invention are of particular use in regulating the serum levels of PTH and extracellular $Ca^{2+}$. The compounds and compositions of the present invention can be used, in particular, to participate in a reduction of the serum levels in the parathyroid hormone known as PTH: these products could thus be useful, in one aspect, for the treatment of diseases such as hyperparathyroidism. Similarly, abnormalities in calcium homeostasis, such as hypercalcaemia, can be treated with these compounds. Further, the compounds of the invention can treat hyperplasia and parathyroid adenoma. In another aspect, the compounds of the invention can have properties which enable them to reduce bone resorption which depends directly on the fluctuation of circulating PTH levels: these products could be useful, in particular, for the treatment of diseases such as osteoporosis, osteopaenia Paget's disease and the reconstruction of fractures. They can also be used in the treatment and prophylaxis of polyarthritis and osteoarthritis.

In one aspect, the invention provides a method of inhibiting, decreasing or preventing vascular calcification in an individual. The method comprises administering to the individual a therapeutically effective amount of the calcimimetic compound of the invention. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits.

In one aspect, the compounds of the invention may be used to prevent or treat atherosclerotic calcification and medial calcification and other conditions characterized by vascular calcification. In one aspect, vascular calcification may be associated with chronic renal insufficiency or end-stage renal disease. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

In one aspect, administration of an effective amount of the compounds of the invention can reduce serum PTH without causing aortic calcification. In another aspect, administration of the compounds of the invention can reduce serum creatinine level or can prevent increase of serum creatinine level. In another aspect, administration of the compounds of the invention can attenuates parathyroid (PT) hyperplasia.

The compounds of the invention may be administered alone or in combination with other drugs for treating vascular calcification, such as vitamin D sterols and/or RENAGEL®. Vitamin D sterols can include calcitriol, alfacalcidol, doxercalciferol, maxacalcitol or paricalcitol. In one aspect, the compounds of the invention can be administered before or after administration of vitamin D sterols. In another aspect, the compounds of the invention can be co-administered with vitamin D sterols. The methods of the invention can be practiced to attenuate the mineralizing effect of calcitriol on vascular tissue. In one aspect, the methods of the invention can be used to reverse the effect of calcitriol of increasing the serum levels of calcium, phosphorus and Ca×P product thereby preventing or inhibiting vascular calcification. In another aspect, the compounds of the invention of the invention can be used to stabilize or decrease serum creatinine levels. In one aspect, in addition to creatinine level increase due to a disease, a further increase in creatinine level can be due to treatment with vitamin D sterols such as calcitriol. In addition, the compounds of the invention may be administered in conjunction with surgical and non-surgical treatments. In one aspect, the methods of the invention can be practiced in injunction with dialysis.

In one aspect, the compounds of the invention can be used for treating abnormal intestinal motilities disorders such as diarrhea. The methods of the invention comprise administering to the individual a therapeutically effective amount of the compounds of Formula I.

As used herein, the term "diarrhea" refers to a condition of three or more unformed stools in a 24-hour period of volume more than 200 g per day. In one aspect, diarrhea can be osmotic, i.e., resulting if the osmotic pressure of intestinal contents is higher than that of the serum. This condition may result from malabsorption of fat (e.g., in celiac disease) or of lactose (e.g., in intestinal lactase deficiency), or it can happen due to the use of certain laxatives (e.g., lactulose, magnesium hydroxide) or artificial sweeteners (e.g., sorbitol, mannitol). In another aspect, diarrhea can be secretory, i.e., occurring when there is a net secretion of water into the lumen. This may occur with bacterial toxins (such as those produced, e.g., by *E. coli* and *Vibrio cholerae*), or with hormones, such as vasoactive intestinal polypeptide, which is produced by rare islet cell tumors (pancreatic cholera). Both osmotic and secretory diarrheas result from abnormalities in the small intestine such that the flow of water through the ileocecal area overcomes the absorptive capacity of the colon.

In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with chemotherapy, radiation treatment, inflammation or toxic traumatic injury. In another aspect, exudative diarrhea can be associated with a gastrointestinal or abdominal surgery.

In another aspect, diarrhea can be due to acceleration of intestinal transit (rapid transit diarrhea). Such condition may occur because the rapid flow-through impairs the ability of the gut to absorb water.

In one aspect, the invention provides the compounds and compositions for treating abnormal gastric fluid secretion/absorption disorders in conjunction with treating underlying causes of, for example, diarrhea or with other treatment methods. In one aspect, calcimimetics can be administered to a subject before, after or concurrently with oral rehydration therapy. For example, oral rehydration therapy may contain the following ingredients: sodium, potassium, chloride, bicarbonate, citrate and glucose. In another aspect, the compounds of the invention can be administered to a subject before, after or concurrently with an antimotility agent, such as loperamide (Imodium), diphenoxylate, or bismuth subsalicylate (Pepto-Bismol). In another aspect, calcimimetics can be administered with antibiotics (e.g., trimethoprim-sulfamethoxazole (Bactrim DS), ciprofloxacin (Cipro), norfloxacin (Noroxin), ofloxacin (Floxin), doxycycline (Vibramycin), erythromycin). In one aspect, the compounds of the invention can be administered together with calcium or polyamines such as spermine, spermidine, putrescine, and ornithine metabolites or amino acids such as of L-tryptophan, L-phenylalanine. In another aspect, the compounds of the invention can be administered together with sodium and glucose. In addition, the compounds of the invention may be administered in conjunction with surgical and non-surgical treatments.

The invention further provides methods for modulating intestinal fluid secretion and absorption. In one aspect, the purpose can be to increase fluid absorption and/or decrease fluid secretion in a subject and thus the methods of the invention can comprise administering an effective amount of a pharmaceutical composition comprising a compound of the invention.

The invention provides methods of modulation the absorption or secretion of a drug, poison or nutrient in the intestinal tract of a subject, comprising administering an effective amount of a pharmaceutical composition comprising a compound of the invention together with a pharmaceutically acceptable carrier to the subject. In one aspect, the invention provides methods of treatment of a malassimilation or a malabsorption of a subject, comprising administering an effective amount of a pharmaceutical composition comprising a compound of Formula I together with a pharmaceutically acceptable carrier to the subject.

As used herein, the term "malassimilation" encompasses impaired processes of food digestions and absorption occurring in one of two ways (1) through intraluminal disorders (maldigestion of food) and (2) through intramural disorders (malabsorption of food).

Methods of the invention comprising administering a pharmaceutical composition of the invention can also be practiced to treat malnutrition in a subject. For example, a subject can be malnourished if the subject is grossly underweight (weight for height is below 80% of the standard), grossly overweight (weight for height above 120% of the standard), if the subject unintentionally lost 10% or more of body weight, has a gastrointestinal tract surgery, experienced nutrient losses (e.g., from diarrhea, dialysis, vomiting), has increased metabolic needs (e.g., due to pregnancy, lactation, increased physical activity, fever, injury), is an alcoholic or chronic drug user (antibiotics, antidepressants, diuretics), has medical conditions which interfere with nutrient intake, absorption, metabolism, or utilization, has poor dentition (particularly in the elderly subjects), or has mouth sores due to herpes, HIV or chemotherapy. In another aspect, the subject can be malnourished due to dietary risk factors (e.g., loss of appetite, inadequate food or nutrient intake, lack of variety of foods, fad, weight-loss diets, inadequate fiber, excessive fat, sodium, sugar, excess alcohol, eats too few fruits, vegetables) or due to social risk factors (e.g., chronic ill health, poverty, inadequate money to buy food, low socioeconomic status, immobility or inability to purchase, store, or cook food, social isolation, eats alone most of the time, substance abuser, conditions which limit subject's ability to eat). Further, the methods of the invention can be practiced when a subject has limited access to nutrients such as during survival following environmental disasters, survival at sea, marooning and deep-sea living or space travel.

In one aspect, the podocyte diseases or disorders treated by methods of the present invention stem from the perturbations in one or more functions of podocytes. These functions of podocytes include: (i) a size barrier to protein; (ii) charge barrier to protein; (iii) maintenance of the capillary loop shape; (iv) counteracting the intraglomerular pressure; (v) synthesis and maintenance of the glomerular basement membrane (GMB); (iv) production and secretion of vascular endothelial growth factor (VEGF) required for the glomerular endothelial cell (GEN) integrity.

Such disorders or diseases include but are not limited to loss of podocytes (podocytopenia), podocyte mutation, an increase in foot process width, or a decrease in slit diaphragm length. In one aspect, the podocyte-related disease or disorder can be effacement or a diminution of podocyte density. In one aspect, the diminution of podocyte density could be due to a decrease in a podocyte number, for example, due to apoptosis, detachment, lack of proliferation, DNA damage or hypertrophy.

In one aspect, the podocyte-related disease or disorder can be due to a podocyte injury. In one aspect, the podocyte injury can be due to mechanical stress such as high blood pressure, hypertension, or ischemia, lack of oxygen supply, a toxic substance, an endocrinologic disorder, an infection, a contrast agent, a mechanical trauma, a cytotoxic agent (cis-platinum, adriamycin, puromycin), calcineurin inhibitors, an inflammation (e.g., due to an infection, a trauma, anoxia, obstruction, or ischemia), radiation, an infection (e.g., bacterial, fungal, or viral), a dysfunction of the immune system (e.g., an autoimmune disease, a systemic disease, or IgA nephropathy), a genetic disorder, a medication (e.g., anti-bacterial agent, anti-viral agent, anti-fungal agent, immunosuppressive agent, anti-inflammatory agent, analgestic or anticancer agent), an organ failure, an organ transplantation, or uropathy. In one aspect, ischemia can be sickle-cell anemia, thrombosis, transplantation, obstruction, shock or blood loss. In on aspect, the genetic disorders may include congenital nephritic syndrome of the Finnish type, the fetal membranous nephropathy or mutations in podocyte-specific proteins, such as α-actin-4, podocin and TRPC6.

In one aspect, the podocyte-related disease or disorder can be an abnormal expression or function of slit diaphragm proteins such as podocin, nephrin, CD2AP, cell membrane proteins such as TRPC6, and proteins involved in organization of the cytoskeleton such as synaptopodin, actin binding proteins, lamb-families and collagens. In another aspect, the podocyte-related disease or disorder can be related to a disturbance of the GBM, to a disturbance of the mesangial cell function, and to deposition of antigen-antibody complexes and anti-podocyte antibodies.

In one aspect, the podocyte-related disease or disorder can be proteinuria, such as microalbumiuria or macroalbumiuria. In another aspect, the podocyte-related disease or disorder can be tubular atrophy.

In one aspect, the present invention provides method of treatment or prevention of inflammatory bowel disease using the compounds of the invention. Inflammatory bowel disease, or IBD, as used herein, is a disease characterized by inflammation or ulcerations in the small and/or large intestine with chronically recurring symptoms of abdominal pain and alteration in bowel habits. IBD has been classified into the broad categories of Crohn's disease (CD) and ulcerative colitis (UC). In one aspect, the invention provides methods for treating UC using calcimimetic compounds and compositions. In another aspect, the methods of the invention can be used for treatment of CD using calcimimetic compounds and compositions. In one aspect, methods of the present invention result in prevention of onset or alleviation of one or more signs or symptoms of UC or CD. Table 1 further summarizes inflammatory markers in pathophysiology of IBD and signs/symptoms commonly found in ulcerative colitis and Crohn's disease.

TABLE 1

| Sign/Symptom | Ulcerative Colitis | Crohn's Disease |
| --- | --- | --- |
| Area of intestinal tract affected | Any part of innermost lining of colon, continuous with no patches of normal tissues | Lower ileum most common but can flare up anywhere, including the colon, patches of normal tissue between affected areas; can affect entire intestinal wall |
| Diarrhea | Typically four episodes per day | Typically four episodes per day |
| Abdominal pain/cramping | Mild tenderness, lower abdominal cramping | Moderate to severe abdominal tenderness in right lower quadrant |
| Blood in stool | Present; amount depends on disease severity | May be present; amount depends on disease severity |
| Fatigue | Result of excessive blood loss and anemia | Result of excessive blood loss, anemia, and poor nutrient absorption |
| Fever | Low-grade in severe cases | Low-grade in severe cases |
| Physical examination | Rectal exam may show peri-anal irritation, fissures, hemorrhoids, fistulas, and abscesses | Peritoneal irritation, abdominal or pelvis mass |
| Weight loss/anorexia | Weight loss in more severe cases | Weight loss and anorexia common due to poor digestion and intestinal absorption |
| Appetite | Often decreased during periods of disease exacerbation | Often decreased during periods of disease exacerbation |
| Risk of colon cancer | Increased | Increased |

In one aspect, the present invention provides method of treatment or prevention of irritable bowel syndrome. Irritable bowel syndrome, or IBS, as used herein, is a gastrointestinal disorder characterized by altered bowel habits and abdominal pain, typically in the absence of detectable structural abnormalities or biochemical cause. The Rome II criteria can be used to diagnose IBS and rule out other disorders. The criteria include at least 3 months of the following continuous recurrent symptoms: abdominal pain or discomfort that is relieved by defecation or is associated with a change in the frequency or consistency of stool, and disturbed defecation involving two or more of the following characteristics at least 25% of the time: altered stool frequency, altered stool form (e.g., lumpy or hard, or loose or watery), altered stool passage (e.g., straining, urgency, or feeling of incomplete evacuation), passage of mucus, bloating or feeling of abdominal distention. The intensity and location of abdominal pain in IBS can be highly variable, even within an individual patient: it is localized to the hypogastrium in 25%, the right side in 20%, the left side in 20%, and the epigastrium in 10% of the patients. The pain can be generally crampy or achy, although sharp, dull, gas-like, or non-descript pains are also common. In one aspect, patients with IBS may present with constipation (IBS-C, constipation predominant IBS), diarrhea (IBS-D, diarrhea-predominant IBS), or constipation alternating with diarrhea (IBS-A, mixed symptom IBS, or "alternators"). Long period of straining may be required for fecal evaluation both in constipation- and diarrhea-predominant patient. Constipation may persist for weeks to months, interrupted by brief periods of diarrhea. Feelings of incomplete fecal evacuation may lead to multiple attempts at stool passage daily. In patients with IBS-D, stools are characteristically loose and frequent but of normal daily volume. Mucus discharge has been reported in up to 50% of patients with IBS. Upper gut symptoms are common in IBS, with 25% to 50% of patients reporting heartburn, early satiety, nausea, and vomiting, up to 87% note intermittent dyspepsia. Agreus L. et al. (1995) Gastroenterology 109: 671. Extraintestinal complaints in patients with IBS include chronic pelvic pain, fibromyalgia, genitourinary dysfunctions, such as dysmenorrheal, dyspareunia, impotence, urinary frequency, nocturia, and a sensation of incomplete bladder emptying. Impaired sexual function is reported by 83% of patients with IBS. Patients with functional bowel disorders have higher incidences of hypertension, headaches, peptic ulcer disease, rashes than the general population and more commonly report fatigue, loss of concentration, insomnia, palpitations, and unpleasant tastes in the mouth.

While the pathogenesis of IBS is poorly understood, it has been proposed that abnormal gut motor and sensory activity, central neural dysfunction, psychological disturbances, stress and luminal factors play a role. IBS has been associated with colonic and small intestinal motility abnormalities, as well as with motor abnormalities in other smooth muscle sites. The visceral sensory abnormalities, which may be responsible for sensations of pain, gas, or bloating in IBS, have been a major focus of investigation. Perception of abdominal symptoms is mediated by afferent neural pathways which are activated by visceral stimuli acting on chemoreceptors, mechanoreceptors, and receptors in the mesentery which may play a role in painful stimulation of the gut. Information from these activated receptors is carried in spinal afferent nerves and thus transmitted to the brain where conscious perception occurs. It is postulated that IBS results from sensitization of afferent pathways such that normal physiological gut stimuli not perceived by healthy individuals induce pain in the patient with IBS. The sensitizing event responsible for induction of symptoms in IBS is unknown. The clinical association of emotional disorders and stress with symptom exacerbation and the therapeutic response to therapies that act on cerebral cortical sites strongly suggests the role of central nervous system factors in the pathogenesis of IBS. However, it is unclear whether IBS represents a primary gut disturbance with inappropriate input from the central nervous system or a central nervous system disorder with centrally directed changes in gut motor and sensory activity. Further, both mental stress and administration of the cholinesterase inhibitor neostigmine evoke increases in colonic motility and changes in electroencephalographic waveforms which are exaggerated in patients with IBS compared to healthy volunteers, suggesting that both the gut and brain are hypersensitive in IBS. Investigations of the effects of stress reinforce the importance of the brain-gut axis in the regulation of colonic activities. A strongly positive relationship has been reported between daily stress and daily symptoms in women with IBS. Levy R. et al. (1997) J. Behav. Med. 20: 177.

The present invention, thus generally described, will be understood more readily by reference to the following examples, which are provided by way of illustration and are not intended to be limiting of the present invention. Compounds of the invention may be synthesized from simple starting molecules and commercially available materials as illustrated in Examples. Various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence. The structure of the prepared compounds is verified by mass spectral data. For some compounds, ions having mass greater than M+H are reported. These ions generally represent dimers or trimers of the synthesized compound, and in some instances represent trifluoroacetate adducts generated from the mobile phase of the LC/MS. The trifluoroacetate adducts will have a weight of M+115.

Example 1

Synthesis of (R)—N-(2-Chloro-5-((1-(3-chlorophenyl)ethylamino)methyl)phenyl)-5methylisoxazole-3-carboxamide

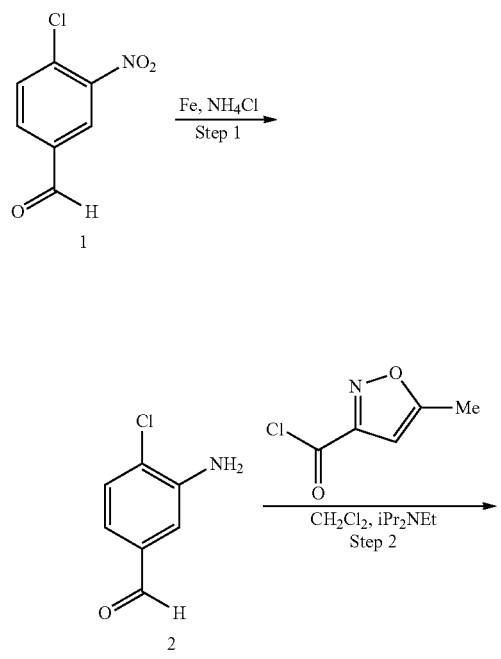

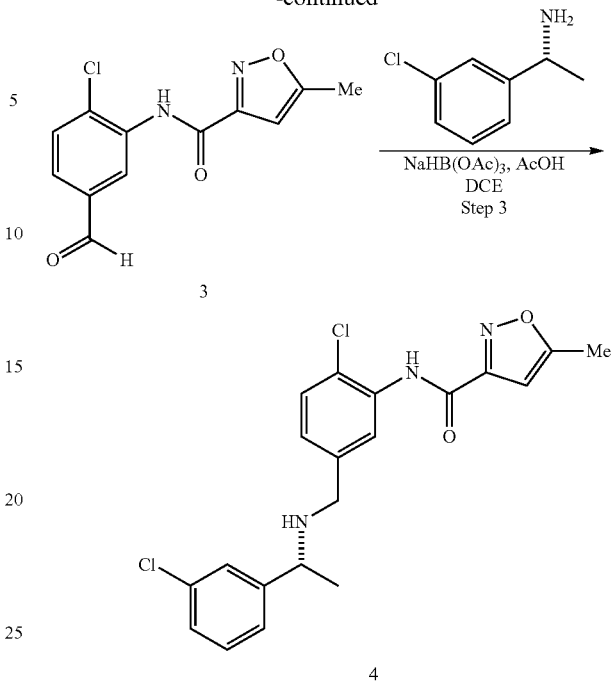

Step 1. To a solution of 4-chloro-3-nitrobenzaldehyde 1 (11.47 g, 62 mmol) in MeOH (230 mL) and water (85 mL) was added ammonium chloride (24.2 g, 452 mmol) and iron (18.4 g, 329 mmol). The reaction mixture was stirred at room temperature for 16 h, filtered, partially concentrated under reduced pressure, and diluted with EtOAc and water. The aqueous phase was extracted with EtOAc (3×) and the combined organic extracts were washed with brine (1×), dried over MgSO$_4$, filtered, and concentrated in vacuo. The crude aniline was dissolved in CH$_2$Cl$_2$ (~150 mL), diluted with hexanes (~300 mL), and cooled to 0° C. The solid was collected by filtration and washed with hexanes to give 3-amino-4-chlorobenzaldehyde 2 (5.36 g, 56% yield) as a yellow solid. Mass spectrum: calculated for C$_7$H$_5$ClNO 155.0. found 156.1 (M$^+$+1).

Step 2. To a solution of 3-amino-4-chlorobenzaldehyde 2 (0.267 g, 1.72 mmol) in DCM (5 mL) at 0° C. was added N-ethyl-N-isopropylpropan-2-amine (0.600 mL, 3.44 mmol) and 5-methylisoxazole-3-carbonyl chloride (0.292 g, 2.01 mmol). The reaction mixture was stirred at 0° C. for 30 min, warmed to room temperature, stirred for 1 h, and diluted with EtOAc. The organic phase was washed with saturated NaHCO$_3$ (1×), brine (1×), dried over MgSO$_4$, filtered, and concentrated in vacuo. Purification by flash column chromatography on silica gel (eluted with 15% to 50% EtOAc in hexanes) gave N-(2-chloro-5-formylphenyl)-5-methylisoxazole-3-carboxamide 3 (0.117 g, 25.8% yield) as a white solid. Mass spectrum: calculated for C$_{12}$H$_9$ClN$_2$O$_3$ 264.0. found 265.0 (M$^+$+1).

Step 3. To a solution of N-(2-chloro-5-formylphenyl)-5-methylisoxazole-3-carboxamide 3 (0.117 g, 0.44 mmol) in DCE (3 mL) was added (R)-1-(3-chlorophenyl)ethanamine (0.079 g, 0.51 mmol), acetic acid (0.030 mL, 0.52 mmol), and NaBH(OAc)$_3$ (0.108 g, 0.51 mmol). The reaction mixture was stirred at room temperature for 16 h and diluted with EtOAc. The organic phase was washed with saturated NaHCO$_3$ (1×), brine (1×), dried over MgSO$_4$, filtered, and concentrated in vacuo. Purification by flash column chromatography on silica gel (eluted with 20% to 60% EtOAc in hexanes) gave (R)—N-(2-chloro-5-((1-(3-chlorophenyl)ethylamino)methyl)phenyl)-5-methylisoxazole-3-carboxamide 4 (0.131 g, 73% yield) as a colorless oil. $^1$H NMR (400 MHz, CDCl$_3$) δ 1.36 (d, J=6.5 Hz, 3H), 2.53 (s, 3H), 3.60 (d, J=13.7 Hz, 1H), 3.66 (d, J=13.7 Hz, 1H), 3.79 (q, J=6.5 Hz, 1H), 6.53 (s, 1H), 7.04 (d, J=8.2 Hz, 1H), 7.21-7.36 (m, 6H), 8.41 (s, 1H), 9.10 (s br, 1H). Mass spectrum: calculated for $C_{20}H_{19}Cl_2N_3O_2$ 403.1. found 404.1 (M$^+$+1).

Example 2

The products shown in the Table 2 below were prepared using the same procedure given in Example 1 except different acylation reagents were used in Step 2 of Example 1. Also, instead of using (R)-1-(3-chlorophenyl)ethanamine in Step 3, (R)-1-phenylethanamine was used for compounds 5-28, and in compound 29 (R)-1-(naphthalen-1-yl)ethanamine was used. In the case of compound 22, no base was added in the acylation step.

TABLE 2

| Comp | Structure | Name | m/z | Acylation Reagent |
|---|---|---|---|---|
| 5 | 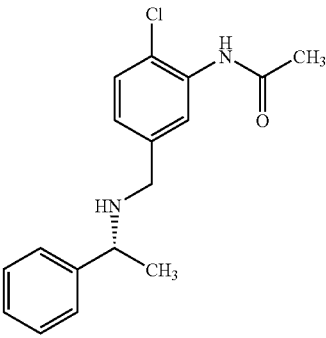 [SMILES: CC(=O)Nc1cc(CN[C@H](C)c2ccccc2)ccc1Cl] | N-(2-chloro-5-((((1R)-1-phenylethyl)amino)methyl)phenyl)acetamide | 303.2 | acyl chloride |
| 6 | 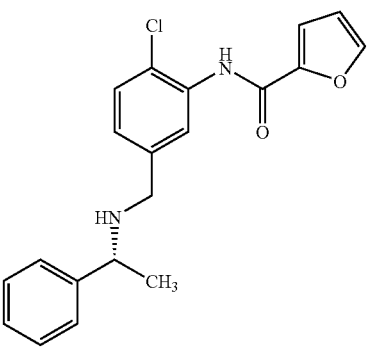 [SMILES: C[C@@H](NCc1ccc(Cl)c(NC(=O)c2ccco2)c1)c1ccccc1] | N-(2-chloro-5-((((1R)-1-phenylethyl)amino)methyl)phenyl)-2-furancarboxamide | 355.2 | furan-2-carbonyl chloride |
| 7 | 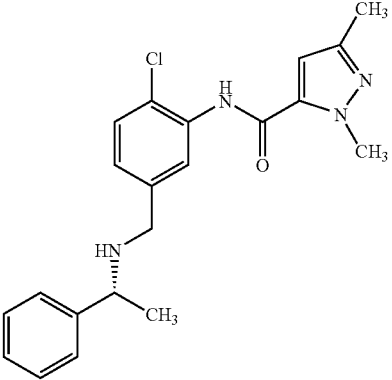 [SMILES: Cc1cc(C(=O)Nc2cc(CN[C@H](C)c3ccccc3)ccc2Cl)n(C)n1] | N-(2-chloro-5-((((1R)-1-phenylethyl)amino)methyl)phenyl)-1,3-dimethyl-1H-pyrazole-5-carboxamide | 383.2 | 1,3-dimethyl-1H-pyrazole-5-carbonyl chloride |

TABLE 2-continued

| Comp | Structure | Name | m/z | Acylation Reagent |
|---|---|---|---|---|
| 8 | 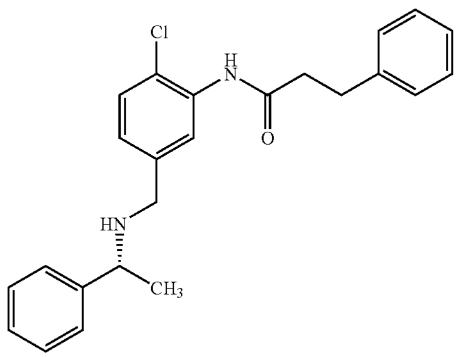 [SMILES: C[C@@H](NCc1ccc(Cl)c(NC(=O)CCc2ccccc2)c1)c1ccccc1] | N-(2-chloro-5-((((1R)-1-phenylethyl)amino)methyl)-phenyl)-3-phenylpropanamide | 393.2 | 3-phenylpropanoyl chloride |
| 9 | 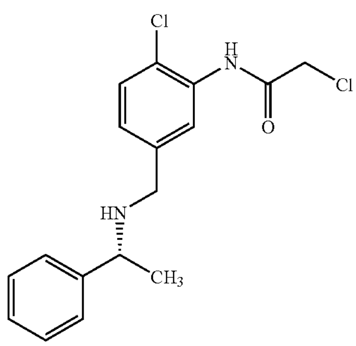 [SMILES: C[C@@H](NCc1ccc(Cl)c(NC(=O)CCl)c1)c1ccccc1] | 2-chloro-N-(2-chloro-5-((((1R)-1-phenylethyl)amino)methyl)-phenyl)acetamide | 337.1 | 2-chloroacetyl chloride |
| 10 | 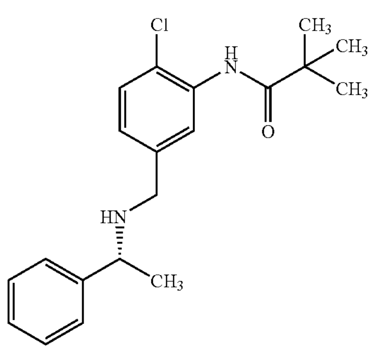 [SMILES: C[C@@H](NCc1ccc(Cl)c(NC(=O)C(C)(C)C)c1)c1ccccc1] | N-(2-chloro-5-((((1R)-1-phenylethyl)amino)methyl)-phenyl)-2,2-dimethylpropanamide | 345.2 | pivaloyl chloride |
| 11 | 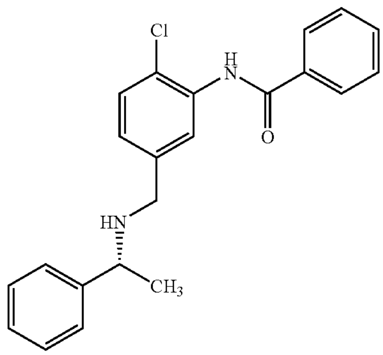 [SMILES: C[C@@H](NCc1ccc(Cl)c(NC(=O)c2ccccc2)c1)c1ccccc1] | N-(2-chloro-5-((((1R)-1-phenylethyl)amino)methyl)-phenyl)benzamide | 365.2 | benzoyl chloride |

TABLE 2-continued

| Comp | Structure | Name | m/z | Acylation Reagent |
|---|---|---|---|---|
| 12 | 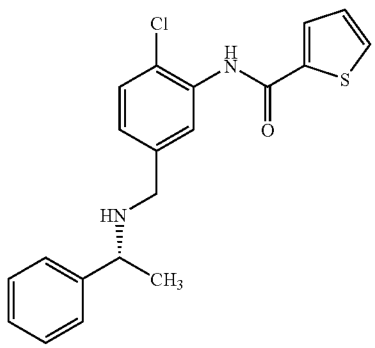 [SMILES: C[C@@H](NCc1ccc(Cl)c(NC(=O)c2cccs2)c1)c1ccccc1] | N-(2-chloro-5-((((1R)-1-phenylethyl)amino)methyl)-phenyl)-2-thiophenecarboxamide | 371.2 | thiophene-2-carbonyl chloride |
| 13 | 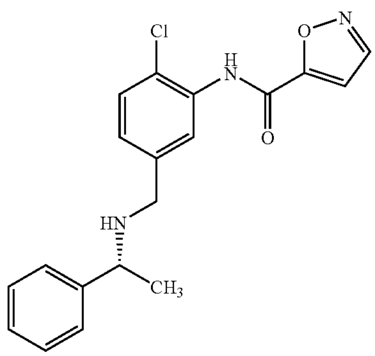 [SMILES: C[C@@H](NCc1ccc(Cl)c(NC(=O)c2ccno2)c1)c1ccccc1] | N-(2-chloro-5-((((1R)-1-phenylethyl)amino)methyl)-phenyl)-5-isoxazolecarboxamide | 356.1 | isoxazole-5-carbonyl chloride |
| 14 | 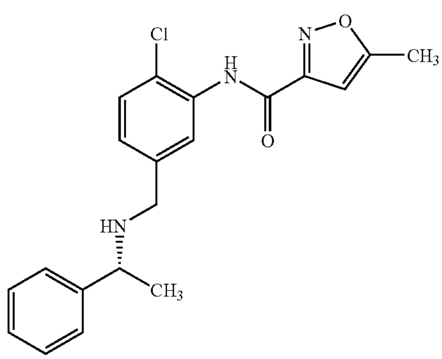 [SMILES: Cc1cc(C(=O)Nc2cc(CN[C@H](C)c3ccccc3)ccc2Cl)no1] | N-(2-chloro-5-((((1R)-1-phenylethyl)amino)methyl)-phenyl)-5-methyl-3-isoxazolecarboxamide | 370.2 | 5'-methylisoxazole-3-carbonyl chloride |
| 15 | 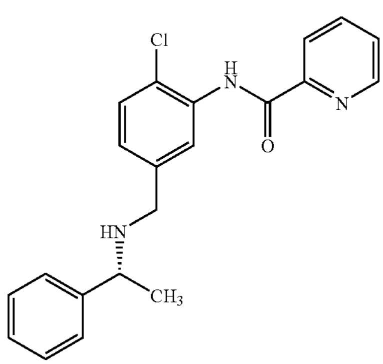 [SMILES: C[C@@H](NCc1ccc(Cl)c(NC(=O)c2ccccn2)c1)c1ccccc1] | N-(2-chloro-5-((((1R)-1-phenylethyl)amino)methyl)-phenyl)-2-pyridinecarboxamide | 366.2 | picolinoyl chloride |

TABLE 2-continued

| Comp | Structure | Name | m/z | Acylation Reagent |
|---|---|---|---|---|
| 16 | 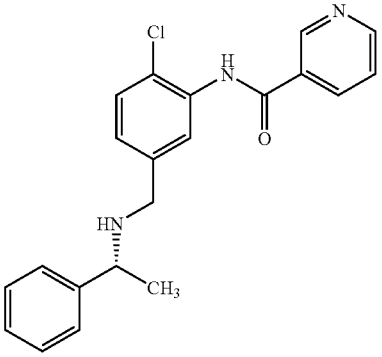 [SMILES: C[C@@H](NCc1ccc(Cl)c(NC(=O)c2cccnc2)c1)c1ccccc1] | N-(2-chloro-5-((((1R)-1-phenylethyl)amino)methyl)-phenyl)-3-pyridinecarboxamide | 366.2 | nicotinoyl chloride |
| 17 | 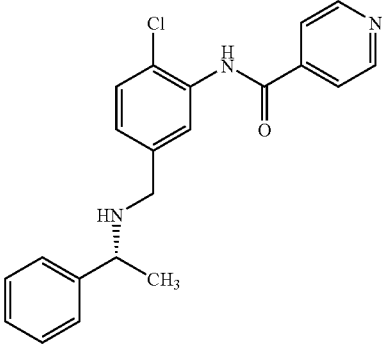 [SMILES: C[C@@H](NCc1ccc(Cl)c(NC(=O)c2ccncc2)c1)c1ccccc1] | N-(2-chloro-5-((((1R)-1-phenylethyl)amino)methyl)-phenyl)-4-pyridinecarboxamide | 366.2 | isonicotinoyl chloride |
| 18 | 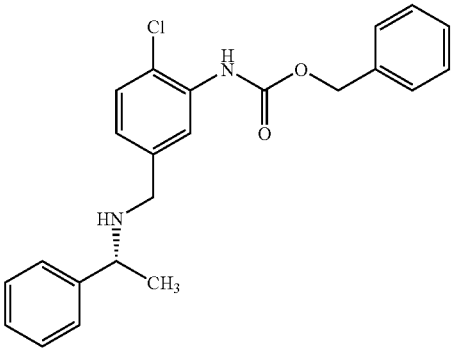 [SMILES: C[C@@H](NCc1ccc(Cl)c(NC(=O)OCc2ccccc2)c1)c1ccccc1] | phenylmethyl (2-chloro-5-((((1R)-1-phenylethyl)amino)methyl)-phenyl)carbamate | 395.2 | benzyl carbonochloridate |
| 19 | 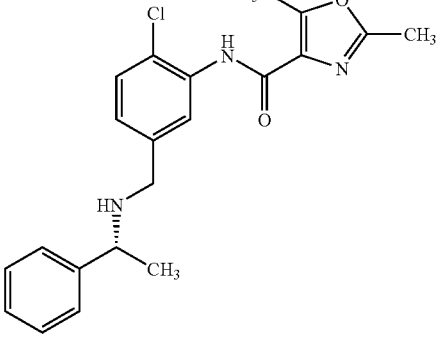 | N-(2-chloro-5-((((1R)-1-phenylethyl)amino)methyl)-phenyl)-2,5-dimethyl-1,3-oxazole-4-carboxamide | 384.2 | 2,5-dimethyloxazole-4-carbonyl chloride |

TABLE 2-continued

| Comp | Structure | Name | m/z | Acylation Reagent |
|---|---|---|---|---|
| 20 | 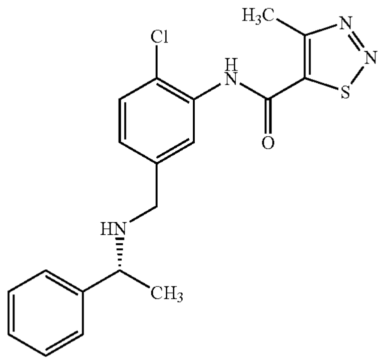 [SMILES: Cc1nnsc1C(=O)Nc1cc(CN[C@H](C)c2ccccc2)ccc1Cl] | N-(2-chloro-5-((((1R)-1-phenylethyl)amino)methyl)-phenyl)-4-methyl-1,2,3-thiadiazole-5-carboxamide | 387.1 | 4-methyl-1,2,3-thiadiazole-5-carbonyl chloride |
| 21 | 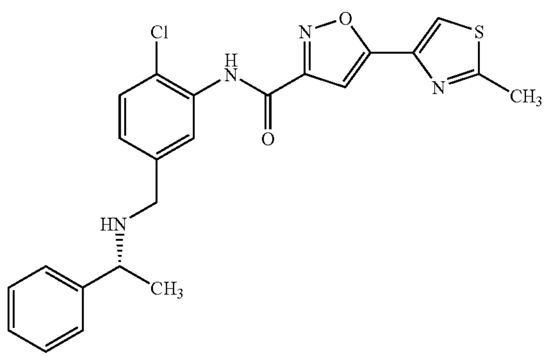 [SMILES: Cc1nc(-c2cc(C(=O)Nc3cc(CN[C@H](C)c4ccccc4)ccc3Cl)no2)cs1] | N-(2-chloro-5-((((1R)-1-phenylethyl)amino)methyl)-phenyl)-5-(2-methyl-1,3-thiazol-4-yl)-3-isoxazolecarboxamide | 453.1 | 5-(2-methylthiazol-4-yl)isoxazole-3-carbonyl chloride |
| 22 | 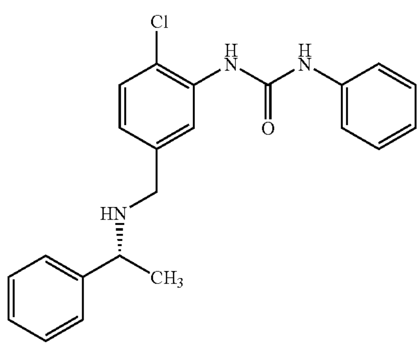 [SMILES: C[C@@H](NCc1ccc(Cl)c(NC(=O)Nc2ccccc2)c1)c1ccccc1] | N-(2-chloro-5-((((1R)-1-phenylethyl)amino)methyl)-phenyl)-N'-phenylurea | 380.2 | 1-isocyanato-benzene |
| 23 | 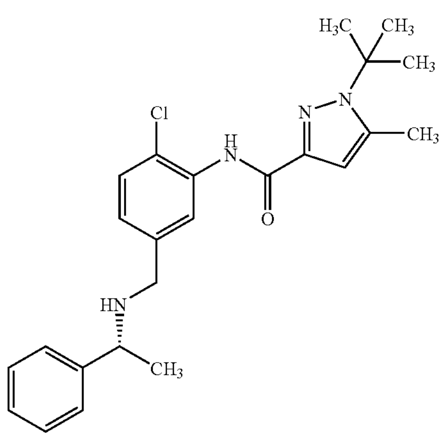 [SMILES: Cc1cc(C(=O)Nc2cc(CN[C@H](C)c3ccccc3)ccc2Cl)nn1C(C)(C)C] | N-(2-chloro-5-((((1R)-1-phenylethyl)amino)methyl)-phenyl)-1-(1,1-dimethylethyl)-5-methyl-1H-pyrazole-3-carboxamide | 425.2 | 1-tert-butyl-5-methyl-1H-pyrazole-3-carbonyl chloride |

TABLE 2-continued

| Comp | Structure | Name | m/z | Acylation Reagent |
|---|---|---|---|---|
| 24 | 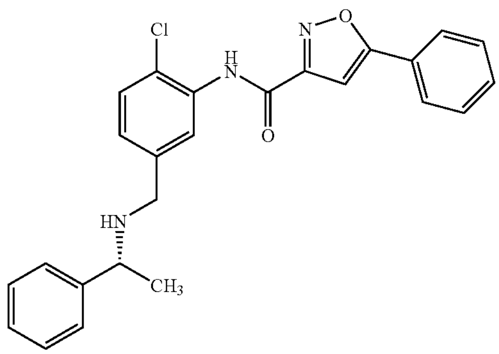 [SMILES: C[C@@H](NCc1ccc(Cl)c(NC(=O)c2cc(-c3ccccc3)on2)c1)c1ccccc1] | N-(2-chloro-5-((((1R)-1-phenylethyl)amino)methyl)-phenyl)-5-phenyl-3-isoxazolecarboxamide | 432.2 | 5-phenylisoxazole-3-carbonyl chloride |
| 25 | 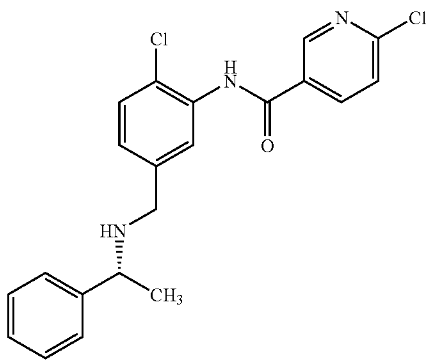 [SMILES: C[C@@H](NCc1ccc(Cl)c(NC(=O)c2ccc(Cl)nc2)c1)c1ccccc1] | 6-chloro-N-(2-chloro-5-((((1R)-1-phenylethyl)amino)methyl)-phenyl)-3-pyridinecarboxamide | 400.1 | 6-chloronicotinoyl chloride |
| 26 | 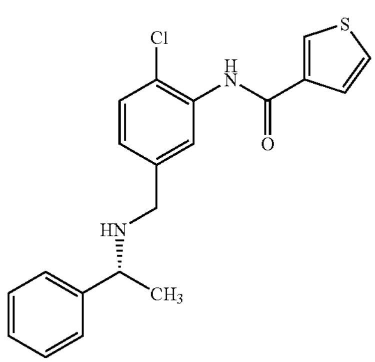 [SMILES: C[C@@H](NCc1ccc(Cl)c(NC(=O)c2ccsc2)c1)c1ccccc1] | N-(2-chloro-5-((((1R)-1-phenylethyl)amino)methyl)-phenyl)-3-thiophenecarboxamide | 371.2 | thiophene-3-carbonyl chloride |
| 27 | 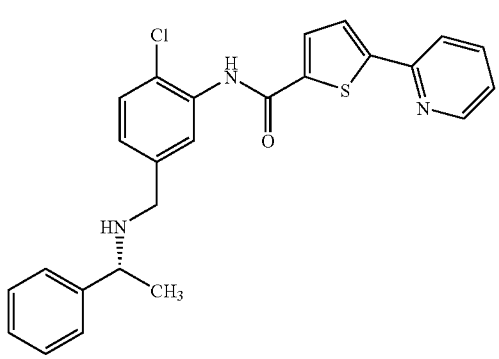 [SMILES: C[C@@H](NCc1ccc(Cl)c(NC(=O)c2ccc(-c3ccccn3)s2)c1)c1ccccc1] | N-(2-chloro-5-((((1R)-1-phenylethyl)amino)methyl)-phenyl)-5-(2-pyridinyl)-2-thiophenecarboxamide | 448.1 | 5-(pyridin-2-yl)thiophene-2-carbonyl chloride |

TABLE 2-continued

| Comp | Structure | Name | m/z | Acylation Reagent |
|---|---|---|---|---|
| 28 | 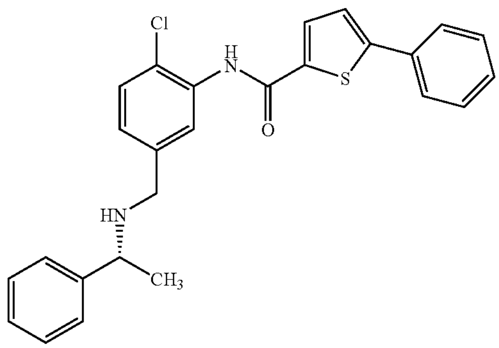 [SMILES: C[C@@H](NCc1ccc(Cl)c(NC(=O)c2ccc(-c3ccccc3)s2)c1)c1ccccc1] | N-(2-chloro-5-((((1R)-1-phenylethyl)amino)methyl)-phenyl)-5-phenyl-2-thiophenecarboxamide | 448.1 | 5-phenylthiophene-2-carbonyl chloride |
| 29 | 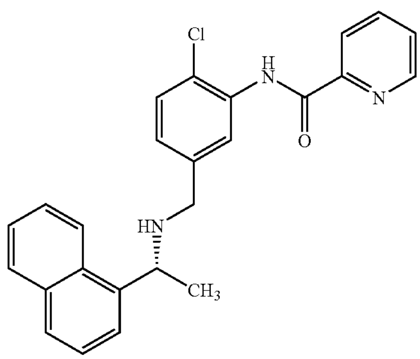 [SMILES: C[C@@H](NCc1ccc(Cl)c(NC(=O)c2ccccn2)c1)c1cccc2ccccc12] | N-(2-chloro-5-((((1R)-1-(1-naphthalenyl)ethyl)amino)methyl)-phenyl)-2-pyridinecarboxamide | 416.2 | picolinoyl chloride |

Example 3

Synthesis of (R)—N-(4-Chloro-3-nitrobenzyl)-1-(3-chlorophenyl)ethanamine (30)

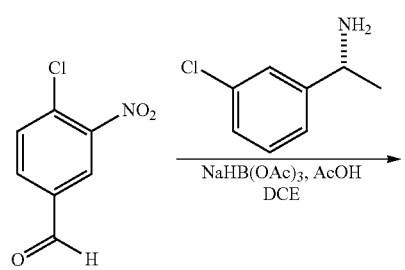

To a solution of 4-chloro-3-nitrobenzaldehyde 1 (1.71 g, 9.2 mmol) and (R)-1-(3-chlorophenyl)ethanamine (1.115 g, 7.2 mmol) in DCE (15 mL) at room temperature was added acetic acid (2.0 mL, 35 mmol) and NaBH(OAc)$_3$ (2.23 g, 11 mmol). The reaction mixture was stirred at room temperature for 2 d, quenched with saturated NaHCO$_3$, and diluted with EtOAc. The organic phase was washed with NaHCO$_3$ (1×), brine (1×), dried over MgSO$_4$, filtered, and concentrated in vacuo. Purification by flash column chromatography on silica gel (eluted with 10% to 40% EtOAc in hexanes) gave (R)—N-(4-chloro-3-nitrobenzyl)-1-(3-chlorophenyl)ethanamine 30 (2.03 g, 87% yield) as a pale yellow oil. $^1$H NMR (400 MHz, CDCl$_3$) δ 1.37 (d, J=6.7 Hz, 3H), 3.66 (s, 2H), 3.77 (q, J=6.7 Hz, 1H), 7.18-7.32 (m, 5H), 7.44-7.48 (m, 2H), 7.83 (s, 1H). Mass spectrum: calculated for C$_{15}$H$_{14}$Cl$_2$N$_2$O$_2$ 324.0. found 325.1 (M$^+$+1).

Example 4

Synthesis of (R)—N-(4-Chloro-3-(phenylthio)benzyl)-1-(3-chlorophenyl)ethanamine

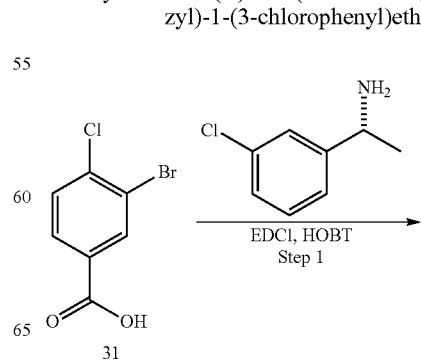

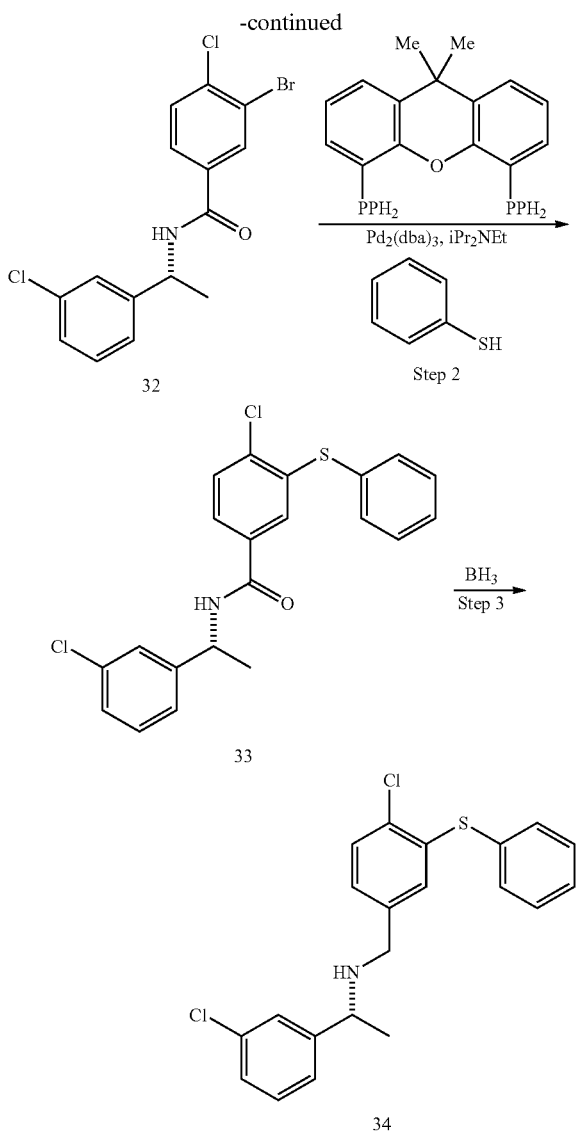

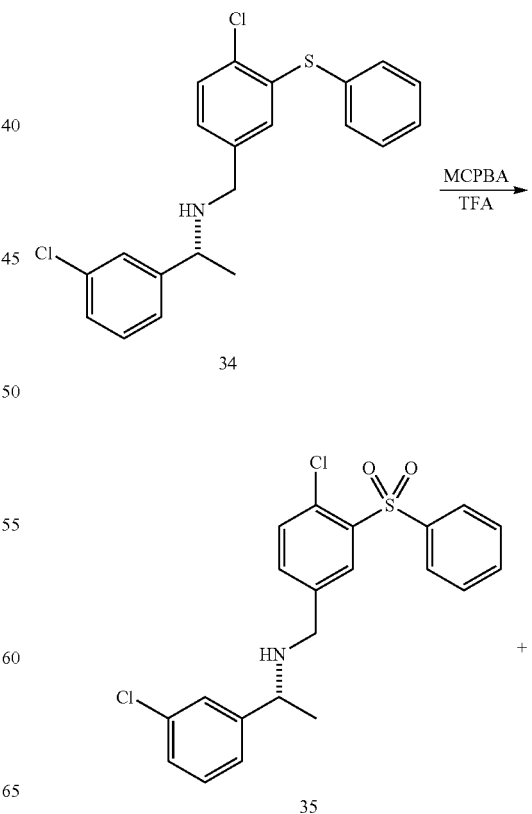

reflux. After 18 h, the reaction mixture was diluted with EtOAc, washed with water (1×), brine (1×), dried over MgSO$_4$, filtered, and concentrated in vacuo. Purification by flash column chromatography on silica gel (eluted with 5% to 30% EtOAc in hexanes) gave (R)-4-chloro-N-(1-(3-chlorophenyl)ethyl)-3-(phenylthio)benzamide 33 (0.631 g, 92% yield) as a white solid. Mass spectrum: calculated for C21H17Cl2NOS 401.0. found 402.1 (M++1).

Step 3. To a solution of (R)-4-chloro-N-(1-(3-chlorophenyl)ethyl)-3-(phenylthio)benzamide 33 (0.631 g, 1.57 mmol) in THF (8 mL) was added borane (0.110 g, 7.95 mmol) (8 mL, 1 M in THF). The reaction mixture was heated to reflux for 2 d, quenched with 1 M NaOH, and diluted with EtOAc. The organic phase was washed with water (1×), brine (1×), dried over MgSO$_4$, filtered, and concentrated in vacuo. Purification by flash column chromatography on silica gel (eluted with 20% to 50% EtOAc in hexanes) gave (R)—N-(4-chloro-3-(phenylthio)benzyl)-1-(3-chlorophenyl)ethanamine 34 (0.274 g, 45.0% yield) as a colorless oil. $^1$H NMR (400 MHz, CDCl$_3$) δ 1.26 (d, J=6.5 Hz, 3H), 3.41 (d, J=13.7 Hz, 1H), 3.50 (d, J=13.7 Hz, 1H), 3.65 (q, J=6.7 Hz, 3H), 6.93 (s, 1H), 7.05-7.09 (m, 2H), 7.20-7.25 (m, 2H), 7.37-7.43 (m, 6H). Mass spectrum: calculated for C$_{15}$H$_{14}$Cl$_2$NS 387.1. found 388.1 (M$^+$+1).

Example 5

Synthesis of (R)—N-(4-chloro-3-(phenylsulfonyl)benzyl)-1-(3-chlorophenyl)ethanamine Step 1. To a solution of 3-bromo-4-chlorobenzoic acid 31 (4.209 g, 17.9 mmol) in DMF (40 mL) at room temperature was added HOBT (3.31 g, 21.6 mmol) and EDCI (4.13 g, 21.5 mmol). The solution was stirred for 15 min and (R)-1-(3-chlorophenyl)ethanamine (2.92 g, 18.8 mmol) was added. The reaction mixture was stirred at room temperature for 14 h and diluted with EtOAc. The aqueous phase was extracted with EtOAc (1×), and the combined organic extracts were washed with water (2×), brine, dried over MgSO$_4$, filtered, and concentrated in vacuo. Purification by flash column chromatography on silica gel (eluted with 20% to 40% EtOAc in hexanes) gave (R)-3-bromo-4-chloro-N-(1-(3-chlorophenyl)ethyl)benzamide 32 (6.659 g, 99.9% yield) as a white solid. Mass spectrum: calculated for C$_{15}$H$_{12}$BrCl$_2$NO 371.0. found 372.0 (M$^+$+1).

Step 2. To a mixture of (R)-3-bromo-4-chloro-N-(1-(3-chlorophenyl)ethyl)benzamide 32 (0.634 g, 1.7 mmol), Pd2(dba)$_3$ (0.100 g, 0.11 mmol), and 4,5-bis(diphenylphosphino)-9,9-dimethyl-9H-xanthene (0.125 g, 0.22 mmol) was added benzenethiol (0.173 mL, 1.7 mmol), dioxane (4.5 mL) and N-ethyl-N-isopropylpropan-2-amine (0.590 mL, 3.4 mmol). The reaction mixture was degassed and heated to -continued

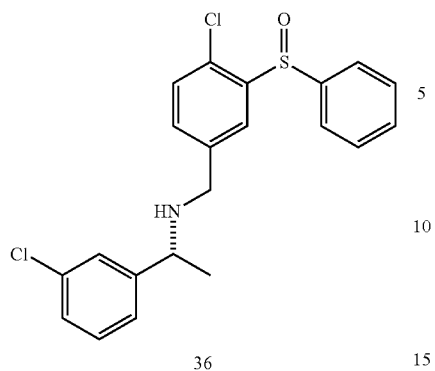

36

To a solution of (R)—N-(4-chloro-3-(phenylthio)benzyl)-1-(3-chlorophenyl)ethanamine 34 (0.259 g, 0.667 mmol) in $CH_2Cl_2$ (5 mL) at 0° C. was added 2,2,2-trifluoroacetic acid (0.300 mL, 4.04 mmol) and (R)—N-(4-chloro-3-(phenylthio)benzyl)-1-(3-chlorophenyl)ethanamine (0.259 g, 0.667 mmol). The reaction mixture was stirred at 0° C. for 1 h, additional mCPBA (114 mg, 0.66 mmol) was added, and stirring was continued at 0° C. for 30 min. The reaction mixture was warmed to room temperature and stirred for 2 h, quenched with saturated $Na_2SO_3$, and diluted with EtOAc. The organic phase was washed with saturated $NaHCO_3$ (1×), brine (1 x), dried over $MgSO_4$, filtered, and concentrated in vacuo. Purification by flash column chromatography on silica gel (eluted with 20% to 80% EtOAc in hexanes) gave (R)—N-(4-chloro-3-(phenylsulfonyl)benzyl)-1-(3-chlorophenyl)ethanamine 35 (0.113 g, 40.3% yield) as a colorless oil. 1H NMR (400 MHz, $CDCl_3$) δ 1.38 (d, J=6.4 Hz, 3H), 3.70 (s, 2H), 3.78 (q, J=6.4 Hz, 1H), 7.21-7.30 (m, 4H), 7.35 (d, J=8.0 Hz, 2H), 7.45-7.53 (m, 3H), 7.60 (t, J=7.4 Hz, 1H), 7.95 (d, J=7.2 Hz, 2H), 8.27 (s, 1H). Mass spectrum: calculated for $C_{21}H_{19}Cl_2NO_2S$ 419.1. found 420.1 (M++1). In addition, (1R)—N-(4-chloro-3-(phenylsulfinyl)benzyl)-1-(3-chlorophenyl)ethanamine 36 (0.112 g, 41.5% yield) was isolated as a colorless oil. 1H NMR (400 MHz, $CDCl_3$) δ 1.36 (d, J=6.5 Hz, 3H), 3.69-3.75 (m, 3H), 7.20-7.47 (m, 10H), 7.72-7.75 (m, 2H), 7.95 (s, 1H). Mass spectrum: calculated for $C_{21}H_{19}Cl_2NOS$ 403.1. found 404.1 (M++1).

Example 6

Synthesis of (R)-2-Chloro-5-((1-(3-chlorophenyl)ethylamino)methyl)benzenesulfonamide

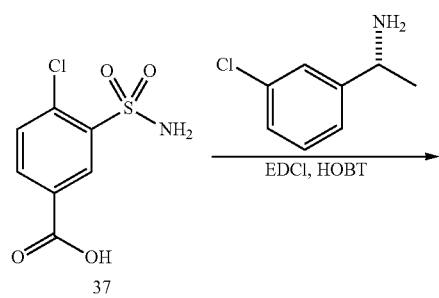

-continued

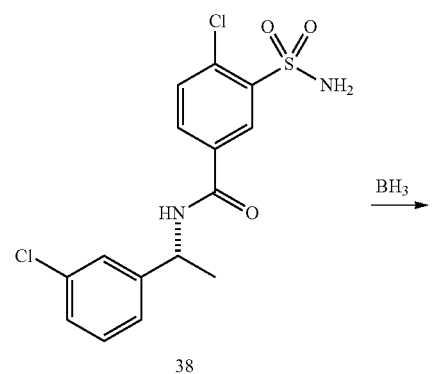

38

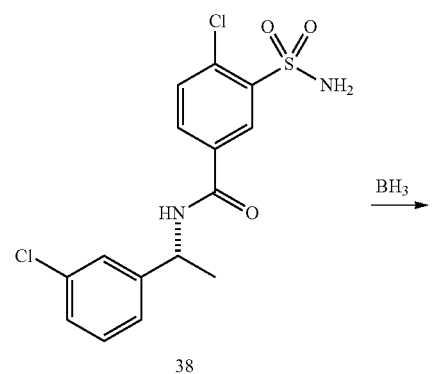

39

Step 1. To a solution of (R)-1-(3-chlorophenyl)ethanamine (0.426 g, 2.74 mmol) and 4-chloro-3-sulfamoylbenzoic acid 37 (0.452 g, 1.92 mmol) in DMF (5 mL) at room temperature was added EDCI (0.439 g, 2.29 mmol) and HOBT (0.368 g, 2.40 mmol). The reaction mixture was stirred at room temperature for 16 h, and diluted with EtOAc and water. The organic phase was washed with water (2×), brine (1×), dried over $MgSO_4$, filtered, and concentrated in vacuo. Purification by flash column chromatography on silica gel (eluted with 50% to 80% EtOAc in hexanes) yielded 3-(aminosulfonyl)-4-chloro-N-((1R)-1-(3-chlorophenyl)ethyl)benzamide 38 (0.643 g, 89.8% yield) as a white solid. Mass spectrum: calculated for $C_{15}H_{14}Cl_2N_2O_3S$ 372.0. found 373.1 (M++1).

Step 2. To a solution of 3-(aminosulfonyl)-4-chloro-N-((1R)-1-(3-chlorophenyl)ethyl)benzamide 38 (0.558 g, 1.49 mmol) in THF (10 mL) at room temperature was added borane (0.138 g, 9.97 mmol) (10 mL, 1 M in THF). The reaction mixture was heated to reflux for 24 h, quenched with 1 M NaOH, and diluted with EtOAc. The organic phase was washed with water (1×), brine (1×), dried over $MgSO_4$, filtered, and concentrated in vacuo. Purification by flash column chromatography on silica gel (eluted with 40% to 80% EtOAc in hexanes) gave (R)-2-chloro-5-((1-(3-chlorophenyl)ethylamino)methyl)benzenesulfonamide 39 (0.210 g, 39.1% yield) as a white solid. $^1$H NMR (400 MHz, $CDCl_3$) δ 1.36 (d, J=6.5 Hz, 3H), 3.64 (s, 2H), 3.76 (q, J=6.6 Hz, 1H), 5.20 (s br, 2H), 7.19-7.31 (m, 5H), 7.44-7.46 (m, 2H), 8.01 (s, 1H). Mass spectrum: calculated for $C_{15}H_{16}Cl_2N_2O_2S$ 358.0. found 359.1 (M++1).

Example 7

Synthesis of (R)—N-(4-Methoxy-3-(morpholinosulfonyl)benzyl)-1-(3-chlorophenyl)ethanamine

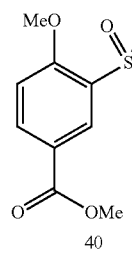 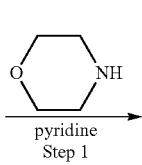

40

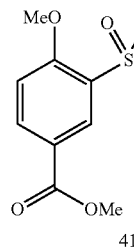 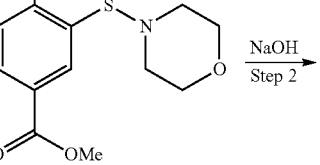

41

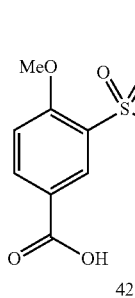 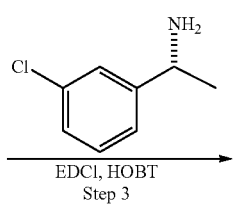

42

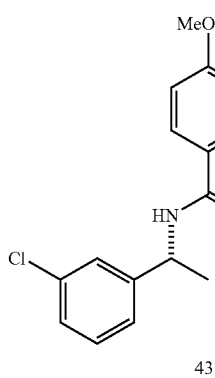 

43

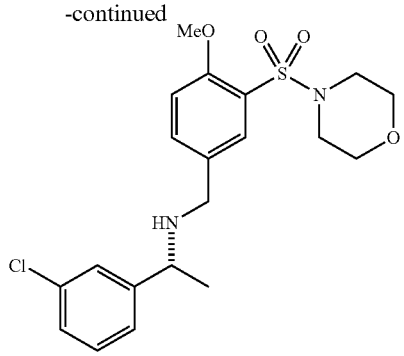

44

Step 1. To a solution of methyl 3-(chlorosulfonyl)-4-methoxybenzoate 40 (1.002 g, 3.8 mmol) in CH$_2$Cl$_2$ (20 mL) at 0° C. was added pyridine (0.46 mL, 6 mmol) and morpholine (0.395 mL, 5 mmol). The reaction mixture was warmed to room temperature, stirred for 30 min, and diluted with EtOAc. The organic phase was washed with NaHCO$_3$ (1×), brine (1×), dried over MgSO$_4$, filtered, and concentrated in vacuo. Purification by flash column chromatography on silica gel (eluted with 0% to 20% EtOAc in CH$_2$Cl$_2$) gave methyl 4-methoxy-3-(morpholinosulfonyl)benzoate 41 (0.970 g, 81% yield) as a white solid. Mass spectrum: calculated for C$_{13}$H$_{17}$NO$_6$S 315.1. found 316.1 (M++1).

Step 2. To methyl 4-methoxy-3-(morpholinosulfonyl)benzoate 41 (0.970 g, 3.08 mmol) was added NaOH (0.599 g, 15.0 mmol) (15 mL, 1 M in water) followed by methanol (10 mL). The reaction mixture was heated to 60° C. for 2 h and acidified with 1 M HCl. The organic phase was extracted with EtOAc (5×) and the combined extracts were washed with brine (1×), dried over MgSO$_4$, filtered, and concentrated to yield 4-methoxy-3-(morpholinosulfonyl)benzoic acid 42 (0.824 g, 88.9% yield) as a white solid which was used without further purification. Mass spectrum: calculated for C$_{12}$H$_{15}$NO$_6$S 301.1. found 302.1 (M++1).

Step 3. To a solution of 4-methoxy-3-(morpholinosulfonyl)benzoic acid 42 (0.824 g, 2.73 mmol) in DMF (6 mL) was added EDCI (0.686 g, 3.58 mmol) and HOBT (0.536 g, 3.50 mmol), the solution was stirred for 30 min and (R)-1-(3-chlorophenyl)ethanamine (0.673 g, 4.32 mmol) was added. The reaction mixture was stirred at room temperature for 16 h and diluted with EtOAc and water. The organic phase was washed with water (2×), brine (1×), dried over MgSO$_4$, filtered, and concentrated in vacuo. Purification by flash column chromatography on silica gel (eluted with 60% to 100% EtOAc in hexanes) gave (R)—N-(1-(3-chlorophenyl)ethyl)-4-methoxy-3-(morpholinosulfonyl)benzamide 43 (1.14 g, 95.0% yield) as a white solid. Mass spectrum: calculated for C$_{20}$H$_{23}$ClN$_2$O$_5$S 438.1. found 439.1 (M$^+$+1).

Step 4. To a solution of (R)—N-(1-(3-chlorophenyl)ethyl)-4-methoxy-3-(morpholinosulfonyl)benzamide 43 (0.948 g, 2.16 mmol) in THF (9 mL) at room temperature was added borane (0.124 g, 8.96 mmol) (9 mL, 1 M in THF). The reaction mixture was heated to reflux for 24 h, quenched with 1 M NaOH, and diluted with EtOAc. The organic phase was washed with water (1×), brine (1×), dried over MgSO$_4$, filtered, and concentrated in vacuo. Purification by flash column chromatography on silica gel (eluted with 50% to 100% EtOAc in hexanes) gave (R)—N-(4-methoxy-3-(morpholinosulfonyl)benzyl)-1-(3-chlorophenyl)ethanamine 44 (0.166 g, 18.1% yield) as a colorless oil. $^1$H NMR (400 MHz, CDCl$_3$) δ 1.35 (d, J=6.5 Hz, 3H), 3.21-3.24 (m, 4H), 3.55-3.63 (m, 2H), 3.71-3.78 (m, 4H), 3.91 (s, 3H), 6.97 (d, J=8.6 Hz, 1H), 7.20-7.29 (m, 3H), 7.33 (s, 1H), 7.46 (d, J=7.9 Hz, 1H), 7.78 (s, 1H). Mass spectrum: calculated for C$_{20}$H$_{25}$ClN$_2$O$_4$S 424.1. found 425.2 (M$^+$+1).

Example 8

Synthesis of (R)—N-(4-chloro-3-(morpholinosulfonyl)benzyl)-1-(3-chlorophenyl)ethanamine

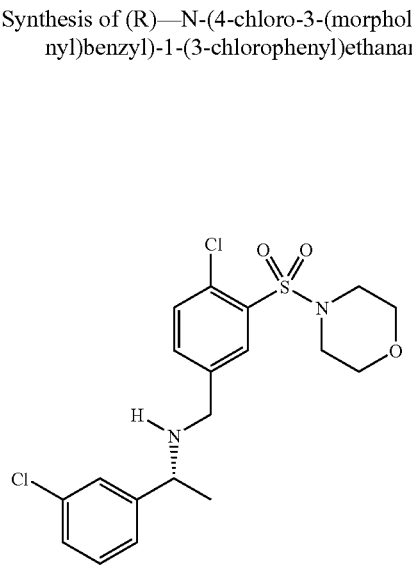

(R)—N-(4-chloro-3-(morpholinosulfonyl)benzyl)-1-(3-chlorophenyl)ethanamine 45 was obtained as a colorless oil using the procedure in Example 7 substituting methyl 3-(chlorosulfonyl)-4-methoxybenzoate for methyl 4-chloro-3-(chlorosulfonyl)benzoate. $^1$H NMR (400 MHz, CDCl$_3$) δ 1.36 (d, J=6.7 Hz, 3H), 3.26-3.30 (m, 4H), 3.65 (s, 2H), 3.71-3.78 (m, 5H), 7.19-7.29 (m, 4H), 7.32 (s, 1H), 7.44-7.48 (m, 2H), 7.94 (s, 1H). Mass spectrum: calculated for C$_{19}$H$_{22}$Cl$_2$N$_2$O$_3$S 428.1. found 429.1 (M$^+$+1).

Example 9

Synthesis of (R)—N-(2-Chloro-5-((1-phenylethylamino)methyl)phenyl)-2-(pyrrolidin-1-yl)acetamide

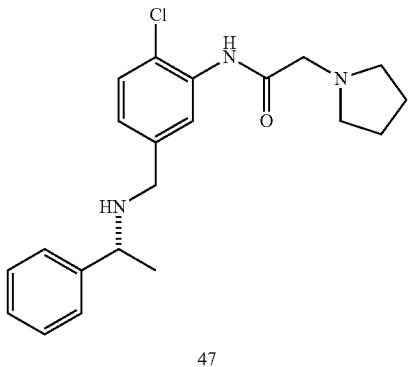

47

To a solution of (R)-2-chloro-N-(2-chloro-5-((1-phenylethylamino)methyl)phenyl)acetamide 46 (0.397 g, 1.2 mmol) in THF (6 mL) was added pyrrolidine (3.0 mL, 36 mmol). The reaction mixture was heated to 50° C. for 30 min, cooled to room temperature, partially concentrated under reduced pressure, quenched with saturated NaHCO$_3$, and diluted with EtOAc. The aqueous phase was extracted with EtOAc (3×) and the combined organic extracts were washed with brine (1×), dried over MgSO$_4$, filtered, and concentrated in vacuo. Purification by flash column chromatography on silica gel (eluted with 1% to 10% MeOH in DCM) gave (R)—N-(2-chloro-5-((1-phenylethylamino)methyl)phenyl)-2-(pyrrolidin-1-yl)acetamide 47 (0.292 g, 67% yield) as a colorless oil. 1H NMR (400 MHz, CDCl$_3$) δ 1.36 (d, J=6.5 Hz, 3H), 1.83-1.91 (m, 4H), 2.68-2.79 (m, 4H), 3.33 (s, 2H), 3.58 (d, J=13.5 Hz, 1H), 3.64 (d, J=13.3 Hz, 1H), 3.81 (q, J=6.7 Hz, 1H), 6.98 (d, J=8.2 Hz, 1H), 7.23-7.37 (m, 7H), 8.38 (s, 1H), 9.93 (s, 1H). Mass spectrum: calculated for C$_{21}$H$_{26}$ClN$_3$O 371.2. found 372.2 (M++1).

Example 10

Synthesis of (R)—N-(2-chloro-5-((1-phenylethylamino)methyl)phenyl)-6-(dimethylamino)nicotinamide

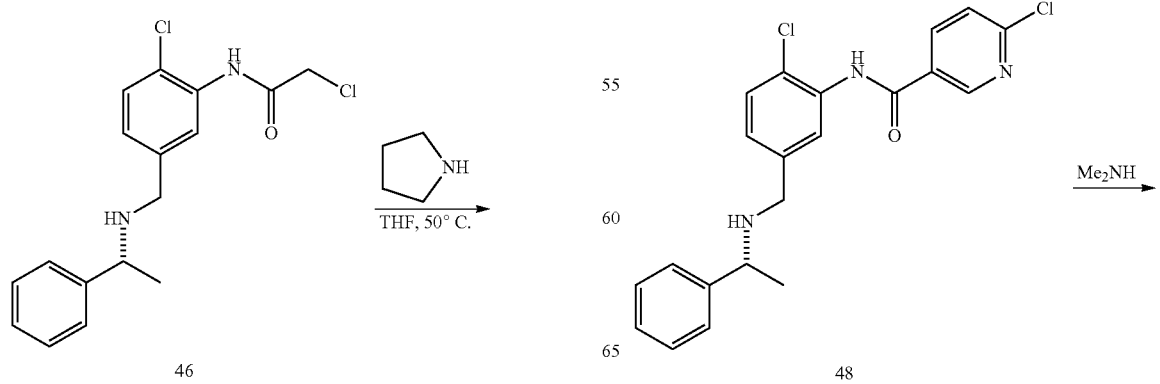

-continued

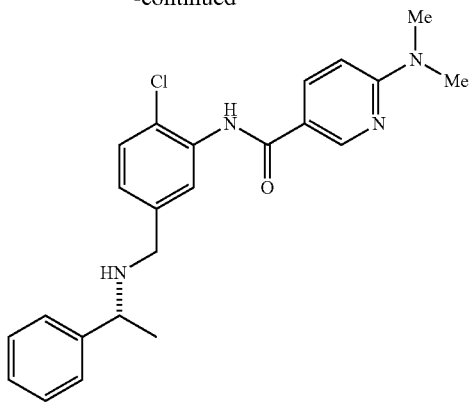

49

To a solution of (R)-6-chloro-N-(2-chloro-5-((1-phenyl-ethylamino)methyl)phenyl)nicotinamide 48 (0.175 g, 0.44 mmol) in THF (3 mL) at 0° C. was added dimethylamine (5.0 mL, 153 mmol). The reaction mixture was warmed to room temperature, stirred for 20 h, quenched with saturated NaHCO$_3$, and diluted with EtOAc. The organic phase was washed with saturated NaHCO$_3$ (1×), brine (1×), dried over MgSO$_4$, filtered, and concentrated in vacuo. Purification by flash column chromatography on silica gel (eluted with 50% to 100% EtOAc in hexanes) gave (R)—N-(2-chloro-5-((1-phenylethylamino)methyl)phenyl)-6-(dimethylamino)nicotinamide 49 (0.118 g, 66% yield) as a white solid. $^1$H NMR (400 MHz, CDCl$_3$) δ 1.37 (d, J=6.5 Hz, 3H), 3.19 (s, 6H), 3.60 (d, J=13.5 Hz, 1H), 3.66 (d, J=13.5 Hz, 1H), 3.81 (q, J=6.6 Hz, 3H), 6.57 (d, J=8.6 Hz, 1H), 7.00 (dd, J=8.2, 2.2 Hz, 1H), 7.25-7.37 (m, 7H), 8.00 (dd, J=9.0, 2.5 Hz, 1H), 8.27 (s, 1H), 8.49 (d, J=2.0 Hz, 1H), 8.76 (d, J=2.2 Hz, 1H). Mass spectrum: calculated for C$_{23}$H$_{25}$ClN$_4$O 408.2. found 409.2 (M$^+$+1).

Example 11

The compounds shown in the Table 3 were prepared using the same procedure given in Example 10 substituting dimethylamine for the corresponding amine shown in the table. In some cases heating of the reaction was required.

TABLE 3

| Comp | Structure | Name | m/z | Amine |
|---|---|---|---|---|
| 50 | 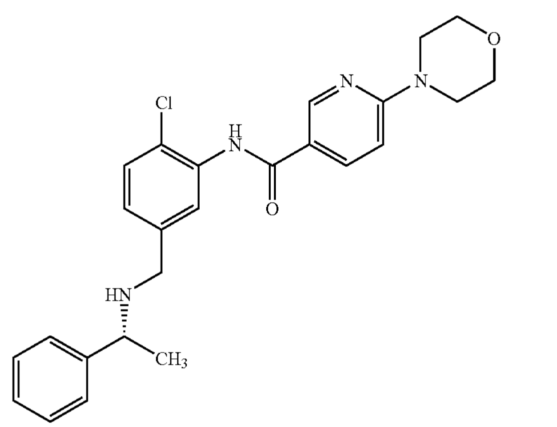 [SMILES: C[C@@H](NCc1ccc(Cl)c(NC(=O)c2ccc(N3CCOCC3)nc2)c1)c1ccccc1] | N-(2-chloro-5-((((1R)-1-phenylethyl)amino)methyl)phenyl)-6-(4-morpholinyl)-3-pyridinecarboxamide | 451.2 | morpholine |
| 51 | 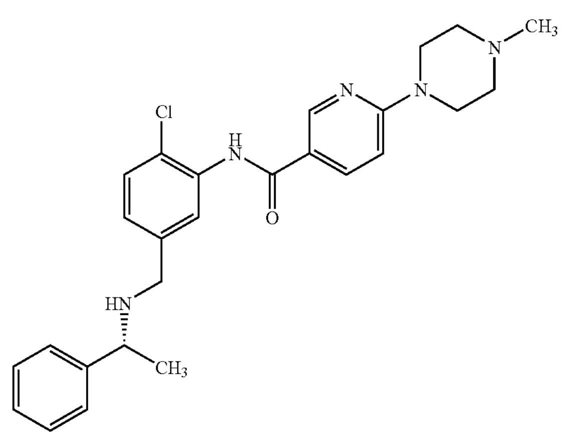 [SMILES: C[C@@H](NCc1ccc(Cl)c(NC(=O)c2ccc(N3CCN(C)CC3)nc2)c1)c1ccccc1] | N-(2-chloro-5-((((1R)-1-phenylethyl)amino)methyl)phenyl)-6-(4-methyl-1-piperazinyl)-3-pyridinecarboxamide | 464.3 | 1-methyl-piperazine |

TABLE 3-continued

| Comp | Structure | Name | m/z | Amine |
|---|---|---|---|---|
| 52 | 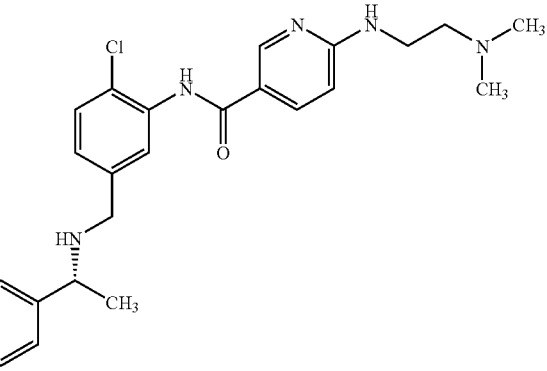 | N-(2-chloro-5-((((1R)-1-phenylethyl)amino)methyl)phenyl)-6-((2-(dimethylamino)ethyl)amino)-3-pyridinecarboxamide | 452.2 | N1,N1-dimethyl-ethane-1,2-diamine |
| 53 | 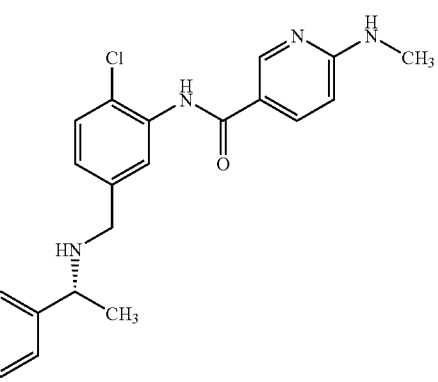 | N-(2-chloro-5-((((1R)-1-phenylethyl)amino)methyl)phenyl)-6-(methylamino)-3-pyridinecarboxamide | 395.2 | methylamine |
| 54 | 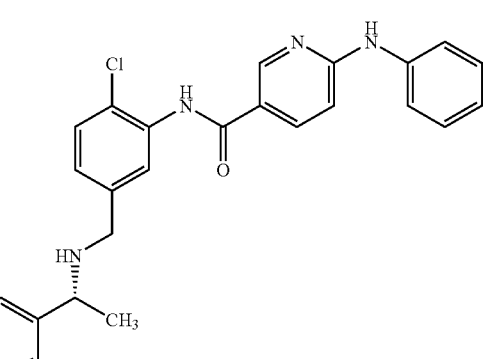 | N-(2-chloro-5-((((1R)-1-phenylethyl)amino)methyl)phenyl)-6-(phenylamino)-3-pyridinecarboxamide | 457.2 | aniline |
| 55 | 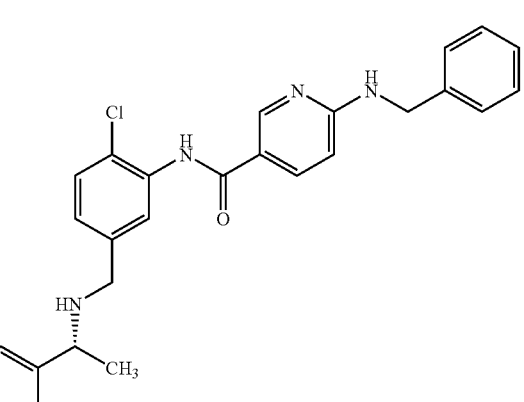 | N-(2-chloro-5-((((1R)-1-phenylethyl)amino)methyl)phenyl)-6-((phenylmethyl)amino)-3-pyridinecarboxamide | 471.2 | benzylamine |

TABLE 3-continued
| Comp | Structure | Name | m/z | Amine |
|---|---|---|---|---|
| 56 | 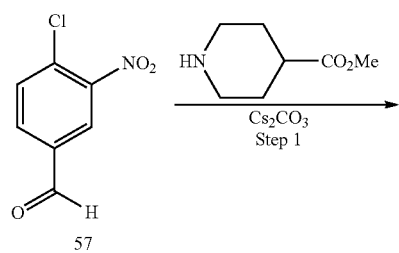 | N-(2-chloro-5-((((1R)-1-phenylethyl)amino)methyl)phenyl)-6-((2-phenylethyl)amino)-3-pyridinecarboxamide | 485.3 | 2-phenylethan-amine |
Example 12
Synthesis of (R)-1-(2-(5-methylisoxazole-3-carboxamido)-4-((1-phenylethylamino)methyl)phenyl)piperidine-4-carboxamide
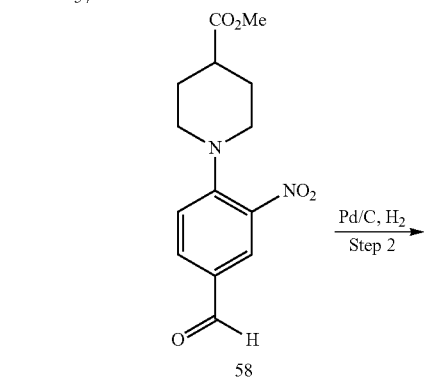
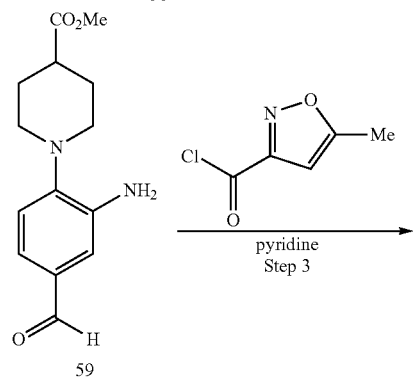
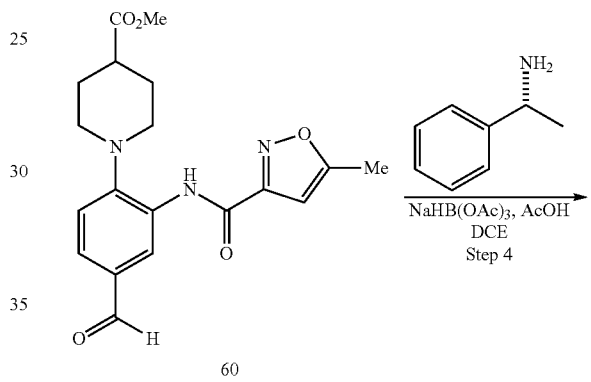

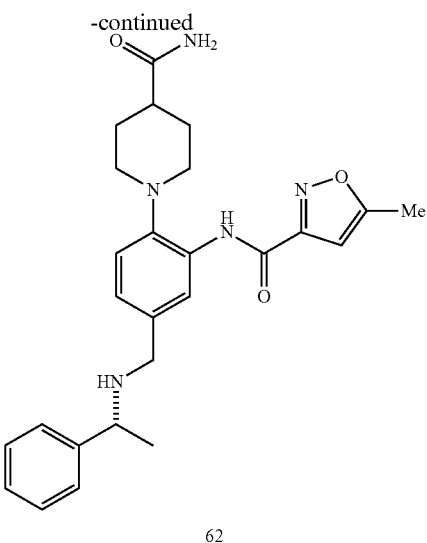

62

Step 1. To a mixture of 4-chloro-3-nitrobenzaldehyde 57 (5.099 g, 27 mmol), cesium carbonate (9.48 g, 29 mmol), and methyl piperidine-4-carboxylate (4 mL, 27 mmol) was added DMSO (27 mL). The reaction mixture was heated to 100° C. for 30 min and diluted with EtOAc. The organic phase was washed with water (2×), brine (1×), dried over MgSO$_4$, filtered, and concentrated in vacuo. Purification by flash column chromatography on silica gel (eluted with 30% to 50% EtOAc in hexanes) gave methyl 1-(4-formyl-2-nitrophenyl)piperidine-4-carboxylate 58 (3.45 g, 43% yield) as a yellow oil. Mass spectrum: calculated for $C_{14}H_{16}N_2O_5$ 292.1. found 293.1 (M$^+$+1).

Step 2. To a mixture of 10% palladium on carbon (1.67 g, 1.57 mmol) and methyl 1-(4-formyl-2-nitrophenyl)piperidine-4-carboxylate 58 (3.435 g, 11.8 mmol) was added EtOAc (100 mL). The nitrogen atmosphere was replaced by hydrogen from a double balloon and the reaction mixture was stirred at room temperature for 4 h, filtered, and concentrated in vacuo. Purification by flash column chromatography on silica gel (eluted with 20% to 60% EtOAc in hexanes) gave methyl 1-(2-amino-4-formylphenyl)piperidine-4-carboxylate 59 (0.488 g, 15.8% yield) as a yellow solid. Mass spectrum: calculated for $C_{14}H_{18}N_2O_3$ 262.1. found 263.2 (M$^+$+1).

Step 3. To a solution of methyl 1-(2-amino-4-formylphenyl)piperidine-4-carboxylate 59 (0.488 g, 1.9 mmol) in DCM (10 mL) at 0° C. was added pyridine (0.300 mL, 3.7 mmol) and 5-methylisoxazole-3-carbonyl chloride (0.185 g, 1.3 mmol). The reaction mixture was stirred at 0° C. for 30 min, additional acid chloride (88 mg) was added and stirring was continued at 0° C. After 30 min, the reaction mixture was diluted with EtOAc, washed with saturated NaHCO$_3$ (1×), brine (1×), dried over MgSO$_4$, filtered, and concentrated in vacuo. Purification by flash column chromatography on silica gel (eluted with 20% to 50% EtOAc in hexanes) gave methyl 1-(4-formyl-2-(5-methylisoxazole-3-carboxamido)phenyl)piperidine-4-carboxylate 60 (0.268 g, 39% yield) as a pale yellow solid. Mass spectrum: calculated for $C_{19}H_{21}N_3O_5$ 371.2. found 372.2 (M$^+$+1).

Step 4. To a solution of methyl 1-(4-formyl-2-(5-methylisoxazole-3-carboxamido)phenyl)piperidine-4-carboxylate 60 (0.268 g, 0.72 mmol) in DCE (10 mL) was added acetic acid (0.045 mL, 0.78 mmol), (R)-1-phenylethanamine (0.11 mL, 0.88 mmol), and NaBH(OAc)$_3$ (0.186 g, 0.88 mmol). The reaction mixture was stirred at room temperature for 15 h and diluted with EtOAc. The organic phase was washed with saturated NaHCO$_3$ (1×), brine (1×), dried over MgSO$_4$, filtered, and concentrated in vacuo. Purification by flash column chromatography on silica gel (eluted with 70% to 100% EtOAc in hexanes) gave (R)-methyl 1-(2-(5-methylisoxazole-3-carboxamido)-4-((1-phenylethylamino)methyl)phenyl)piperidine-4-carboxylate 61 (0.230 g, 67% yield) as a white solid. Mass spectrum: calculated for $C_{27}H_{32}N_4O_4$ 476.2. found 477.3 (M$^+$+1).

Step 5. To (R)-methyl 1-(2-(5-methylisoxazole-3-carboxamido)-4-((1-phenylethylamino)methyl)phenyl)piperidine-4-carboxylate 61 (0.220 g, 0.46 mmol) was added ammonia (2 M in MeOH, 50 mL). The reaction mixture was heated to 75° C. in a sealed tube for 7 d, and concentrated in vacuo. Purification by flash column chromatography on silica gel (1% to 10% MeOH (2 M NH$_3$) in DCM) gave (R)-1-(2-(5-methylisoxazole-3-carboxamido)-4-((1-phenylethylamino)methyl)phenyl)piperidine-4-carboxamide 62 (0.048 g, 23% yield) as a white solid. $^1$H NMR (400 MHz, DMSO-d$_6$) δ 1.26 (d, J=6.7 Hz, 3H), 1.76-1.84 (m, 4H), 2.24 (m, 1H), 2.52 (s, 3H), 2.67 (t, J=8.8 Hz, 2H), 2.95 (d, J=11.5 Hz, 2H), 3.43 (d, J=13.3 Hz, 1H), 3.48 (d, J=13.7 Hz, 1H), 3.71 (q, J=6.5 Hz, 1H), 6.71 (s, 1H), 7.19 (s, 1H), 7.05 (d, J=8.1 Hz, 1H), 7.20 (d, J=8.1 Hz, 1H), 7.22 (d, J=3.9 Hz, 1H), 7.31-7.38 (m, 6H), 8.22 (s, 1H), 9.73 (s, 1H). Mass spectrum: calculated for $C_{26}H_{31}N_5O_3$ 461.2. found 462.3 (M$^+$+1).

Example 13

Synthesis of (R)-1-(2-Chloro-5-((1-phenylethylamino)methyl)phenyl)piperidine-4-carboxamide

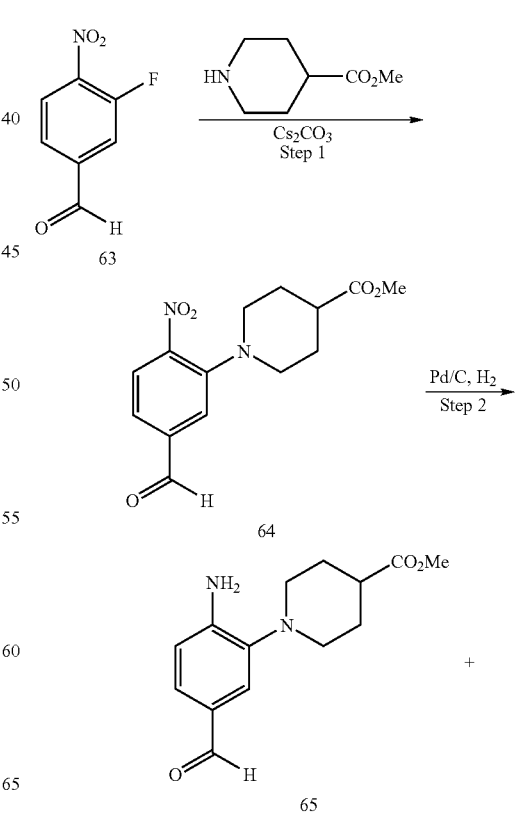

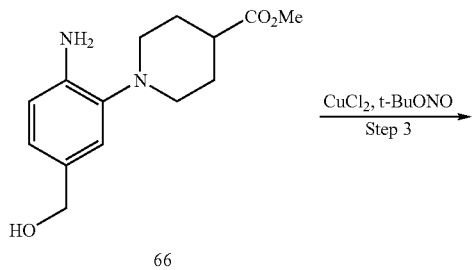

66

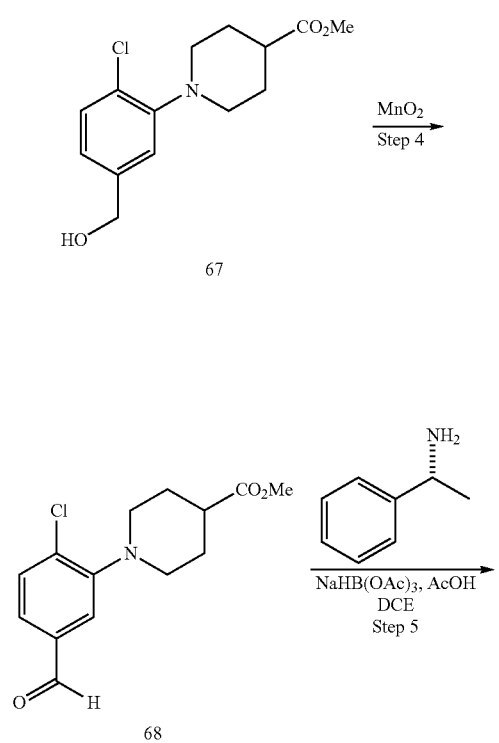

67

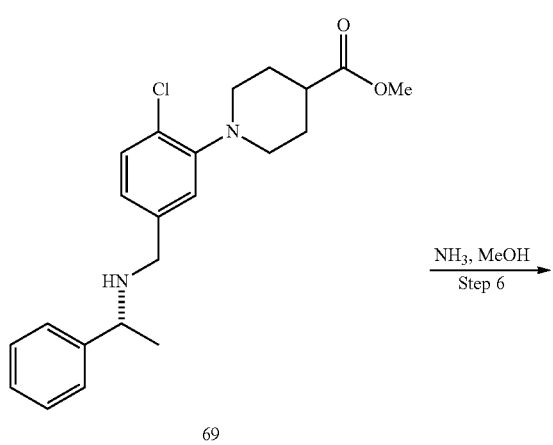

68

69

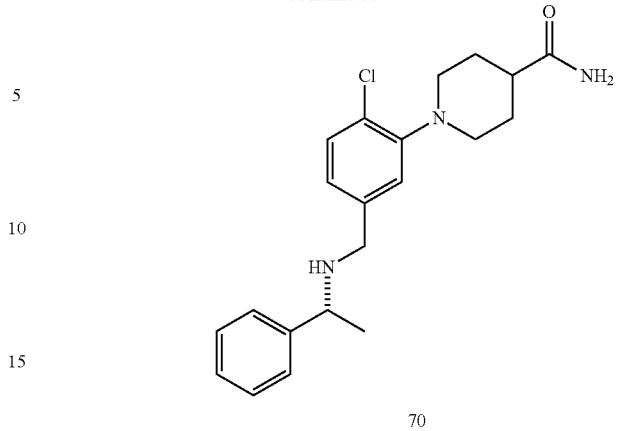

70

Step 1. To a solution of 3-fluoro-4-nitrobenzaldehyde 63 (0.793 g, 5 mmol) in DMSO (5 mL) was added methyl piperidine-4-carboxylate (0.7 mL, 5 mmol) and cesium carbonate (1.76 g, 5 mmol). The reaction mixture was stirred at room temperature for 30 min, heated to 70° C. for 2 h, and diluted with EtOAc. The organic phase was washed with water (1×), brine (1×), dried over MgSO$_4$, filtered, and concentrated in vacuo. Purification by flash column chromatography on silica gel (eluted with 30% to 60% EtOAc in hexanes) gave methyl 1-(5-formyl-2-nitrophenyl)piperidine-4-carboxylate 64 (0.931 g, 68% yield) as a yellow oil. Mass spectrum: calculated for $C_{14}H_{16}N_2O_5$ 292.1. found 293.1 (M$^+$+1).

Step 2. To methyl 1-(5-formyl-2-nitrophenyl)piperidine-4-carboxylate 64 (0.881 g, 3.0 mmol) was added EtOAc (20 mL) and palladium (0.482 mg, 0.45 mmol). The nitrogen atmosphere was replaced by hydrogen from a double balloon and the reaction mixture was stirred at room temperature for 3 h, filtered, and concentrated in vacuo. Purification by flash column chromatography on silica gel (eluted with 50% to 100% EtOAc in hexanes) gave methyl 1-(2-amino-5-formylphenyl)piperidine-4-carboxylate 65 (0.043 g, 5.4% yield) as a yellow oil. Mass spectrum: calculated for $C_{14}H_{18}N_2O_3$ 262.1. found 263.2 (M$^+$+1). In addition, methyl 1-(2-amino-5-(hydroxymethyl)phenyl)piperidine-4-carboxylate 66 (0.534 g, 67% yield) was isolated as a yellow solid. Mass spectrum: calculated for $C_{14}H_{20}N_2O_3$ 264.2. found 265.2 (M$^+$+1).

Step 3. To a suspension of CuCl$_2$ (0.321 mg, 2.39 mmol) in MeCN (4 mL) was added tert-butyl nitrite (0.356 g, 3.45 mmol). The mixture was heated to 65° C. and a solution of methyl 1-(2-amino-5-(hydroxymethyl)phenyl)piperidine-4-carboxylate 66 (0.534 g, 2.02 mmol) in MeCN (4 mL) was added via syringe. The reaction mixture was stirred for 10 min and diluted with EtOAc and water. The aqueous phase was extracted with EtOAc (2×) and the combined organic extracts were washed with brine (1×), dried over MgSO$_4$, filtered, and concentrated in vacuo. Purification by flash column chromatography on silica gel (eluted with 30% to 60% EtOAc in hexanes) gave methyl 1-(2-chloro-5-(hydroxymethyl)phenyl)piperidine-4-carboxylate 67 (0.198 g, 34.5% yield) as a colorless oil. Mass spectrum: calculated for $C_{14}H_{18}ClNO_3$ 283.1. found 284.1 (M$^+$+1).

Step 4. To a solution of methyl 1-(2-chloro-5-(hydroxymethyl)phenyl)piperidine-4-carboxylate 67 (0.198 g, 0.698 mmol) in DCM (3.5 mL) was added MnO$_2$ (0.688 mg, 7.91 mmol). The reaction mixture was stirred at room temperature for 17 h, filtered, and concentrated in vacuo. Purification by flash column chromatography on silica gel (eluted with 10% to 40% EtOAc in hexanes) gave methyl 1-(2-chloro-5-formylphenyl)piperidine-4-carboxylate 68 (0.150 g, 76.3% yield) as a colorless oil. Mass spectrum: calculated for $C_{14}H_{16}ClNO_3$ 281.1. found 282.1 (M$^+$+1).

Step 5. To a solution of methyl 1-(2-chloro-5-formylphenyl)piperidine-4-carboxylate 68 (0.180 g, 0.64 mmol) in DCE (3 mL) was added (R)-1-phenylethanamine (0.10 mL, 0.79 mmol), acetic acid (0.040 mL, 0.69 mmol), and NaBH(OAc)$_3$ (0.168 g, 0.79 mmol). The reaction mixture was stirred at room temperature for 20 h, quenched with saturated NaHCO$_3$, and diluted with EtOAc. The organic phase was washed with saturated NaHCO$_3$ (1×), brine (1 x), dried over MgSO$_4$, filtered, and concentrated in vacuo. Purification by flash column chromatography on silica gel (eluted with 50% to 100% EtOAc in hexanes) gave (R)-methyl 1-(2-chloro-5-((1-phenylethylamino)methyl)phenyl)piperidine-4-carboxylate 69 (0.215 g, 87% yield) as a colorless oil. Mass spectrum: calculated for $C_{22}H_{27}ClN_2O_2$ 386.2. found 387.2 (M$^+$+1).

Step 6. A solution of (R)-methyl 1-(2-chloro-5-((1-phenylethylamino)methyl)phenyl)piperidine-4-carboxylate 69 (0.215 g, 0.56 mmol) in MeOH (2 M NH$_3$, 75 mL) was heated to 75° C. in a sealed tube for 6 d and concentrated in vacuo. Purification by flash column chromatography on silica gel (eluted with 1% to 8% MeOH (2 M NH$_3$) in DCM) gave (R)-1-(2-chloro-5-((1-phenylethylamino)methyl)phenyl)piperidine-4-carboxamide 70 (0.074 g, 36% yield) as a colorless oil. $^1$H NMR (400 MHz, DMSO-d$_6$) δ 1.25 (d, J=6.7 Hz, 3H), 1.70-1.80 (m, 4H), 2.22 (m, 1H), 2.60 (t, J=11.3 Hz, 2H), 3.17 (d, J=5.3 Hz, 1H), 3.26 (d, J=10.1 Hz, 2H), 3.41 (d, J=13.9 Hz, 1H), 3.48 (d, J=13.9 Hz, 1H), 3.65 (q, J=6.5 Hz, 1H), 6.79 (s, 1H), 6.92 (d, J=8.0 Hz, 1H), 7.03 (s, 1H), 7.22 (t, J=6.5 Hz, 1H), 7.28-7.35 (m, 6H). Mass spectrum: calculated for $C_{21}H_{26}ClN_3O$ 371.2. found 372.2 (M$^+$+1).

Example 14

Synthesis of (R)-2-Chloro-5-((1-phenylethylamino)methyl)-N-(pyridin-2-ylmethyl)benzenamine

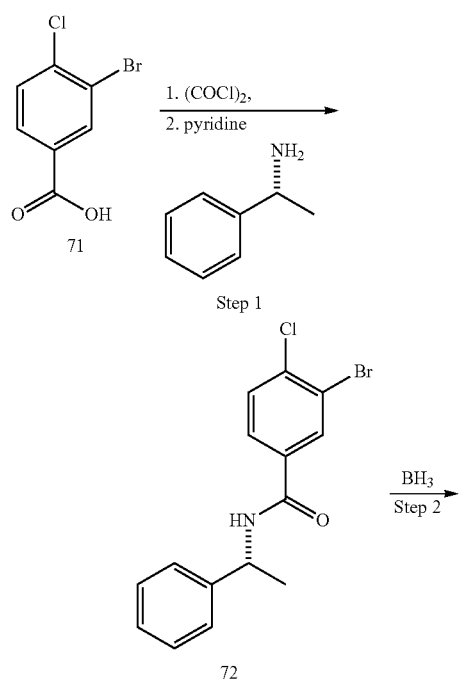

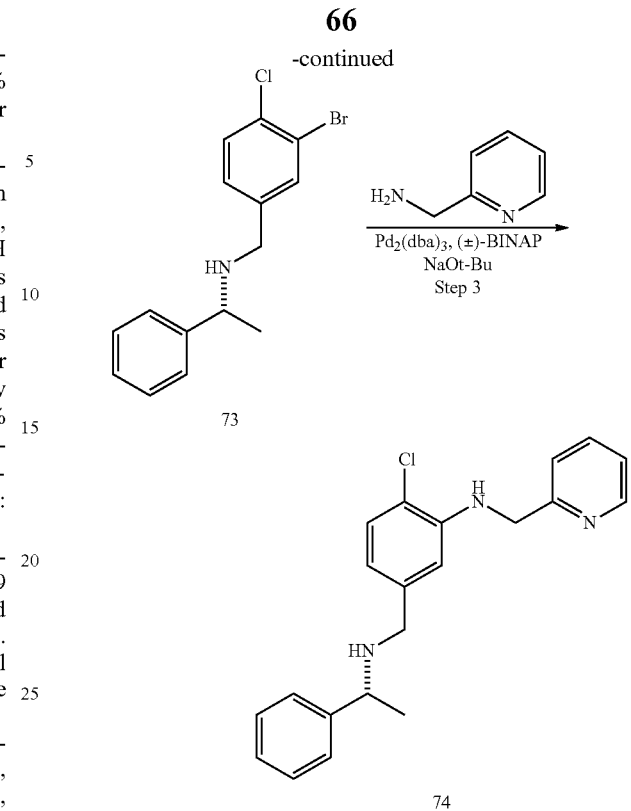

Step 1. To a solution of 3-bromo-4-chlorobenzoic acid 71 (5.30 g, 23 mmol) in DCM (10 mL) at room temperature was added DMF (5 drops) and oxalyl dichloride (3.0 mL, 34 mmol). The reaction mixture was heated to 40° C. for 1 h. The solvent and excess oxalyl chloride were removed under a stream of nitrogen followed by high vacuum. The acid chloride was dissolved in DCM (100 mL), cooled to 0° C., and then pyridine (2.8 mL, 34 mmol) was added followed by (R)-1-phenylethanamine (3.8 mL, 30 mmol). The reaction mixture was stirred at 0° C. for 1 h and concentrated under reduced pressure. The crude amide was dissolved in EtOAc, washed with 1 M HCl (2×), brine (1×), dried over MgSO$_4$, filtered, and concentrated to give (R)-3-bromo-4-chloro-N-(1-phenylethyl)benzamide 72 (8.15 g, 71% yield) as a white solid which was used without further purification. Mass spectrum: calculated for $C_{15}H_{13}BrClNO$ 337.0. found 338.0 (M$^+$+1).

Step 2. To (R)-3-bromo-4-chloro-N-(1-phenylethyl)benzamide 72 (8.15 g, 24.1 mmol) was added borane (130 mL, 129 mmol) (1 M in THF). The reaction mixture was heated to reflux for 3 d, quenched with saturated NaHCO$_3$, and diluted with EtOAc and water. The aqueous phase was extracted with EtOAc (1×) and the combined organic extracts were washed with brine (1×), dried over MgSO$_4$, filtered, and concentrated in vacuo. Purification by flash column chromatography on silica gel (eluted with 10% to 40% EtOAc in hexanes) gave (R)—N-(3-bromo-4-chlorobenzyl)-1-phenylethanamine 73 (4.75 g, 60.8% yield) as a colorless oil. Mass spectrum: calculated for $C_{15}H_{15}BrClN$ 323.0. found 324.1 (M$^+$+1).

Step 3. To a mixture of pyridin-2-ylmethanamine (0.105 g, 1.0 mmol) and (R)—N-(3-bromo-4-chlorobenzyl)-1-phenylethanamine 73 (0.251 g, 0.8 mmol) was added sodium 2-methylpropan-2-olate (0.103 g, 1 mmol), Pd$_2$(dba)$_3$ (0.051 g, 0.06 mmol), 2-(diphenylphosphino)-1-(2-(diphenylphosphino)naphthalen-1-yl)naphthalene (0.210 mg, 0.34 mmol), and toluene (1.5 mL). The reaction mixture was degassed by bubbling nitrogen through the solution for 15 min and heated to 80° C. After 20 h, the reaction mixture was diluted with EtOAc and saturated NaHCO$_3$. The organic phase was washed with brine (1×), dried over MgSO$_4$, filtered, and concentrated in vacuo. Purification by flash column chromatography on silica gel (eluted with 60% to 100% EtOAc in hexanes) followed by flash column chromatography on silica gel (eluted with 1% to 5% MeOH (2 M in NH$_3$) in DCM) gave (R)-2-chloro-5-((1-phenylethylamino)methyl)-N-(pyridin-2-ylmethyl)benzenamine 74 (0.034 g, 12% yield) as a colorless oil. $^1$H NMR (400 MHz, CDCl$_3$) δ 1.31 (d, J=6.5 Hz, 3H), 3.46 (d, J=13.3 Hz, 1H), 3.55 (d, J=13.3 Hz, 1H), 3.72 (q, J=6.5 Hz, 1H), 4.53 (d, J=5.5 Hz, 2H), 5.38 (m, 1H), 6.54-6.58 (m, 2H), 7.20-7.33 (m, 9H), 7.66 (td, J=7.6, 1.8 Hz, 1H), 8.62 (d, J=4.3 Hz, 1H). Mass spectrum: calculated for C$_{21}$H$_{22}$ClN$_3$ 351.2. found 352.2 (M$^+$+1).

Example 15

Synthesis of (1R)—N-(3-(1H-Benzo[d]imidazol-1-yl)-4-chlorobenzyl)-1-phenylethanamine

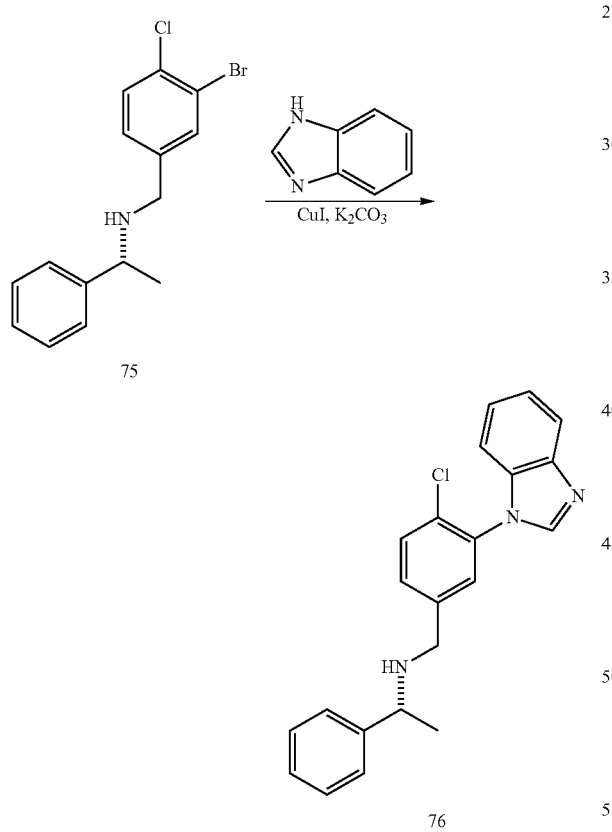

To a mixture of 1H-benzo[d]imidazole (0.106 g, 0.90 mmol) and (R)—N-(3-bromo-4-chlorobenzyl)-1-phenylethanamine 75 (0.247 g, 0.76 mmol) was added potassium carbonate (0.141 g, 1.0 mmol), copper(I) iodide (0.023 g, 0.12 mmol), and NMP (0.8 mL). The reaction mixture was degassed and heated to 150° C. for 3 d, diluted with EtOAc, filtered, and concentrated in vacuo. Purification by flash column chromatography on silica gel (eluted with 40% to 100% EtOAc in hexanes) gave (1R)—N-(3-(1H-benzo[d]imidazol-1-yl)-4-chlorobenzyl)-1-phenylethanamine 76 (0.053 g, 19% yield) as a colorless oil. $^1$H NMR (400 MHz, CDCl$_3$) δ 1.38 (d, J=6.7 Hz, 3H), 3.69 (s, 2H), 3.82 (q, J=6.7 Hz, 1H), 7.20-7.43 (m, 11H), 7.55 (d, J=8.2 Hz, 1H), 7.79 (d, J=7.2 Hz, 1H), 8.04 (s, 1H). Mass spectrum: calculated for C$_{22}$H$_{20}$ClN$_3$ 361.1. found 362.2 (M$^+$+1).

Example 16

Synthesis of (1R)—N-(4-chloro-3-(1H-1,2,4-triazol-1-yl)benzyl)-1-phenylethanamine

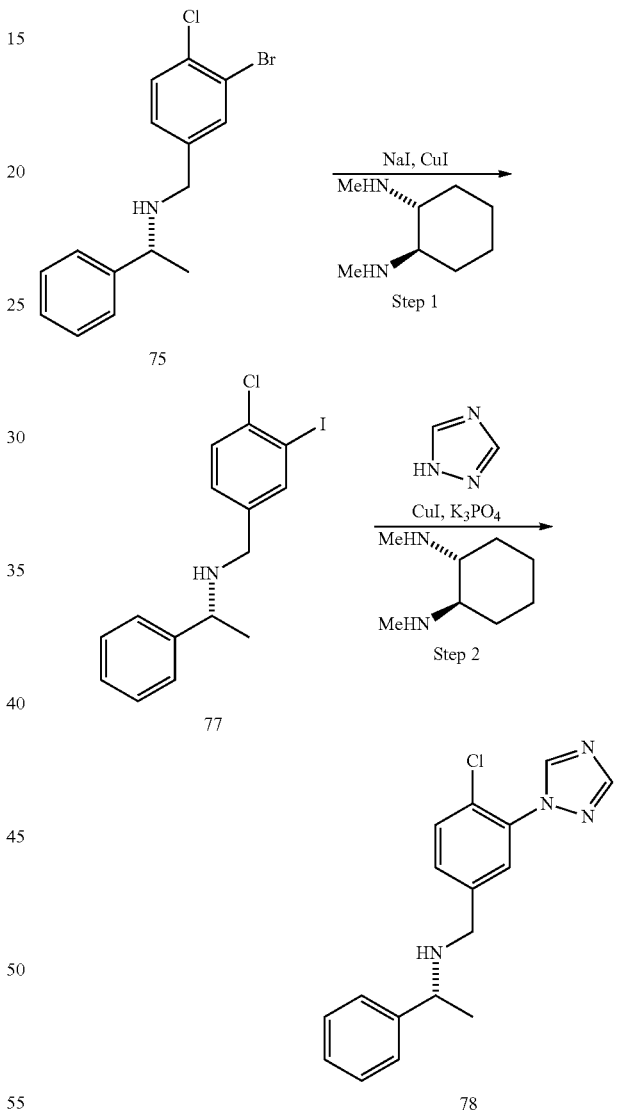

Step 1. To a mixture of sodium iodide (0.19 mL, 4.6 mmol), trans-N1,N2-dimethylcyclohexane-1,2-diamine (0.034 g, 0.24 mmol), (R)—N-(3-bromo-4-chlorobenzyl)-1-phenylethanamine 75 (0.762 g, 2.3 mmol), and copper(I) iodide (0.025 mg, 0.13 mmol) was added in dioxane (2.5 mL). The reaction mixture was degassed by bubbling nitrogen through the solution for 5 min and heated to 115° C. in a sealed tube. After 15 h, the reaction mixture was diluted with EtOAc and the organic phase was washed with dilute NH$_4$OH (1×), brine (1 x), dried over MgSO$_4$, filtered, and concentrated in vacuo.

Purification by flash column chromatography on silica gel (eluted with 10% to 40% EtOAc in hexanes) gave (R)—N-(4-chloro-3-iodobenzyl)-1-phenylethanamine 77 (0.737 g, 84% yield) as a colorless oil. Mass spectrum: calculated for $C_{15}H_{15}ClIN$ 371.0. found 372.1 ($M^++1$).

Step 2. To a mixture of copper(I) iodide (0.022 g, 0.12 mmol), trans-N1,N2-dimethylcyclohexane-1,2-diamine (0.027 g, 0.19 mmol), potassium phosphate (0.420 g, 2.0 mmol), 1H-1,2,4-triazole (0.078 g, 1.1 mmol), and (R)—N-(4-chloro-3-iodobenzyl)-1-phenylethanamine 77 (0.352 g, 0.95 mmol) was added DMF (1 mL). The reaction mixture was degassed by a purge/nitrogen cycle (3×) and heated in a sealed tube to 110° C. After 24 h, the reaction mixture was diluted with EtOAc and the organic phase was washed with saturated $NH_4Cl/NH_4OH$ (10:1) (1×), brine (1×), dried over $MgSO_4$, filtered, and concentrated in vacuo. Purification by flash column chromatography on silica gel (eluted with 10% to 100% EtOAc in hexanes) gave (1R)—N-(4-chloro-3-(1H-1,2,4-triazol-1-yl)benzyl)-1-phenylethanamine 78 (0.031 g, 10% yield) as a colorless oil. $^1$H NMR (400 MHz, $CDCl_3$) δ 1.38 (d, J=6.5 Hz, 3H), 3.66 (s, 2H), 3.80 (q, J=6.5 Hz, 1H), 7.24-7.36 (m, 7H), 7.48 (d, J=8.2 Hz, 1H), 7.54 (s, 1H), 8.14 (s, 1H), 8.52 (s, 1H). Mass spectrum: calculated for $C_{17}H_{17}ClN_4$ 312.1. found 313.2 ($M^++1$).

Example 17

Synthesis of ((1R)—N-(4-Chloro-3-((1-methylpiperidin-3-yl)methoxy)benzyl)-1-(3-chlorophenyl)ethanamine

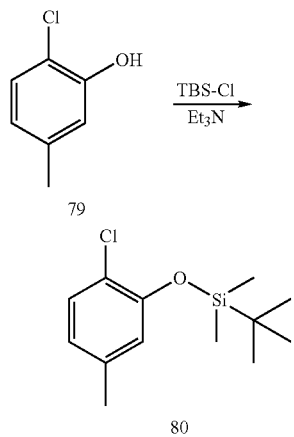

Step 1. A solution containing 2-chloro-5-methylphenol 79 (3.50 g, 25 mmol), triethylamine (3.8 mL, 27 mmol), and DMAP (0.030 g, 0.25 mmol) in 50 mL of DMF was chilled to 0° C. under $N_2$. A solution of tert-butylchlorodimethylsilane (3.9 g, 26 mmol) in 5 mL of DMF was added to the reaction mixture slowly via syringe over 5 min. The reaction was warmed to room temperature and stirred for 12 h. The mixture was diluted with ether and it was extracted with 2×1 N HCl, water, and then brine. The organic layer was dried over $MgSO_4$, filtered, and concentrated in vacuo. The crude material was purified by silica gel chromatography using a 5% to 30% gradient of EtOAc in hexanes as the eluant. The desired fractions were combined and concentrated to give tert-butyl (2-chloro-5-methylphenoxy)dimethylsilane 80 (6.15 g, 98% yield) as a colorless oil.

Step 2. A solution containing tert-butyl(2-chloro-5-methylphenoxy)dimethylsilane 80 (6.15 g, 24 mmol), N-bromosuccinimide (4.7 g, 26 mmol), and benzoyl peroxide (0.058 g, 0.24 mmol) in 40 mL of dry $CHCl_3$ was purged with $N_2$ and heated to 85° C. The reaction was exposed to a 60 W lamp and was stirred at reflux for 4 h. The lamp was removed and the reaction was cooled to room temperature. The solution was concentrated and was redissolved in ether. The mixture was filtered and then concentrated again. The crude material was purified by silica gel chromatography using a 5% to 20% gradient of EtOAc in hexanes as the eluant. The desired fractions were combined and concentrated to give (5-(bromomethyl)-2-chlorophenoxy)(tert-butyl)dimethylsilane 81 (2.7 g, 34% yield). The product was carried forth to the next step as is.

Step 3. A solution of (5-(bromomethyl)-2-chlorophenoxy)(tert-butyl)dimethylsilane 81 (1.00 g, 2.98 mmol) and potassium carbonate (0.453 g, 3.28 mmol) in DMF was stirred at room temp under N₂. (R)-1-(3-Chlorophenyl)ethanamine (0.464 g, 2.98 mmol) was added to the solution and the reaction was stirred at room temperature for 8 h. The reaction was checked by TLC for completion. The reaction mixture was diluted with water and ether. The ether solution was washed with water (2×) and brine. The organic layer was dried over MgSO₄, filtered, and concentrated in vacuo. The crude material was purified by silica gel chromatography using a 5% to 30% gradient of EtOAc in hexanes as the eluant. The desired fractions were combined and concentrated to give (R)—N-(3-(tert-butyldimethylsilyloxy)-4-chlorobenzyl)-1-(3-chlorophenyl)ethanamine 82 (0.612 g, 50.1% yield) as a colorless oil. The product was carried forth to the next step without further purification.

Step 4. To a solution of (R)—N-(3-(tert-butyldimethylsilyloxy)-4-chlorobenzyl)-1-(3-chlorophenyl)ethanamine 82 (540 mg, 1316 μmol) in THF was added tetra-butylammonium fluoride (1M soln in THF, 1381 μL, 1381 μmol). The solution was stirred at room temperature under N₂ for 3 h and then checked by TLC for completion. The reaction solution was concentrated and the crude material was purified by silica gel chromatography using a 5% to 60% gradient of EtOAc in hexanes as the eluant. The desired fractions were combined and concentrated to give (R)-2-chloro-5-((1-(3-chlorophenyl)ethylamino)methyl)phenol 83 (200 mg, 91% yield) as a white solid. 1H NMR (400 MHz, CHLOROFORM-d) δ ppm 1.34 (d, J=6.46 Hz, 3H) 3.50-3.61 (m, 2H) 3.77 (q, J=6.52 Hz, 1H) 6.78 (dd, J=8.22, 1.37 Hz, 1H) 6.96 (d, J=1.37 Hz, 1H) 7.20-7.29 (m, 4H) 7.34 (s, 1H). Mass spectrum: calculated for $C_{15}H_{15}Cl_2NO$ 296.2. found 297.3 (M⁺+1).

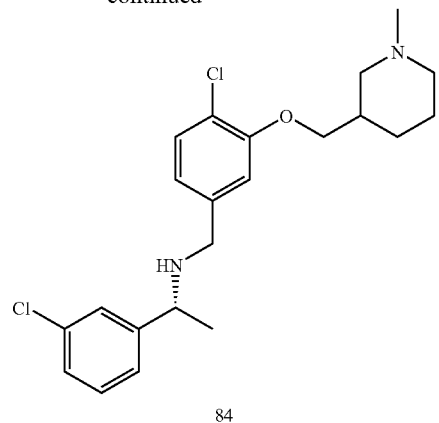

84

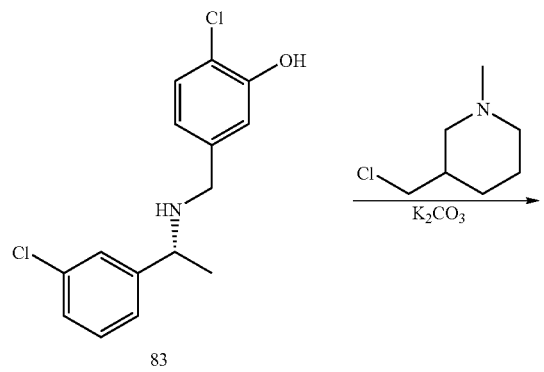

83

Step 5. A small vial was charged with 2 mL of acetonitrile, cesium carbonate (50 mg, 0.15 mmol), (R)-2-chloro-5-((1-(3-chlorophenyl)ethylamino)methyl)phenol 83 (30 mg, 0.10 mmol), and 3-(chloromethyl)-1-methylpiperidine (16 mg, 0.11 mmol). The vial was placed in a reaction block and it was heated to 85° C. and stirred for 14 h. The vial was allowed to cool to room temperature and the solution was filtered through a syringe filter into a well of a 24 well plate. This plate was concentrated down in a Genevac vacuum instrument. The plate was by preparatory HPLC. The desired fractions were combined and lyophilized. The final product, (1R)—N-(4-chloro-3-((1-methylpiperidin-3-yl)methoxy)benzyl)-1-(3-chlorophenyl)ethanamine 84 (32 mg, 75% yield) was isolated as a white solid of the TFA salt. 1H NMR (400 MHz, d₄-methanol) δ ppm 1.44-1.56 (m, 1H) 1.72 (m, 2H) 1.99 (m, 1H) 2.07 (m, 1H) 2.40 (m, 1H) 2.91-3.00 (m, 4H) 3.55 (m, 1H) 3.67-3.74 (m, 1H) 3.93-4.01 (m, 2H) 4.10 (dd, J=9.00, 4.11 Hz, 1H) 4.18 (d, J=13.11 Hz, 1H) 4.48 (q, J=6.85 Hz, 1H) 5.50 (s, 1H) 7.00 (d, J=8.22, 1H) 7.15 (s, 1H) 7.43-7.52 (m, 3H) 7.57 (s, 1H). Mass spectrum: calculated for $C_{22}H_{28}C_{12}N_2O$ 407.4. found 408.4 (M⁺+1).

Example 18

The compounds shown in the Table 4 below were prepared using the same procedure as described in Example 17 with the exception of substituting 3-(chloromethyl)-1-methylpiperidine for the corresponding alkylating reagent. In the case of compound 91, the reaction was performed in DMF at 120° C. for 28 h.

TABLE 4

| Comp | Structure | Name | m/z | Alkylation Reagent |
|---|---|---|---|---|
| 85 | 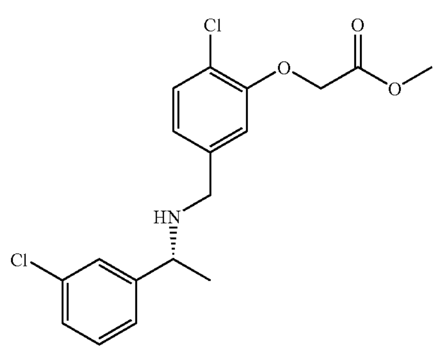 [SMILES: COC(=O)COc1cc(CN[C@H](C)c2cccc(Cl)c2)ccc1Cl] | (R)-methyl 2-(2-chloro-5-((1-(3-chlorophenyl)ethylamino)-methyl)phenoxy)acetate | 369 | |

TABLE 4-continued
| Comp | Structure | Name | Alkylation m/z | Reagent |
|---|---|---|---|---|
| 86 | 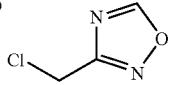 | (R)-N-(3-((1,2,4-oxadiazol-3-yl)methoxy)-4-chlorobenzyl)-1-(3-chlorophenyl)ethanamine | 379 | |
| 87 | 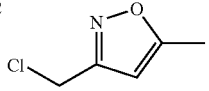 | (R)-N-(4-chloro-3-((5-methylisoxazol-3-yl)methoxy)benzyl)-1-(3-chlorophenyl)ethanamine | 392 | |
| 88 | 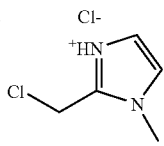 | (R)-N-(4-chloro-3-((1-methyl-1H-imidazol-2-yl)methoxy)benzyl)-1-(3-chlorophenyl)ethanamine | 391 | |
| 89 | 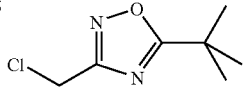 | (R)-N-(3-((5-tert-butyl-1,2,4-oxadiazol-3-yl)methoxy)-4-chlorobenzyl)-1-(3-chlorophenyl)ethanamine | 435 | |

TABLE 4-continued
| Comp | Structure | Name | m/z | Alkylation Reagent |
|---|---|---|---|---|
| 90 | 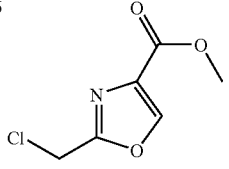 | (R)-methyl 2-((2-chloro-5-((1-(3-chlorophenyl)ethylamino)-methyl)phenoxy)methyl)oxazole-4-carboxylate | 436 | |
| 91 | 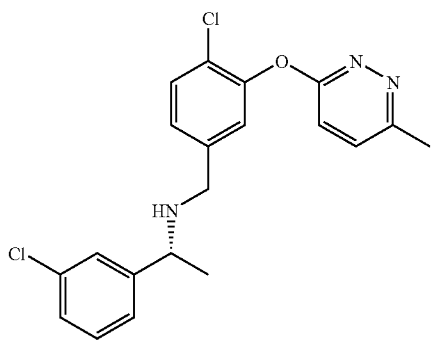 [SMILES: Cc1ccc(Oc2cc(CN[C@H](C)c3cccc(Cl)c3)ccc2Cl)nn1] | (R)-N-(4-chloro-3-(6-methylpyridazin-3-yloxy)benzyl)-1-(3-chlorophenyl)ethanamine | 389 | 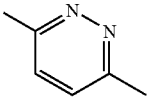 |
| 92 | 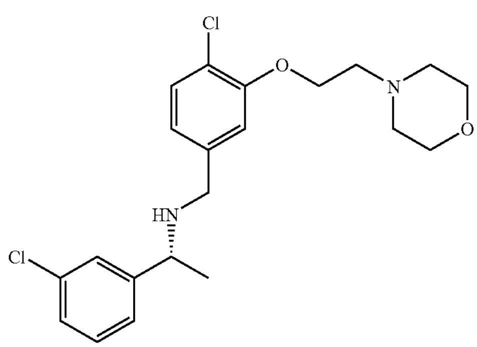 [SMILES: C[C@@H](NCc1ccc(Cl)c(OCCN2CCOCC2)c1)c1cccc(Cl)c1] | (R)-N-(4-chloro-3-(2-morpholinoethoxy)benzyl)-1-(3-chlorophenyl)ethanamine | 410 | 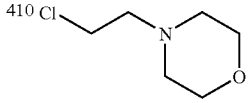 |
| 93 | 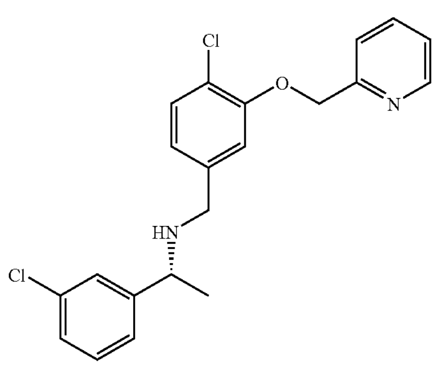 [SMILES: C[C@@H](NCc1ccc(Cl)c(OCc2ccccn2)c1)c1cccc(Cl)c1] | (R)-N-(4-chloro-3-(pyridin-2-ylmethoxy)benzyl)-1-(3-chlorophenyl)ethanamine | 388 | 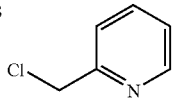 |

TABLE 4-continued

| Comp | Structure | Name | m/z | Alkylation Reagent |
|---|---|---|---|---|
| 94 | 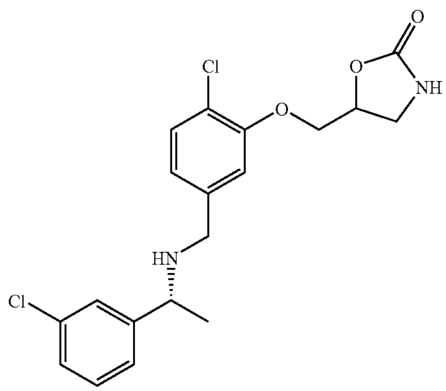 [SMILES: C[C@@H](NCc1ccc(Cl)c(OCC2CNC(=O)O2)c1)c1cccc(Cl)c1] | 5-((2-chloro-5-(((R)-1-(3-chlorophenyl)ethylamino)-methyl)phenoxy)methyl)oxazolidin-2-one | 396 | |
| 95 | 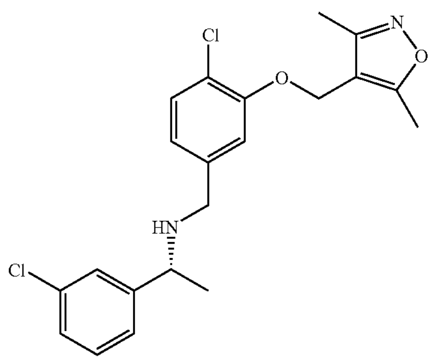 [SMILES: Cc1noc(C)c1COc1cc(CN[C@H](C)c2cccc(Cl)c2)ccc1Cl] | (R)-N-(4-chloro-3-((3,5-dimethylisoxazol-4-yl)methoxy)benzyl)-1-(3-chlorophenyl)ethanamine | 406 | |

Example 19

Synthesis of 1-(2-Chloro-5-((((R)-1-(3-chlorophenyl)ethylamino)methyl)phenoxy)propan-2-ol

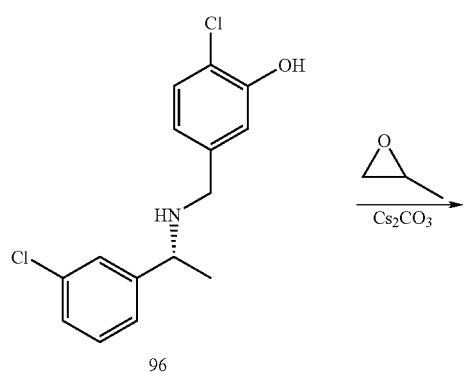

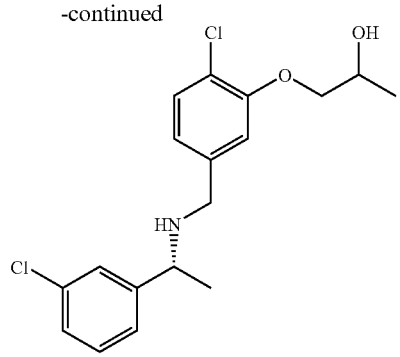

A microwave compatible vial was charged with 2 mL of CH₃CN, (R)-2-chloro-5-((1-(3-chlorophenyl)ethylamino)methyl)phenol 96 (115 mg, 388 μmol), propylene oxide (33 μL, 466 μmol), and cesium carbonate (139 mg, 427 μmol). The vial was sealed and was subjected to microwave irradiation at 140° C. for 30 min. The reaction was checked for completion by TLC. The reaction solution was diluted with EtOAc and it was washed with water (2×) and then brine. The organic layer was dried over MgSO₄, filtered, and concentrated in vacuo. The crude material was purified by silica gel chromatography using a 10% to 70% gradient of EtOAc in hexanes as the eluant. The desired fractions were combined and concentrated to give 1-(2-chloro-5-(((R)-1-(3-chlorophenyl)ethylamino)methyl)phenoxy)propan-2-ol 97 (85 mg, 62% yield), as a colorless oil and as a mixture of diastereomers. 1H NMR (400 MHz, d$_4$-methanol) δ ppm 1.32 (d, J=6.46 Hz, 3H) 1.73 (d, J=6.85 Hz, 3H) 3.92-4.02 (m, 3H) 4.13-4.21 (m, 2H) 4.49 (q, J=6.78 Hz, 1H) 6.98 (dd, J=8.12, 1.66 Hz, 1H) 7.43-7.49 (m, 2H) 7.49-7.53 (m, 2H) 7.58 (s, 1H). Mass spectrum: calculated for C$_{18}$H$_{21}$Cl$_2$NO$_2$ 354.3. found 355.4 (M$^+$+1).

Example 20

Synthesis of (1R)—N-(4-chloro-3-(1-(pyridin-2-yl)ethoxy)benzyl)-1-(3-chlorophenyl)ethanamine

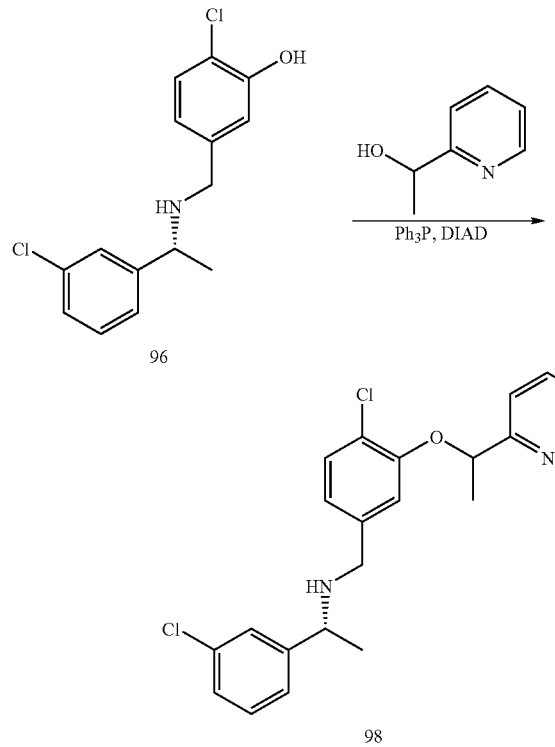

J=6.65 Hz, 2.1H) 1.73 (d, J=5.28 Hz, 3H) 1.83 (d, J=6.46 Hz, 3H) 3.90 (d, J=11.15 Hz, 1H) 4.16 (d, J=12.72 Hz, 1H) 4.45-4.54 (m, 1H) 5.18-5.28 (m, 0.7H) 5.99 (m, 1H) 7.05 (d, 1H) 7.48 (m, 5H) 7.63 (m, 1H) 7.99 (m, 1.7H) 8.08 (m, 0.7H) 8.20 (d, 1H) 8.59 (m, 1.7H) 8.73 (m, 0.7H) 8.83 (d, 1H). Mass spectrum: calculated for C$_{22}$H$_{22}$Cl$_2$N$_2$O 401.3. found 402.4 (M$^+$+1).

Example 21

Synthesis of (1R)—N-(4-Chloro-3-(1-(methylsulfonyl)pyrrolidin-3-yloxy)benzyl)-1-(3-chlorophenyl)ethanamine

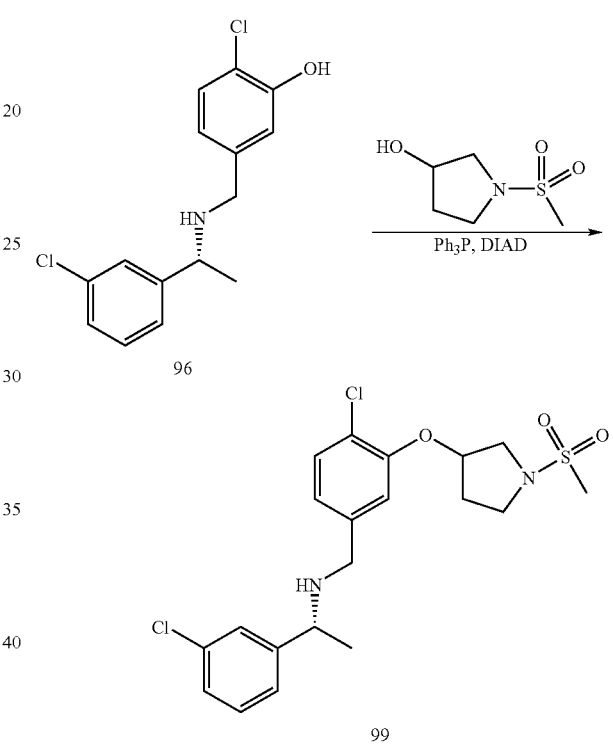

To a solution of (R)-2-chloro-5-((1-(3-chlorophenyl)ethylamino)methyl)phenol 96 (150 mg, 506 μmol) in 5 mL of THF under N$_2$ was added triphenylphosphine (146 mg, 557 μmol). The solution was chilled to 0° C. in an ice bath and then diisopropyl azodicarboxylate (108 μL, 557 μmol) was added dropwise to the reaction. After stirring for 15 min 0° C., a solution of 1-(methylsulfonyl)pyrrolidin-3-ol (84 mg, 506 μmol) in THF was added to the reaction. The reaction was allowed to warm to room temperature and it was stirred for 10 h. The reaction was concentrated and diluted with EtOAc. The organic solution was extracted with saturated NaHCO$_3$, water, and brine. The organic layer was dried over MgSO$_4$, filtered, and concentrated in vacuo. The crude material was purified by silica gel chromatography using a 10% to 80% gradient of EtOAc in hexanes as the eluant. The desired fractions were combined and concentrated to give (1R)—N-(4-chloro-3-(1-(methylsulfonyl)pyrrolidin-3-yloxy)benzyl)-1-(3-chlorophenyl)ethanamine 99 (83 mg, 37% yield) as a colorless oil and as a mixture of diastereomers. 1H NMR (400 MHz, d$_4$-methanol) δ ppm 1.26 (d, 1H) 1.73 (d, J=6.85 Hz, 3H) 2.25-2.32 (m, 2H) 2.91 (s, 3H) 3.51-3.60 (m, 2H) 3.62-3.66 (m, 2H) 4.00 (d, 1H) 4.20 (d, 1H) 4.50 (m, 1H) 5.08-5.13

To a solution of (R)-2-chloro-5-((1-(3-chlorophenyl)ethylamino)methyl)phenol 96 (130 mg, 439 μmol) in 5 mL of THF under N$_2$ was added triphenylphosphine (127 mg, 483 μmol). The solution was chilled to 0° C. in an ice bath and then diisopropyl azodicarboxylate (94 μL, 483 μmol) was added dropwise to the reaction. After stirring for 15 min 0° C., a solution of 1-(pyridin-2-yl)ethanol (59 mg, 483 μmol) in THF was added to the reaction. The reaction was allowed to warm to room temperature and it was stirred for 10 h. The reaction was concentrated and diluted with EtOAc. The solution was extracted with saturated NaHCO$_3$, water, and then brine. The organic layer was dried over MgSO$_4$, filtered, and concentrated in vacuo. The crude material was purified by silica gel chromatography using a 5% to 90% gradient of EtOAc in hexanes as the eluant. The desired fractions were combined and concentrated to give (1R)—N-(4-chloro-3-(1-(pyridin-2-yl)ethoxy)benzyl)-1-(3-chlorophenyl)ethanamine 98 (67 mg, 38% yield) as a colorless oil and as a mixture of diastereomers. 1H NMR (400 MHz, d$_4$-methanol) δ ppm 1.60 (d, (m, 1H) 6.99-7.07 (m, 1H) 7.14-7.18 (m, 1H) 7.43-7.52 (m, 4H) 7.57 (m, 1H). Mass spectrum: calculated for $C_{20}H_{24}Cl_2N_2O_3S$ 443.4. found 444.4 ($M^++1$).

Example 22

Synthesis of (R)-2-(2-Chloro-5-((1-(3-chlorophenyl)ethylamino)methyl)phenoxy)acetic acid

Example 23

Synthesis of (R)-2-((2-Chloro-5-((1-(3-chlorophenyl)ethylamino)methyl)phenoxy)methyl)oxazole-4-carboxylic acid

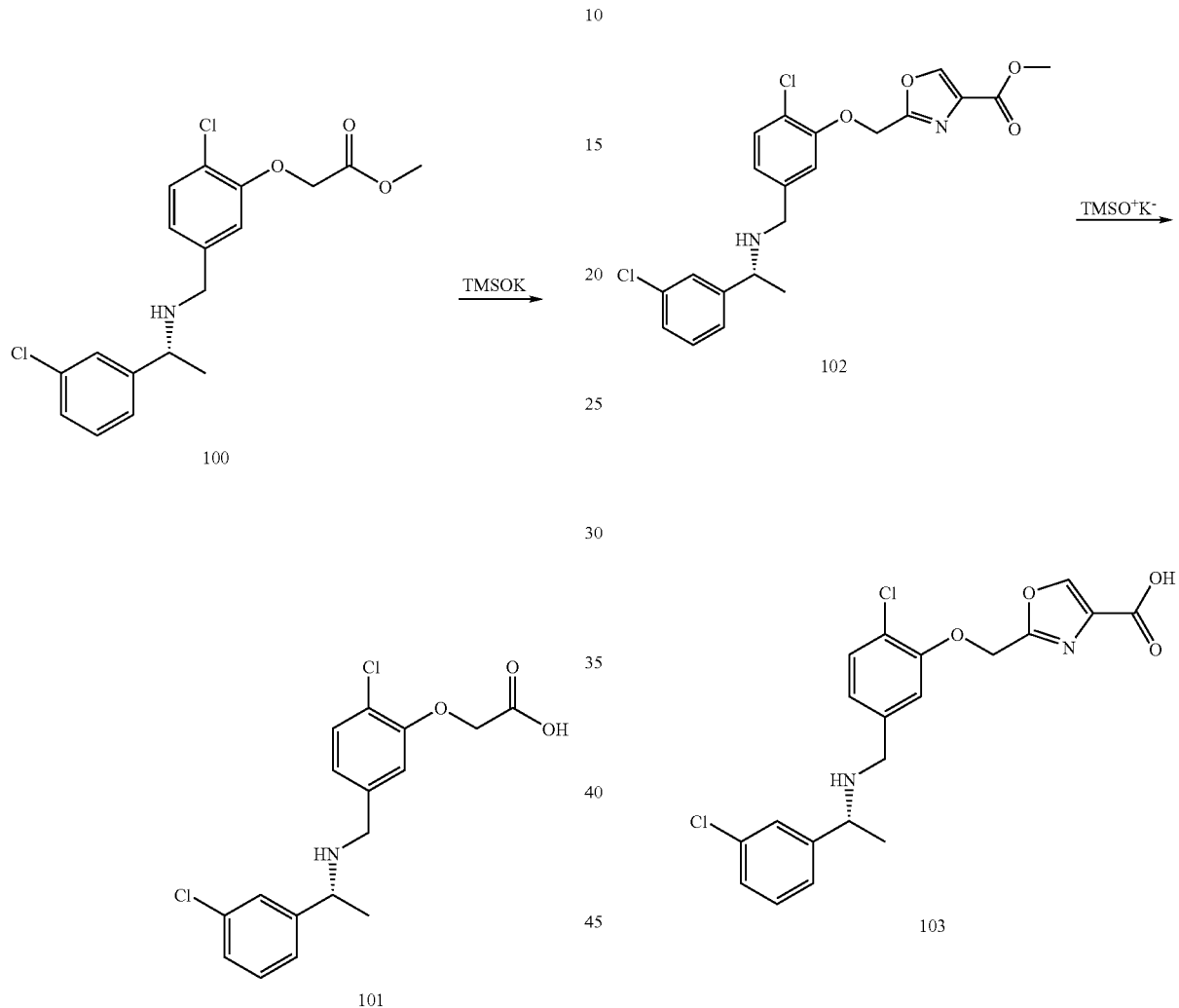

To a solution of (R)-methyl 2-(2-chloro-5-((1-(3-chlorophenyl)ethylamino) methyl)phenoxy)acetate 100 (50 mg, 136 μmol) in 2 mL of dry THF, was added potassium trimethylsilanolate (17 mg, 136 μmol). The solution was stirred at ambient temperature for 2 h. The reaction was concentrated and the resulting crude material was purified with reverse phase preparatory HPLC. The desired fractions were combined and lyophilized to give (R)-2-(2-chloro-5-((1-(3-chlorophenyl)ethylamino)methyl)phenoxy)acetic acid 101 (35 mg, 73% yield) as a white solid and as the TFA salt. 1H NMR (400 MHz, d$_4$-methanol) δ ppm 1.71 (d, J=6.85 Hz, 3H) 3.98 (d, J=13.30 Hz, 1H) 4.16 (d, J=13.11 Hz, 1H) 4.44 (m, 1H) 4.81 (s, 2H) 6.97-7.01 (m, 1H) 7.05-7.07 (m, 1H) 7.41-7.52 (m, 4H) 7.54-7.57 (s, 1H). Mass spectrum: calculated for $C_{17}H_{17}Cl_2NO_3$ 354.2. found 355.3 ($M^++1$).

To a solution of (R)-methyl 2-((2-chloro-5-((1-(3-chlorophenyl)ethylamino)methyl)phenoxy)methyl)oxazole-4-carboxylate 102 (69 mg, 159 μmol) in 2 mL of dry THF, was added potassium trimethylsilanolate (22 mg, 174 μmol). The solution was stirred at ambient temperature for 2 h. The reaction was concentrated and the resulting crude material was purified with reverse phase preparatory HPLC. The desired fractions were combined and lyophilized to give (R)-2-((2-chloro-5-((1-(3-chlorophenyl)ethylamino)methyl)phenoxy)methyl)oxazole-4-carboxylic acid 103 (41 mg, 61% yield) as a white solid and as the TFA salt. 1H NMR (400 MHz, d$_4$-methanol) δ ppm 1.68-1.74 (m, 3H) 4.02 (d, J=13.30 Hz, 1H) 4.20 (d, J=13.30 Hz, 1H) 4.48 (q, J=6.85 Hz, 1H) 5.34 (s, 2H) 7.04 (dd, J=8.22, 1.76 Hz, 1H) 7.33 (d, J=1.76 Hz, 1H) 7.43-7.52 (m, 4H) 7.56 (s, 1H) 8.60 (s, 1H). Mass spectrum: calculated for $C_{20}H_{18}Cl_2N_2O_4$ 421.3. found 422.4 ($M^++1$).

Example 24

Synthesis of N-(2-Chloro-5-(1-((R)-1-(3-chlorophenyl)ethylamino)ethyl)phenyl)-5-methylisoxazole-3-carboxamide

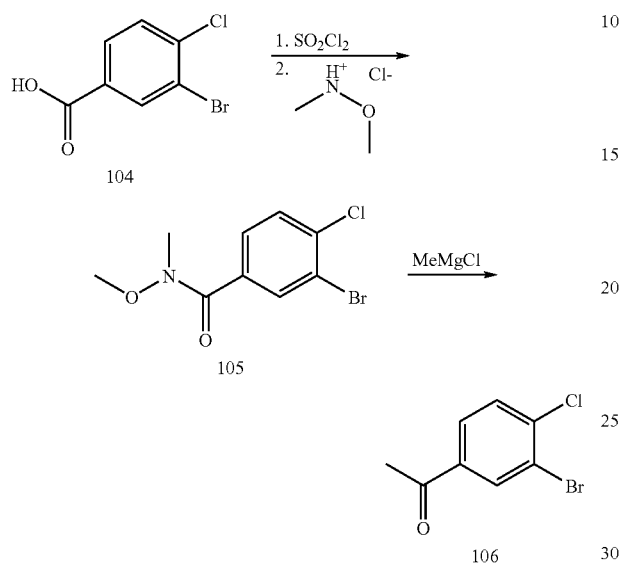

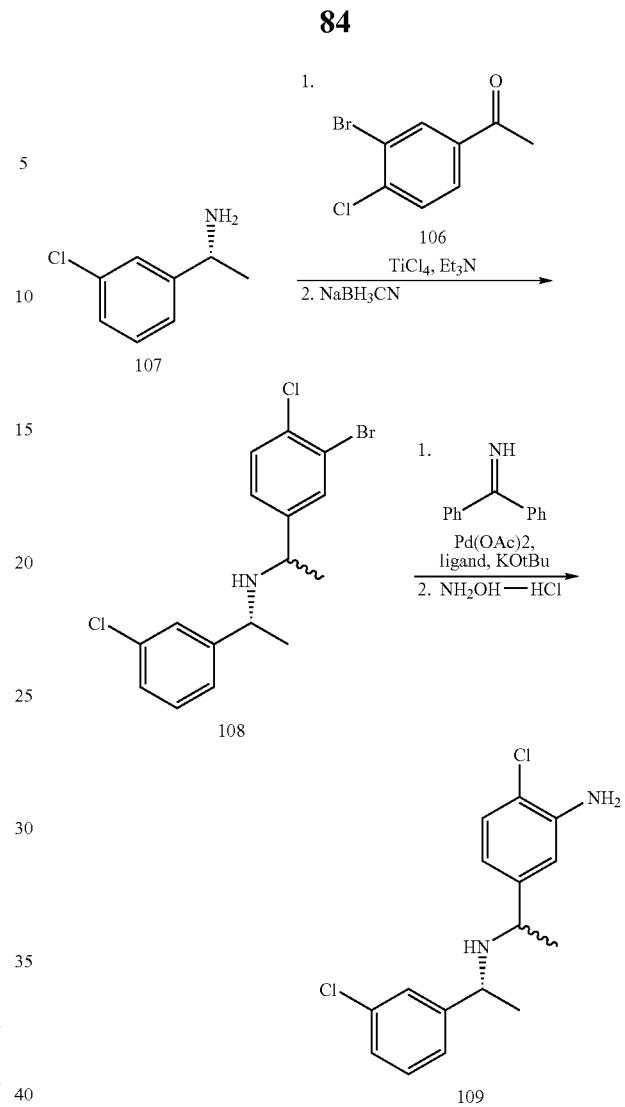

Step 1. A solution of 3-bromo-4-chlorobenzoic acid 104 (2.354 g, 10.0 mmol) in 30 mL of $CH_2Cl_2$ was chilled to 0° C. in an ice bath. To this solution was added a solution of thionyl chloride (2.2 mL, 30 mmol) in $CH_2Cl_2$ and then a few drops of DMF. The reaction was warmed to room temperature and stirred under $N_2$ for 2 h. The reaction mixture was concentrated in vacuo. The crude acid chloride was re-dissolved in $CH_2Cl_2$ and it was chilled to 0° C. Triethylamine (2.8 mL, 20 mmol) was slowly added to the reaction via syringe. The reaction was warmed to room temperature and stirred for 2 h under $N_2$. The reaction mixture was concentrated and then diluted with EtOAc. The solution was extracted with saturated $NaHCO_3$, water, and brine. The organic layer was dried over $MgSO_4$, filtered, and concentrated in vacuo. The crude material was purified by ISCO flash chromatography using a 5% to 60% gradient of EtOAc in hexanes as the eluant. The desired fractions were combined and concentrated to give 3-bromo-4-chloro-N-methoxy-N-methylbenzamide 105 (2.43 g, 87% yield) as a colorless oil.

Step 2. A solution of 3-bromo-4-chloro-N-methoxy-N-methylbenzamide 105 (2.04 g, 7.3 mmol), was dissolved in 30 mL of dry THF. The solution was chilled to −5° C. in a salt bath under $N_2$. Via syringe, methylmagnesium bromide (2.7 mL, 8.1 mmol) was added slowly to the solution. The solution was stirred for 2 h at −5° C., and then it was warmed to room temperature where it was stirred for another 1 h. The reaction was quenched with saturated $NH_4Cl$, and it was diluted with ether and water. The organic solution was extracted with water and brine. The organic phase was dried over $MgSO_4$, filtered, and concentrated in vacuo. The crude material was then filtered through a bed of silica and the filtrate was concentrated to give 1-(3-bromo-4-chlorophenyl)ethanone 106 (1.55 g, 91% yield) as a white solid.

Step 3. A solution of (R)-1-(3-chlorophenyl)ethanamine 107 (0.701 g, 4.50 mmol), 1-(3-bromo-4-chlorophenyl)ethanone 106 (1.00 g, 4.29 mmol), and triethylamine (1.79 mL, 12.9 mmol) in dry DME was chilled to −78° C. in a dry ice bath. Via syringe, titanium(IV) chloride (4.50 mL, 4.50 mmol) was added dropwise to the reaction mixture. The reaction was warmed to ambient temperature and it was stirred under $N_2$ for 10 h. A solution of sodium cyanoborohydride (0.674 g, 10.7 mmol) in 4 mL of MeOH was then added slowly to the reaction mixture and the reaction solution was stirred for another 3 h. The reaction was quenched by the addition of saturated $NH_4Cl$. The solution was diluted with ether and water, and the mixture was extracted with water (2×) and brine. The organic layer was dried over $MgSO_4$, filtered, and concentrated in vacuo. The crude material was purified by silica gel chromatography using a 3% to 30% gradient of EtOAc in hexanes as the eluant. The desired fractions were combined and concentrated to give 1-(3-bromo-4-chlorophenyl)-N—((R)-1-(3-chlorophenyl)ethyl)ethanamine 108 (1.04 g, 65.0% yield) as a colorless oil.

Step 4. A flask containing palladium acetate (8.0 mg, 36 μmol), diphenylmethanimine (78 mg, 428 μmol), 2-(dicyclohexylphosphino)-2'-4',6'-tri-isopropyl-1,1'-biphenyl (51 mg, 107 μmol), 1-(3-bromo-4-chlorophenyl)-N—((R)-1-(3-chlorophenyl)ethyl)ethanamine 108 (133 mg, 356 μmol), and sodium 2-methylpropan-2-olate (69 mg, 713 μmol) in 2 mL of toluene was purged with N₂ for 5 min and then sealed. The reaction was heated to 110° C. for 12 h. The solution was diluted with EtOAc and then extracted with water and brine. The organic layer was dried over MgSO₄, filtered, and concentrated in vacuo. The crude material was purified by silica gel chromatography using a 5% to 40% gradient of EtOAc in hexanes as the eluant. The desired fractions were combined and concentrated to give the coupled imine product. The coupled imine product was dissolved in methanol and then hydroxylamine hydrochloride (62 mg, 891 μmol) was added to the solution. The reaction was stirred for 4 h at ambient temperature under N₂. The reaction mixture was concentrated and then purified by silica gel chromatography using a 5% to 60% gradient of EtOAc in hexanes as the eluant. The desired fractions were combined and concentrated to give 2-chloro-5-(1-((R)-1-(3-chlorophenyl)ethylamino)ethyl)benzenamine 109 (20 mg, 18% yield). Mass spectrum: calculated for $C_{16}H_{18}Cl_2N_2$ 309.2. found 309.3 (M⁺+1).

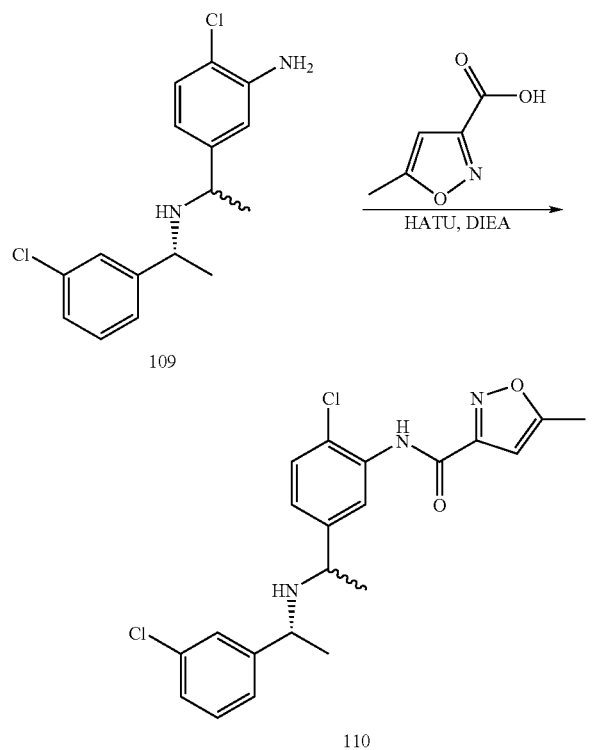

Step 5. A solution of 5-methylisoxazole-3-carboxylic acid (8.6 mg, 68 μmol), diisopropylethylamine (12 μL, 68 μmol), and 2-chloro-5-(1-((R)-1-(3-chlorophenyl)ethylamino) ethyl)benzenamine 109 (21 mg, 68 μmol) in DMF was stirred under N₂ and chilled to 0° C. HATU (26 mg, 68 μmol) was then added to the solution. The reaction was allowed to warm to room temperature and stirred for 3 h. Afterwards, the reaction was diluted with water and EtOAc. The organic solution was extracted with saturated NaHCO₃, water, and brine. The organic layer was dried over MgSO₄, filtered, and concentrated in vacuo. The crude material was purified by silica gel chromatography using a 5% to 60% gradient of EtOAc in hexanes as the eluant. The desired fractions were combined and concentrated to give N-(2-chloro-5-(1-((R)-1-(3-chlorophenyl)ethylamino)ethyl)phenyl)-5-methylisoxazole-3-carboxamide 110 (20 mg, 70% yield) as a colorless oil and as a mixture of diastereomers. 1H NMR (400 MHz, MeOH) δ ppm 1.60-1.66 (m, 6H) 2.53 (s, 3H) 4.19 (m, 2H) 6.61 (s, 1H) 7.19 (dd, J=8.31, 2.05 Hz, 1H) 7.30 (m, 1H) 7.40 (s, 1H) 7.48 (d, J=4.89 Hz, 2H) 7.63 (d, J=8.41 Hz, 1H) 8.09 (s, 1H). Mass spectrum: calculated for $C_{21}H_{21}Cl_2N_3O_2$ 418.3. found 418.4 (M⁺+1).

Example 25

Synthesis of (R)—N-(3-(4-Methoxyphenyl)-4,5-dimethoxybenzyl)-1-phenylethanamine

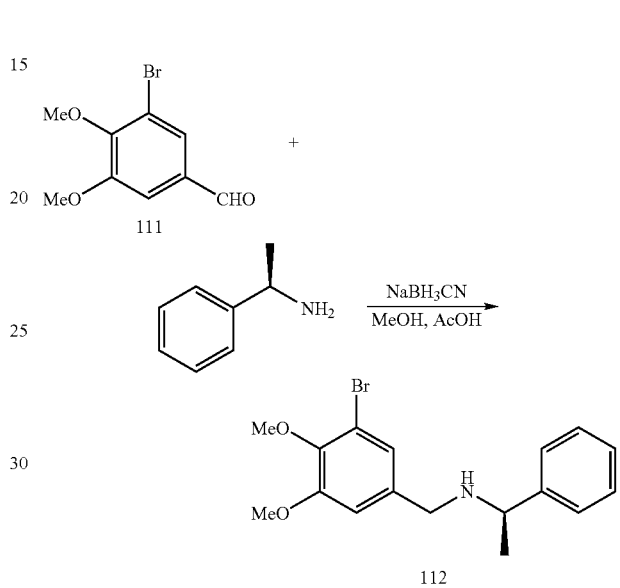

Step 1. A solution of 3-bromo-4,5-dimethoxybenzaldehyde 111 (5.0 g, 0.020 mol, Aldrich), (R)-1-phenylethanamine (2.6 mL, 0.020 mol, Aldrich) and ACQH (5.0 mL) in 70 mL of MeOH was stirred at room temp. for 2 hours. The solution was then cooled to 0° C. and NaBH₃CN solid was added in portions. The reaction solution was then warmed up to room temp and continued to stir overnight. The mixture was concentrated in vacuo and re-dissolved in 150 mL of EtOAc. The organic solution was washed with 50 mL of saturated. NaHCO₃ followed by 50 mL of brine, dried over Na₂SO₄ and concentrated in vacuo. The residue was passed through a short silica gel pad (eluted with 50% EtOAc/hex). The eluant was concentrated in vacuo to give a light yellow oil, which solidified upon standing to give desired product (R)—N-(3-bromo-4,5-dimethoxybenzyl)-1-phenylethanamine 112 as white waxy solid (5.1 g, 73%). MS (ESI, pos. ion) m/z: 350.2 (M+1). ¹H NMR (400 MHz, CDCl₃) δ ppm 7.4-7.5 (m, 5H); 6.9 (s, 1H); 7.0 (s, 1H), 3.9 (s, 3H); 3.8 (s, 3H); 3.7-3.9 (m, 3H); 1.7 (d, J=7.0 Hz, 3H).

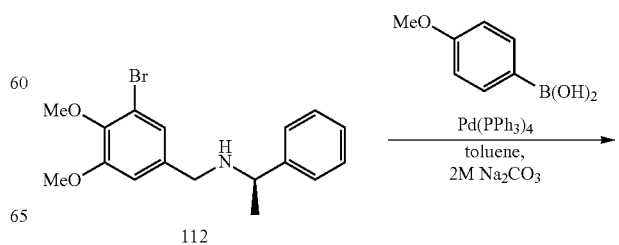

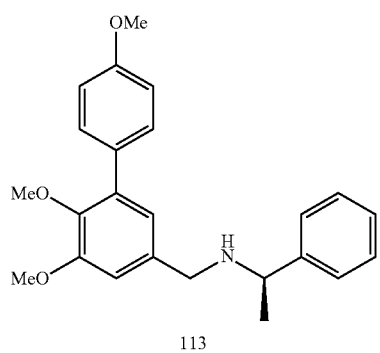

113

Step 2. To a mixture of (R)—N-(3-bromo-4,5-dimethoxybenzyl)-1-phenylethanamine 112 (1.1 g, 3.15 mmol), 4-methoxyphenylboronic acid (0.48 g, 3.15 mmol, Aldrich) and 2M Na$_2$CO$_3$ (5.0 mL) in 10 mL of toluene was added PPh$_3$ (83 mg, 0.315 mmol) and Pd(PPh$_3$)$_4$ (0.364 g, 0.315 mmol) at room temp. under N$_2$. The reaction mixture was then heated up to 80° C. under N$_2$ atmosphere overnight. EtOH (4 mL) was added and the reaction was continued at 80° C. for 4 hours. The reaction was cooled to room temp. and diluted with 50 mL of EtOAc and 20 mL of sat'd. NaHCO$_3$ aq. solution. The organic phase was separated, washed with 20 mL of brine, dried over Na$_2$SO$_4$ and concentrated in vacuo. The residue was purified by a silica gel column chromatography (10% EtOAc/hexane to 50% EtOAc/hexane) to afford light yellow oil as desired product (R)—N-(3-(4-Methoxyphenyl)-4,5-dimethoxybenzyl)-1-phenylethanamine 113 (0.5 g, 42%). MS (ESI, pos. ion) m/z: 378.0 (M+1). $^1$H NMR (400 MHz, CDCl$_3$) δ ppm 10.0-10.2 (br, 2H), 6.8-7.5 (m, 9H), 6.8 (s, 1H); 6.7 (s, 1H), 3.9 (m, 1H); 3.7-3.8 (m, 1H), 3.8 (s, 3H); 3.7 (s, 3H); 3.4 (m, 1H), 3.2 (s, 3H), 1.7 (d, J=7.0 Hz, 3H).

Example 26

Synthesis of (R)—N-(4-Methoxy-3-(pyrrolidin-1-yl)benzyl)-1-(3-fluorophenyl)ethanamine

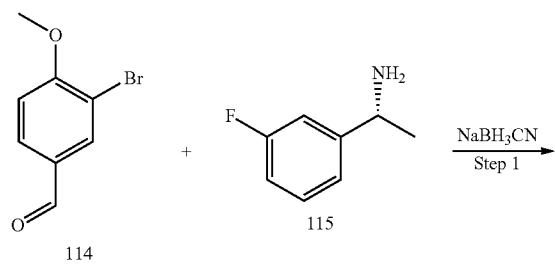

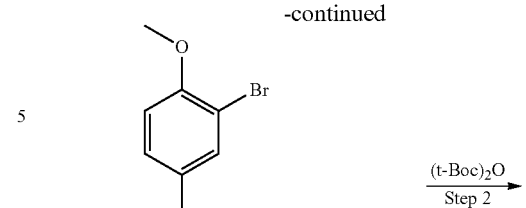

Step 1. (R)-1-(3-Fluorophenyl)ethanamine 115 (1.24 g, 8.92 mmol) and 3-bromo-4-methoxybenzaldehyde 114 (1.92 g, 8.92 mmol) were mixed in 100 mL anhydrous methanol in a round bottom flask. After the mixture was stirred at 20° C. for 10 min, the flask was cooled in an ice-water bath. To this flask was added sodium cyanoborohydride (0.56 g, 8.92 mmol) followed by acetic acid (0.54 g, 8.92 mmol). The resulting mixture was stirred for 12 h and allowed to warm to 20° C. After removing most of the methanol, the remaining residue was dissolved in 200 mL ethyl ether and washed with saturated sodium bicarbonate, 3 times. The organic phase was dried over sodium sulfate. After removing the solvent under reduced pressure, the remaining residue was subjected to a silica gel column using 50% ethylacetate in hexane as the eluant to yield a colorless oil as the pure product (R)—N-(3-bromo-4-methoxybenzyl)-1-(3-fluorophenyl)ethanamine 116 (2.3 g, yield=93%). LCMS (M+1) 338, calc. for $C_{16}H_{17}BrFNO$ 338; $^1$H NMR (400 MHz, CHLOROFORM-d) δ ppm 1.34 (d, J=6.26 Hz, 3H) 3.46-3.60 (m, 2H) 3.78 (q, J=6.39 Hz, 1H) 6.84 (d, J=8.22 Hz, 1H) 6.90-6.98 (m, 1H) 7.09 (t, J=9.00 Hz, 2H) 7.16 (dd, J=8.41, 2.15 Hz, 1H) 7.27-7.34 (m, 1H) 7.48 (d, J=1.96 Hz, 1H).

Step 2. (R)—N-(3-Bromo-4-methoxybenzyl)-1-(3-fluorophenyl)ethanamine 116 (0.502 g, 1.49 mmol) was treated with di-tert-butyl dicarbonate (0.488 g, 2.23 mmol) in 100 ml THF and 20 mL 1 M potassium carbonate for 12 h. The reaction mixture was mixed with 200 mL ethyl ether and washed with brine, 3 times. After removing the solvent, the crude product was purified with a silica gel column with 5% ethylacetate in hexane as the eluant to yield a colorless oil as the pure product (R)-tert-Butyl 3-bromo-4-methoxybenzyl (1-(3-fluorophenyl)ethyl)carbamate 117 (0.65 g, 100%). LCMS (M+1) 438 calc. for $C_{21}H_{25}BrFNO_3$ 438.

Step 3 and 4. (R)-tert-Butyl 3-bromo-4-methoxybenzyl(1-(3-fluorophenyl)ethyl)carbamate 117 (0.108 g, 0.248 mmol), pyrrolidine (0.025 g, 0.347 mmol), tris(dibenzylidineacetone)-dipalladium(0) (0.57 mg, 0.6 mmol), sodium tert-butoxide (35.7 mg, 0.372 mmol) were mixed in a dry microwave heating tube with 1 mL toluene. The mixture was degassed with a stream of nitrogen for 1 min. After BINAP (1.16 mg, 1.86 umol) was added to the tube, the tube was sealed and heated in the Personal Chemistry Microwave Synthesizer® for 20 minutes at 120° C. The reaction mixture was mixed with 20 mL dichloromethane and filtered through a pad of Celite. After removing the solvent under a reduced pressure, the remaining residue was subjected to a silica gel column using 40% ethylacetate in hexane as the eluant to yield a 90% pure product (0.109 g) as a yellow oil. LCMS (M+1) 429 calc. for $C_{25}H_{33}FN_2O_3$ 429. This crude product was stirred with 3 mL 4M HCl in dioxane at 20° C. for 24 h. After removing the solvent, the crude product was purified using a Gilson HPLC to yield the desired product (R)—N-(4-Methoxy-3-(pyrrolidin-1-yl)benzyl)-1-(3-fluorophenyl)ethanamine 118 as a white solid as a TFA salt. LCMS (M+1) 329, calc. for $C_{20}H_{25}FN_2O$ 329; $^1$H NMR (400 MHz, Methanol-$d_4$) δ ppm 1.62 (d, J=6.8 Hz, 3H) 2.10 (bs, 4H) 3.55 (bs, 4H) 3.85 (d, J=13 Hz, 1H) 3.89 (s, 3H), 4.06 (d, J=13 Hz, 1H) 4.39 (q, J=6.8 Hz, 1H) 7.12-7.23 (m, 4H) 7.3 (s, 1H), 7.38-7.43 (m, 2H).

Example 27

Compounds in Table 5 were prepared by using either Method A or Method C described in the general methods section.

TABLE 5

| Comp | structure | name | MW | m/z [M + H+] | Method |
|---|---|---|---|---|---|
| 119 | 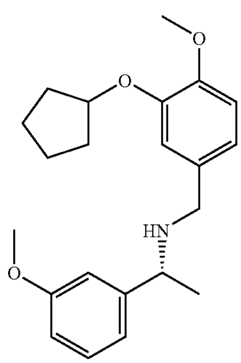 [SMILES: COc1cccc([C@@H](C)NCc2ccc(OC)c(OC3CCCC3)c2)c1] | (3-Cyclopentyloxy-4-methoxy-benzyl)-[(S)-1-(3-methoxy-phenyl)-ethyl]-amine | 355 | 356 | A |
| 120 | 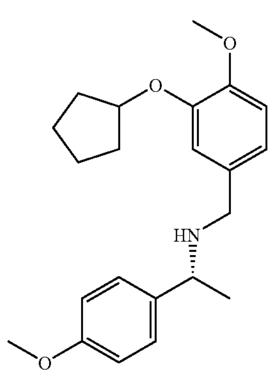 [SMILES: COc1ccc([C@@H](C)NCc2ccc(OC)c(OC3CCCC3)c2)cc1] | (3-Cyclopentyloxy-4-methoxy-benzyl)-[(R)-1-(4-methoxy-phenyl)-ethyl]-amine | 355 | 356 | A |

TABLE 5-continued

| Comp | structure | name | MW | m/z [M + H+] | Method |
|---|---|---|---|---|---|
| 121 | 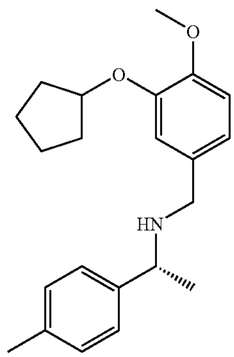 [SMILES: COc1ccc(CN[C@H](C)c2ccc(C)cc2)cc1OC1CCCC1] | (3-Cyclopentyloxy-4-methoxy-benzyl)-((R)-1-p-tolyl-ethyl)-amine | 339 | 340 | A |
| 122 | 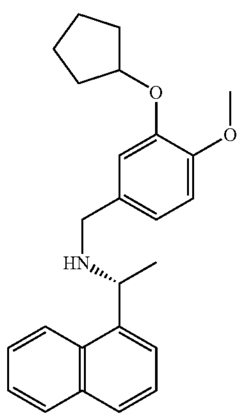 [SMILES: COc1ccc(CN[C@H](C)c2cccc3ccccc23)cc1OC1CCCC1] | (3-Cyclopentyloxy-4-methoxy-benzyl)-((R)-1-naphthalen-1-yl-ethyl)-amine | 375.5 | 376 | A |
| 123 | 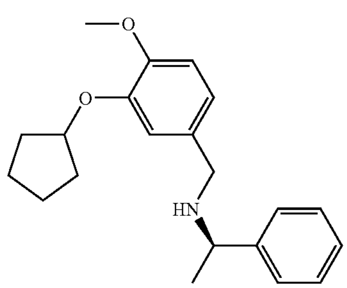 [SMILES: COc1ccc(CN[C@H](C)c2ccccc2)cc1OC1CCCC1] | (3-Cyclopentyloxy-4-methoxy-benzyl)-((R)-1-phenyl-ethyl)-amine | 325 | 326 | A |
| 124 | 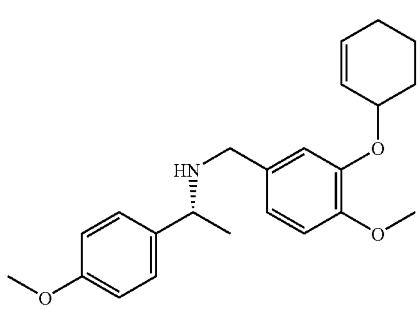 [SMILES: COc1ccc([C@@H](C)NCc2ccc(OC)c(OC3C=CCCC3)c2)cc1] | [3-(Cyclohex-2-enyloxy)-4-methoxy-benzyl]-[(R)-1-(4-methoxy-phenyl)-ethyl]-amine | 367 | 368 | A |

TABLE 5-continued

| Comp | structure | name | MW | m/z [M + H+] | Method |
|---|---|---|---|---|---|
| 125 | 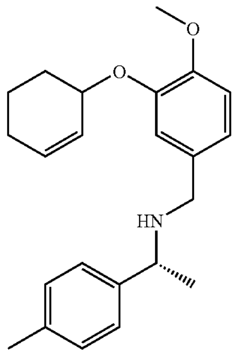 [SMILES: COc1ccc(CN[C@H](C)c2ccc(C)cc2)cc1OC1C=CCCC1] | [3-(Cyclohex-2-enyloxy)-4-methoxy-benzyl]-((R)-1-p-tolyl-ethyl)-amine | 351.5 | 352 | A |
| 126 | 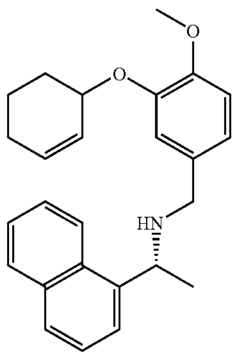 [SMILES: COc1ccc(CN[C@H](C)c2cccc3ccccc23)cc1OC1C=CCCC1] | [3-(Cyclohex-2-enyloxy)-4-methoxy-benzyl]-((R)-1-naphthalen-1-yl-ethyl)-amine | 387.5 | 388 | A |
| 127 | 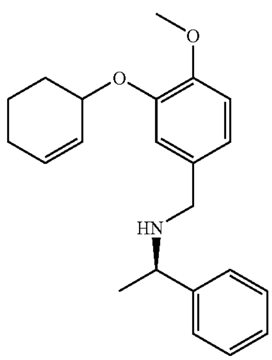 [SMILES: COc1ccc(CN[C@H](C)c2ccccc2)cc1OC1C=CCCC1] | [3-(Cyclohex-2-enyloxy)-4-methoxy-benzyl]-((R)-1-phenyl-ethyl)-amine | 337.5 | 338 | A |
| 128 | 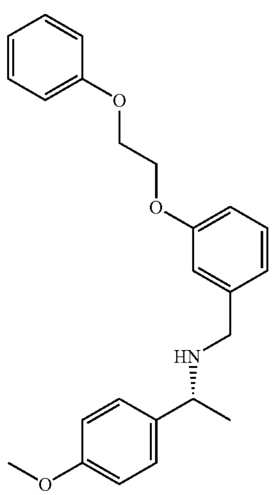 [SMILES: COc1ccc([C@@H](C)NCc2cccc(OCCOc3ccccc3)c2)cc1] | [(R)-1-(4-Methoxy-phenyl)-ethyl]-[3-(2-phenoxy-ethoxy)-benzyl]-amine | 377.5 | 378 | A |

TABLE 5-continued

| Comp | structure | name | MW | m/z [M + H+] | Method |
|---|---|---|---|---|---|
| 129 | 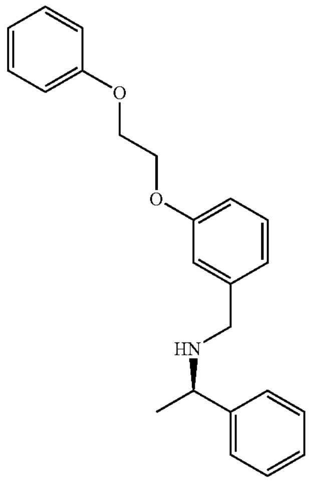 [SMILES: C[C@@H](NCc1cccc(OCCOc2ccccc2)c1)c1ccccc1] | [3-(2-Phenoxy-ethoxy)-benzyl]-((S)-1-phenyl-ethyl)-amine | 347.5 | 348 | A |
| 130 | 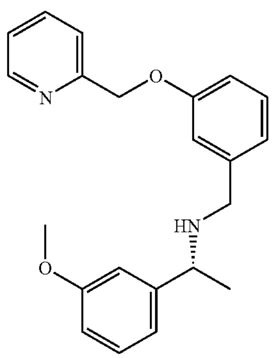 [SMILES: COc1cccc([C@@H](C)NCc2cccc(OCc3ccccn3)c2)c1] | [(S)-1-(3-Methoxy-phenyl)-ethyl]-[3-(pyridin-2-ylmethoxy)-benzyl]-amine | 348.4 | 349 | A |
| 131 | 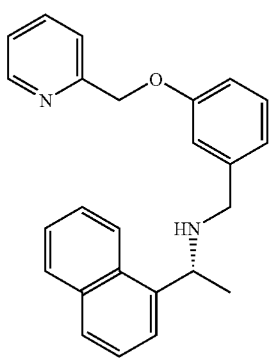 [SMILES: C[C@@H](NCc1cccc(OCc2ccccn2)c1)c1cccc2ccccc12] | ((S)-1-Naphthalen-1-yl-ethyl)-[3-(pyridin-2-ylmethoxy)-benzyl]-amine | 368.5 | 369 | A |
| 132 | 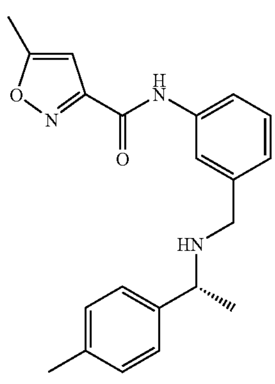 [SMILES: Cc1ccc([C@@H](C)NCc2cccc(NC(=O)c3cc(C)on3)c2)cc1] | 5-Methyl-isoxazole-3-carboxylic acid {3-[((S)-1-p-tolyl-ethylamino)-methyl]-phenyl}-amide | 349.4 | 350 | A |

TABLE 5-continued

| Comp | structure | name | MW | m/z [M + H+] | Method |
|---|---|---|---|---|---|
| 133 | 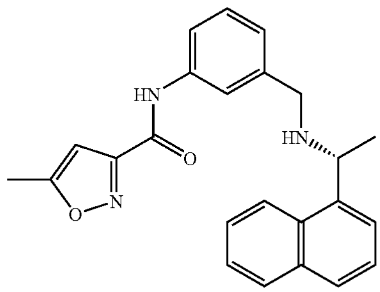 [SMILES: Cc1cc(C(=O)Nc2cccc(CN[C@H](C)c3cccc4ccccc34)c2)no1] | 5-Methyl-isoxazole-3-carboxylic acid {3-[((S)-1-naphthalen-1-yl-ethylamino)-methyl]-phenyl}-amide | 385.5 | 386 | A |
| 134 | 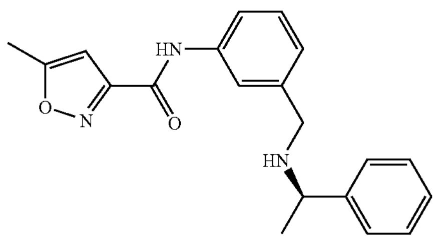 [SMILES: Cc1cc(C(=O)Nc2cccc(CN[C@H](C)c3ccccc3)c2)no1] | 5-Methyl-isoxazole-3-carboxylic acid{3-[((S)-1-phenyl-ethylamino)-methyl]-phenyl}-amide | 335.4 | 336 | A |
| 135 | 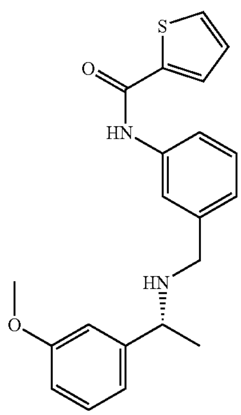 [SMILES: COc1cccc([C@@H](C)NCc2cccc(NC(=O)c3cccs3)c2)c1] | Thiophene-2-carboxylic acid (3-{[(S)-1-(3-methoxy-phenyl)-ethylamino]-methyl}-phenyl)-amide | 366.5 | 367 | A |
| 136 | 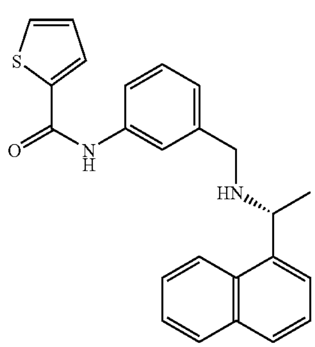 [SMILES: C[C@@H](NCc1cccc(NC(=O)c2cccs2)c1)c1cccc2ccccc12] | Thiophene-2-carboxylic acid {3-[((S)-1-naphthalen-1-yl-ethylamino)-methyl]-phenyl}-amide | 386.5 | 387 | A |

TABLE 5-continued

| Comp | structure | name | MW | m/z [M + H+] | Method |
|---|---|---|---|---|---|
| 137 | 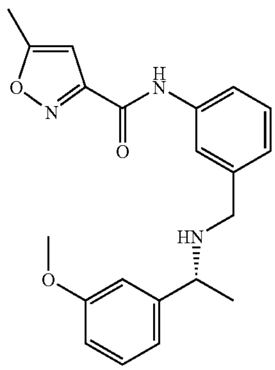 [SMILES: COc1cccc([C@@H](C)NCc2cccc(NC(=O)c3cc(C)on3)c2)c1] | 5-Methyl-isoxazole-3-carboxylic acid (3-{[(S)-1-(3-methoxy-phenyl)-ethylamino]-methyl}-phenyl)-amide | 365.4 | 366 | A |
| 138 | 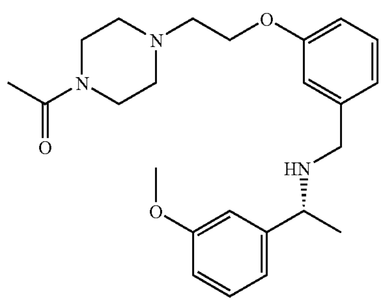 [SMILES: COc1cccc([C@@H](C)NCc2cccc(OCCN3CCN(C(C)=O)CC3)c2)c1] | 1-{4-[2-(3-{[(S)-1-(3-Methoxy-phenyl)-ethylamino]-methyl}-phenoxy)-ethyl]-piperazin-1-yl}-ethanone | 411.5 | 412 | A |
| 139 | 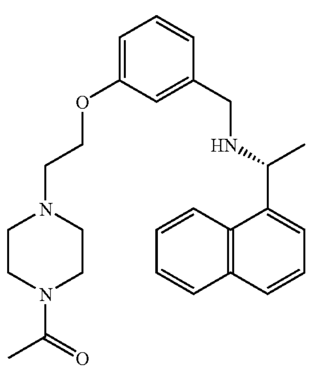 [SMILES: CC(=O)N1CCN(CCOc2cccc(CN[C@H](C)c3cccc4ccccc34)c2)CC1] | 1-[4-(2-{3-[((S)-1-Naphthalen-1-yl-ethylamino)-methyl]-phenoxy}-ethyl)-piperazin-1-yl]-ethanone | 431.6 | 432 | A |
| 140 | 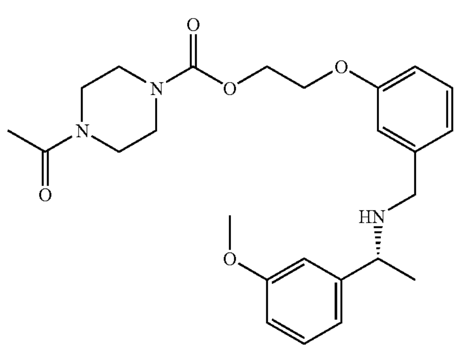 [SMILES: COc1cccc([C@@H](C)NCc2cccc(OCCOC(=O)N3CCN(C(C)=O)CC3)c2)c1] | 4-Acetyl-piperazine-1-carboxylic acid 2-(3-{[(S)-1-(3-methoxy-phenyl)-ethylamino]-methyl}-phenoxy)-ethyl ester | 455.6 | 456 | A |

TABLE 5-continued

| Comp | structure | name | MW | m/z [M + H+] | Method |
|---|---|---|---|---|---|
| 141 | 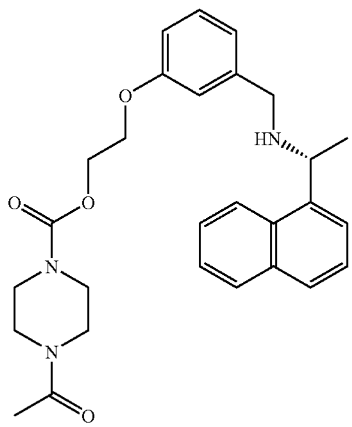 [SMILES: CC(=O)N1CCN(C(=O)OCCOc2cccc(CN[C@H](C)c3cccc4ccccc34)c2)CC1] | 4-Acetyl-piperazine-1-carboxylic acid 2-{3-[((S)-1-naphthalen-1-yl-ethylamino)-methyl]-phenoxy}-ethyl ester | 475.6 | 476 | A |
| 142 | 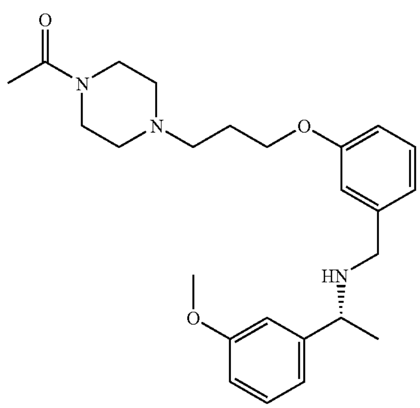 [SMILES: COc1cccc([C@@H](C)NCc2cccc(OCCCN3CCN(C(C)=O)CC3)c2)c1] | 1-{4-[3-(3-{[(S)-1-(3-Methoxy-phenyl)-ethylamino]-methyl}-phenoxy)-propyl]-piperazin-1-yl}-ethanone | 425.6 | 426 | A |
| 143 | 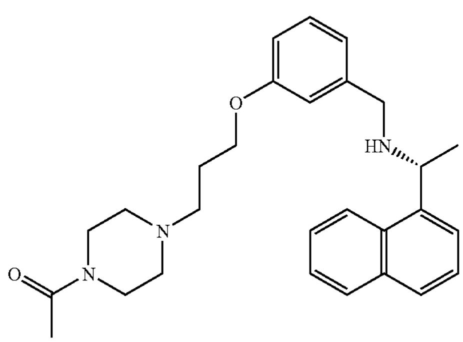 [SMILES: CC(=O)N1CCN(CCCOc2cccc(CN[C@H](C)c3cccc4ccccc34)c2)CC1] | 1-[4-(3-{3-[((S)-1-Naphthalen-1-yl-ethylamino)-methyl]-phenoxy}-propyl)-piperazin-1-yl]-ethanone | 445.6 | 446 | A |
| 144 | 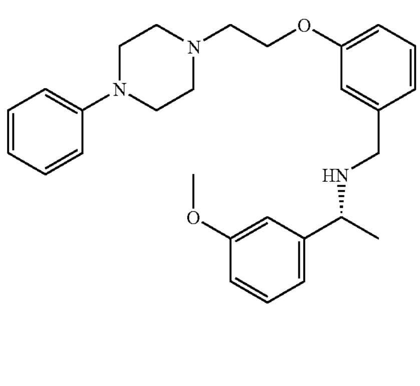 [SMILES: COc1cccc([C@@H](C)NCc2cccc(OCCN3CCN(c4ccccc4)CC3)c2)c1] | [(S)-1-(3-Methoxy-phenyl)-ethyl]-{3-[2-(4-phenyl-piperazin-1-yl)-ethoxy]-benzyl}-amine | 445.6 | 446 | A |

TABLE 5-continued

| Comp | structure | name | MW | m/z [M + H+] | Method |
|---|---|---|---|---|---|
| 145 | 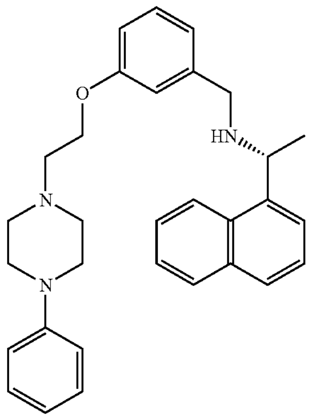 [SMILES: C[C@@H](NCc1cccc(OCCN2CCN(c3ccccc3)CC2)c1)c1cccc2ccccc12] | ((S)-1-Naphthalen-1-yl-ethyl)-{3-[2-(4-phenyl-piperazin-1-yl)-ethoxy]-benzyl}-amine | 465.6 | 466 | A |
| 146 | 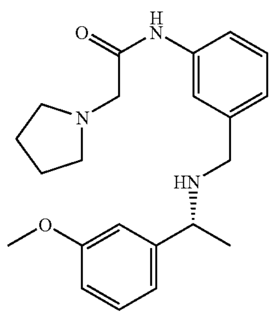 [SMILES: COc1cccc([C@@H](C)NCc2cccc(NC(=O)CN3CCCC3)c2)c1] | N-(3-{[(S)-1-(3-Methoxy-phenyl)-ethylamino]-methyl}-phenyl)-2-pyrrolidin-1-yl-acetamide | 367.5 | 368 | A |
| 147 | 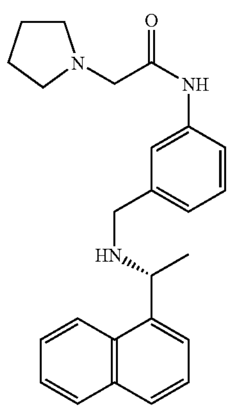 [SMILES: C[C@@H](NCc1cccc(NC(=O)CN2CCCC2)c1)c1cccc2ccccc12] | N-{3-[((S)-1-Naphthalen-1-yl-ethylamino)-methyl]-phenyl}-2-pyrrolidin-1-yl-acetamide | 387.5 | 388 | A |
| 148 | 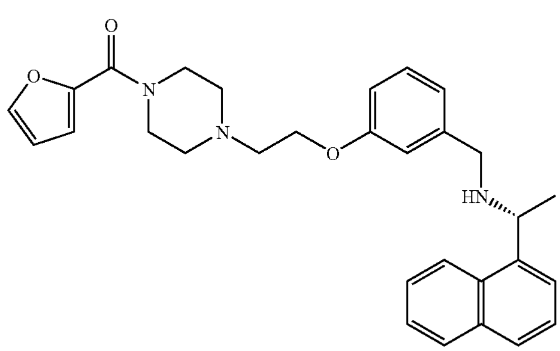 [SMILES: C[C@@H](NCc1cccc(OCCN2CCN(C(=O)c3ccco3)CC2)c1)c1cccc2ccccc12] | Furan-2-yl-[4-(2-{3-[((S)-1-naphthalen-1-yl-ethylamino)-methyl]-phenoxy}-ethyl)-piperazin-1-yl]-methanone | 483.6 | 484 | A |

TABLE 5-continued

| Comp | structure | name | MW | m/z [M + H+] | Method |
|---|---|---|---|---|---|
| 149 | 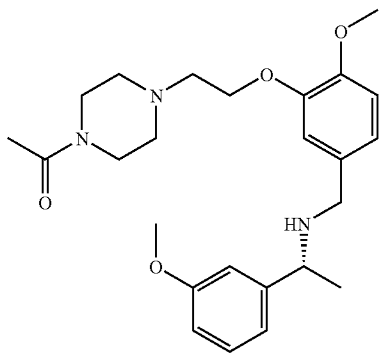 [SMILES: COc1cccc([C@@H](C)NCc2ccc(OC)c(OCCN3CCN(C(C)=O)CC3)c2)c1] | 1-{4-[2-(2-Methoxy-5-{[(S)-1-(3-methoxy-phenyl)-ethylamino]-methyl}-phenoxy)-ethyl]-piperazin-1-yl}-ethanone | 441.6 | 442 | A |
| 150 | 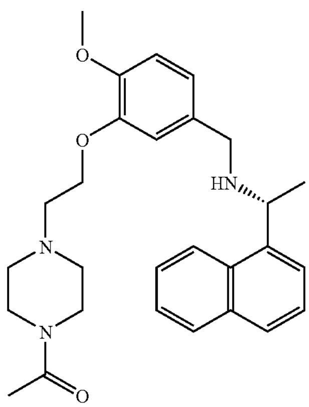 [SMILES: COc1ccc(CN[C@H](C)c2cccc3ccccc23)cc1OCCN1CCN(C(C)=O)CC1] | 1-[4-(2-{2-Methoxy-5-[((R)-1-naphthalen-1-yl-ethylamino)-methyl]-phenoxy}-ethyl)-piperazin-1-yl]-ethanone | 461.6 | 462 | A |
| 151 | 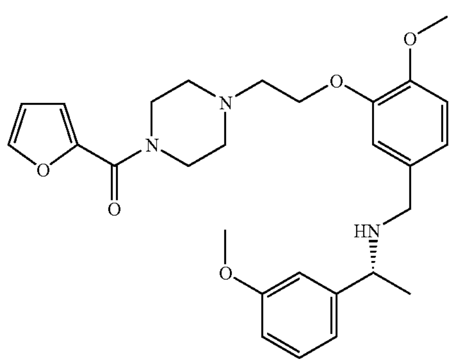 [SMILES: COc1cccc([C@@H](C)NCc2ccc(OC)c(OCCN3CCN(C(=O)c4ccco4)CC3)c2)c1] | Furan-2-yl-{4-[2-(2-methoxy-5-{[(S)-1-(3-methoxy-phenyl)-ethylamino]-methyl}-phenoxy)-ethyl]-piperazin-1-yl}-methanone | 493.6 | 494 | A |
| 152 | 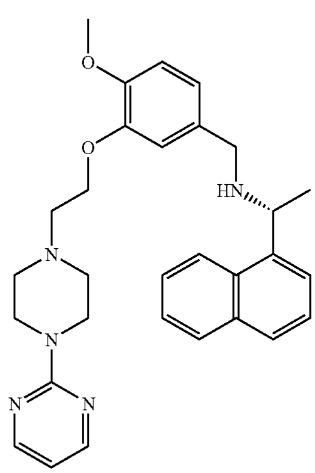 [SMILES: COc1ccc(CN[C@H](C)c2cccc3ccccc23)cc1OCCN1CCN(c2ncccn2)CC1] | {4-Methoxy-3-[2-(4-pyrimidin-2-yl-piperazin-1-yl)-ethoxy]-benzyl}-((R)-1-naphthalen-1-yl-ethyl)-amine | 497.6 | 498 | A |

TABLE 5-continued

| Comp | structure | name | MW | m/z [M + H+] | Method |
|------|-----------|------|-----|--------------|--------|
| 153 | 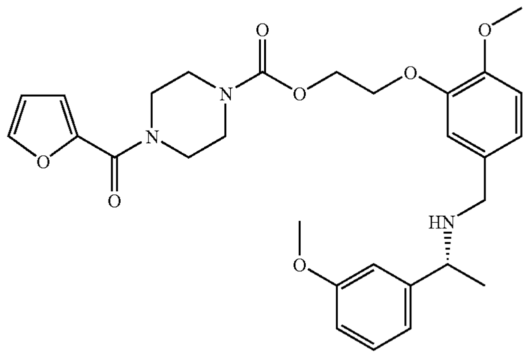 [SMILES: COc1cccc([C@@H](C)NCc2ccc(OC)c(OCCOC(=O)N3CCN(C(=O)c4ccco4)CC3)c2)c1] | 4-(Furan-2-carbonyl)-piperazine-1-carboxylic acid 2-(2-methoxy-5-{[(S)-1-(3-methoxy-phenyl)-ethylamino]-methyl}-phenoxy)-ethyl ester | 537.6 | 538 | A |
| 154 | 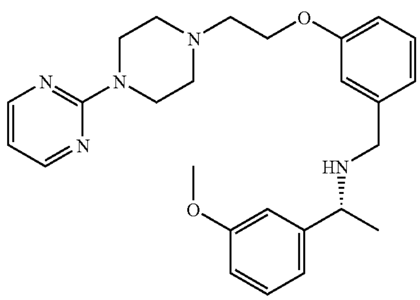 [SMILES: COc1cccc([C@@H](C)NCc2cccc(OCCN3CCN(c4ncccn4)CC3)c2)c1] | [(S)-1-(3-Methoxy-phenyl)-ethyl]-{3-[2-(4-pyrimidin-2-yl-piperazin-1-yl)-ethoxy]-benzyl}-amine | 447.6 | 448 | A |
| 155 | 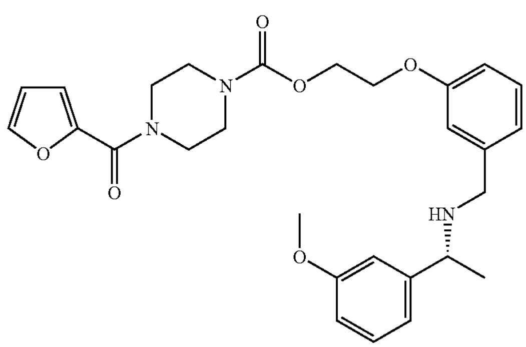 [SMILES: COc1cccc([C@@H](C)NCc2cccc(OCCOC(=O)N3CCN(C(=O)c4ccco4)CC3)c2)c1] | 4-(Furan-2-carbonyl)-piperazine-1-carboxylic acid 2-(3-{[(S)-1-(3-methoxy-phenyl)-ethylamino]-methyl}-phenoxy)-ethyl ester | 507.6 | 508 | A |
| 156 | 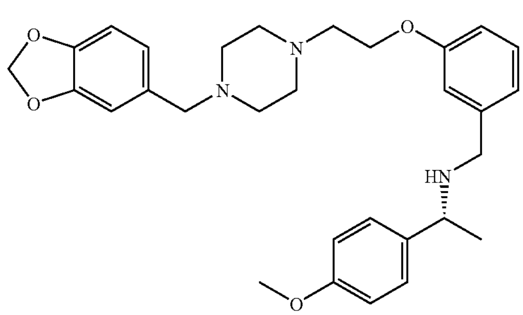 [SMILES: COc1ccc([C@@H](C)NCc2cccc(OCCN3CCN(Cc4ccc5c(c4)OCO5)CC3)c2)cc1] | {3-[2-(4-Benzo[1,3]dioxol-5-ylmethyl-piperazin-1-yl)-ethoxy]-benzyl}-[(R)-1-(4-methoxy-phenyl)-ethyl]-amine | 503.6 | 504 | A |

TABLE 5-continued

| Comp | structure | name | MW | m/z [M + H+] | Method |
|---|---|---|---|---|---|
| 157 | 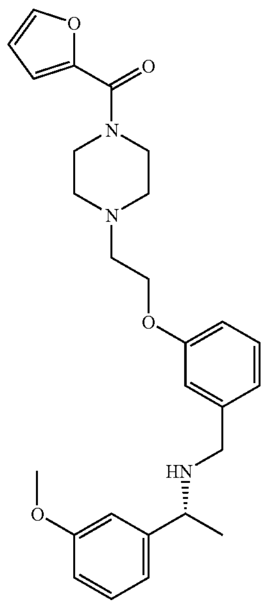 [SMILES: COc1cccc([C@@H](C)NCc2cccc(OCCN3CCN(C(=O)c4ccco4)CC3)c2)c1] | Furan-2-yl-{4-[2-(3-{[(S)-1-(3-methoxy-phenyl)-ethylamino]-methyl}-phenoxy)-ethyl]-piperazin-1-yl}-methanone | 463.6 | 464 | A |
| 158 | 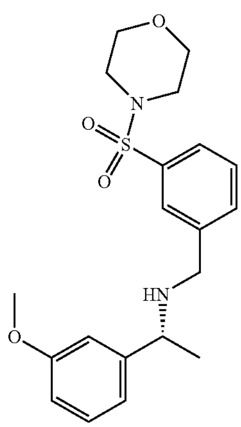 [SMILES: COc1cccc([C@@H](C)NCc2cccc(S(=O)(=O)N3CCOCC3)c2)c1] | [(S)-1-(3-Methoxy-phenyl)-ethyl]-[3-(morpholine-4-sulfonyl)-benzyl]-amine | 390.5 | 391 | C |
| 159 | 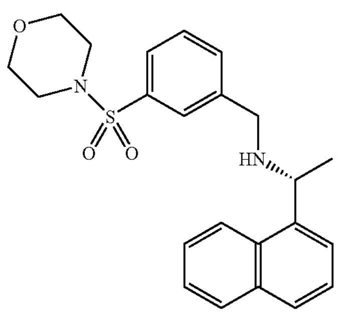 [SMILES: C[C@@H](NCc1cccc(S(=O)(=O)N2CCOCC2)c1)c1cccc2ccccc12] | [3-(Morpholine-4-sulfonyl)-benzyl]-((S)-1-naphthalen-1-yl-ethyl)-amine | 410.5 | 411 | C |

TABLE 5-continued

| Comp | structure | name | MW | m/z [M + H+] | Method |
|---|---|---|---|---|---|
| 160 | 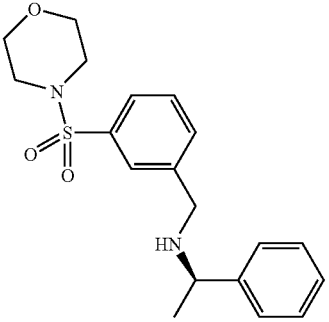 [SMILES: C[C@@H](NCc1cccc(S(=O)(=O)N2CCOCC2)c1)c1ccccc1] | [3-(Morpholine-4-sulfonyl)-benzyl]-((S)-1-phenyl-ethyl)-amine | 360.5 | 361 | C |
| 161 | 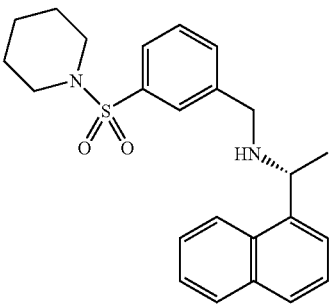 [SMILES: C[C@@H](NCc1cccc(S(=O)(=O)N2CCCCC2)c1)c1cccc2ccccc12] | ((S)-1-Naphthalen-1-yl-ethyl)-[3-(piperidine-1-sulfonyl)-benzyl]-amine | 408.6 | 409 | C |
| 162 | 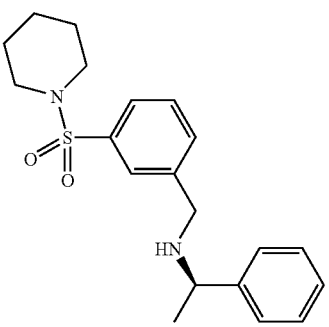 [SMILES: C[C@@H](NCc1cccc(S(=O)(=O)N2CCCCC2)c1)c1ccccc1] | ((S)-1-Phenyl-ethyl)-[3-(piperidine-1-sulfonyl)-benzyl]-amine | 358.50 | 359 | C |
| 163 | 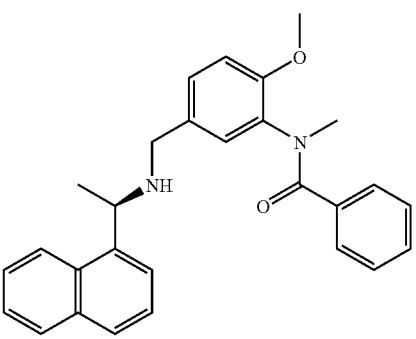 [SMILES: COc1ccc(CN[C@H](C)c2cccc3ccccc23)cc1N(C)C(=O)c1ccccc1] | N-{2-Methoxy-5-[((R)-1-naphthalen-1-yl-ethylamino)-methyl]-phenyl}-N-methyl-benzamide | 424.5 | 425 | C |

Example 28

Biological Activity

The activities of the compounds of the present invention on calcium receptors were measured. In one aspect, the measurement was performed in accordance with the method described in Example 4 of International Publication No. WO 96/12697.

A 4.0-kb NotI-HindIII fragment of the human parathyroid cell $Ca^{2+}$ receptor (hPCaR) cDNA was subcloned into the mammalian expression vector pCEP4 (Invitrogen) containing the hygromycin-resistant gene as a selectable marker. This plasmid was transfected into HEK 293 cells by calcium phosphate precipitation. Transfected cells were grown in Dulbecco's modified Eagle's medium containing 10% fetal bovine serum and hygromycin (200 g/mL). Hygromycin-resistant colonies were subcloned and assayed for hPCaR mRNA by solution hybridization using a $^{32}P$-labeled RNA probe complementary to the (4.0 kb) hPCaR sequence (Garrett, et al., J. Biol. Chem. 270, 12919-12925 (1995)). Clone 7 was used to assess the effects of compounds on [Ca$^{2+}$]$_i$. This stably transfected cell line is termed HEK 293 4.0-7. For measurements of [Ca$^{2+}$]$_i$, the cells were recovered from tissue culture flasks by brief treatment with Versene (Invitrogen; containing 0.2 g/L EDTA.4Na in phosphate-buffered saline) and then seeded in collagen coated 384-well plates (BD Biosciences) at 20K cells per well in the growth media (same as above). Cells were grown in 37° C. TC incubator overnight. Then, the media was discarded and cells were loaded with 1× dye from Ca2+ Assay Kit I (BD Biosciences) in parathyroid cell buffer (126 mM NaCl, 4 mM KCl, 1 mM MgSO$_4$, 0.7 mM K$_2$HPO$_4$/KH$_2$PO$_4$, 20 mM HEPES.NaOH (pH 7.45)) containing 0.5% BSA and 1 mM CaCl$_2$. Cells were loaded at room temperature for 90 minutes. Each test compound was added to the cells and the fluorescence was recorded by using excitation and emission wavelengths of 485 and 530 nm, respectively.

The compounds of the invention were tested according to the procedure described above and found to have an EC$_{50}$ of 10 μM or less.

In Vivo Measurements

Male Sprague-Dawley rats weighing 250-400 g were given free access to food and water. Unanesthetized rats were gavaged with an 18-gauge balled needle at a volume between 0.5 and 1 ml. Compounds were formulated in 20% captisol in water at pH 7.0 or 2% hydroxypropyl methylcellulose (HPMC)/1% Tween 80/5% Captisol in water pH 2.0. Calcimimetics were administered at various doses covering the following range 0.03-30 mg/kg in 20% captisol. Vehicle-treated rats received one of the above two vehicles at the maximum volume (0.5-1 ml) used for the calcimimetics. Each rat was bled at time 0 (pre-calcimimetic or vehicle administration) and at various times (1, 2, 4, 8 and 24 h) after oral gavage of calcimimetic or vehicle.

For measurements of blood-ionized Ca$^{2+}$ levels, blood (50 μl) was collected from the orbital sinus of anesthetized rats (3% isoflurane in O$_2$) with heparinized capillary tubes. Blood samples were analyzed within seconds of collection using a Rapidlab 348 Blood Gas Analyzer (Bayer HealthCare LLC Diagnostic Division; Tarrytown, N.Y.).

For measurements of serum PTH, phosphorus, a nonheparinized capillary tube was inserted into the orbital sinus and blood (0.5 ml) was collected into SST (clot activator) brand blood tubes. Blood samples were allowed to clot for 15-30 min and centrifuged (3000 rpm; Sorvall RT 600B) at 4° C. Serum was removed and stored below 0° C. until assayed. Serum PTH levels were quantified according to the vendor's instructions using rat PTH immunoradiometric assay kits (Immutopics, San Clemente, Calif.) or rat bioactive intact PTH elisa kit (Immutopics, San Clemente, Calif.). Serum phosphorus levels were determined using a blood chemistry analyzer (AU 400; Olympus, Melville, N.Y.).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound of Formula I

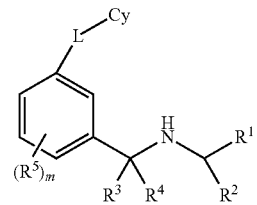

or a pharmaceutically acceptable salt thereof, wherein:
R$^1$ is phenyl, substituted by 0, 1, 2 or 3 substituents selected from C$_{1-6}$alkyl, halogen, C$_{1-4}$haloalkyl, —OC$_{1-6}$alkyl, cyano and nitro;
R$^2$ is C$_{1-8}$alkyl or C$_{1-4}$haloalkyl;
R$^3$ is H, C$_{1-4}$haloalkyl or C$_{1-8}$alkyl;
R$^4$ is H, C$_{1-4}$haloalkyl or C$_{1-8}$alkyl;
R$^5$ is, independently, in each instance, H, C$_{1-8}$ alkyl, C$_{1-4}$haloalkyl, halogen, —OC$_{1-6}$alkyl, —NR$^a$R$^d$, NR$^a$C(=O)R$^d$, substituted or unsubstituted pyrrolidinyl, substituted or unsubstituted azetidinyl, or substituted or unsubstituted piperidyl, wherein the substituents can be selected from halogen, —OR$^b$, —NR$^a$R$^d$, —C(=O)OR$^c$, —C(=O)NR$^a$R$^d$, —OC(=O)R$^c$, —NR$^a$C(=O)R$^c$, cyano, nitro, —NR$^a$(=O)$_n$R$^c$ or —S(=O)$_n$NR$^a$R$^d$;
L is NHC(=O);
Cy is a partially or fully saturated or unsaturated 5-6 membered monocyclic ring system, the ring system formed of carbon atoms optionally including 1-3 heteroatoms and wherein the ring system is optionally substituted independently with one or more substituents of R$^6$, C$_{1-8}$alkyl, C$_{1-4}$haloalkyl, halogen, cyano, nitro, —OC$_{1-6}$alkyl, —NR$^a$R$^d$, NR$^a$C(=O)R$^d$, —C(=O)OR$^c$, —C(=O)NR$^a$R$^d$, —OC(=O)R$^c$, —NR$^a$C(=O)R$^c$, —NR$^a$S(=O)$_m$R$^c$ or —S(=O)$_m$NR$^a$R$^d$;
R$^6$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of C$_{1-8}$alkyl, C$_{1-4}$haloalkyl, halogen, cyano, nitro, —OC$_{1-6}$alkyl, —NR$^a$R$^d$, NR$^a$C(=O)R$^d$, —C(=O)OR$^c$, —C(=O)NR$^a$R$^d$, —OC(=O)R$^c$, —NR$^a$C(=O)R$^c$, —NR$^a$S(=O)$_m$R$^c$ or —S(=O)$_m$NR$^a$R$^d$;
R$^a$ is, independently, at each instance, H, C$_{1-4}$haloalkyl, C$_{1-6}$alkyl, C$_{1-6}$alkenyl, C$_{1-6}$alkylaryl or arylC$_{1-6}$alkyl,
R$^b$ is, independently, at each instance, C$_{1-8}$alkyl, C$_{1-4}$haloalkyl, phenyl, benzyl, naphthyl or a saturated or unsaturated 5- or 6-membered heterocyclic ring containing 1, 2 or 3 atoms selected from N, O and S, with no more than 2 of the atoms selected from O and S, wherein the phenyl, benzyl, naphthyl or the heterocyclic ring are substituted by 0, 1, 2 or 3 substituents selected from C$_{1-6}$alkyl, halogen, C$_{1-4}$haloalkyl, —OC$_{1-6}$alkyl, cyano and nitro;
R$^c$ is, independently, at each instance, C$_{1-6}$alkyl, C$_{1-4}$haloalkyl, phenyl or benzyl;
R$^d$ is, independently, at each instance, C$_{1-6}$alkyl, C$_{1-6}$alkenyl, phenyl, benzyl, naphthyl or a saturated or unsaturated 5- or 6-membered heterocycle ring containing 1, 2 or 3 atoms selected from N, O and S, with no more than 2 of the atoms selected from O and S, wherein the C$_{1-6}$alkyl, phenyl, benzyl, naphthyl and the heterocycle ring are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —$C(=O)R^c$, —$OR^b$, —$NR^aR^b$, —$C(=O)OR^c$, —$C(=O)NR^aR^b$, —$OC(=O)R^c$, —$NR^aC(=O)R^c$, —$NR^aS(=O)_mR^c$ and —$S(=O)_mNR^aR^a$;

m is 1 or 2;

n is 1 or 2.

2. The compound of claim 1 or a pharmaceutically acceptable salt thereof, wherein $R^5$ is H.

3. The compound of claim 1 or a pharmaceutically acceptable salt thereof, wherein $R^5$ is halogen.

4. The compound of claim 2 or a pharmaceutically acceptable salt thereof, wherein halogen is Cl.

5. The compound of claim 1 or a pharmaceutically acceptable salt thereof wherein $R^5$ is methoxy.

6. The compound of claim 1 or a pharmaceutically acceptable salt thereof, wherein $R^5$ is substituted or unsubstituted piperidyl, wherein the substituents can be selected from halogen, —$OR^b$, —$NR^aR^d$, —$C(=O)OR^c$, —$C(=O)NR^aR^d$, —$OC(=O)R^c$, —$NR^aC(=O)R^c$, cyano, nitro, —$NR^aS(=O)_nR^c$ or —$S(=O)_nNR^aR^d$.

7. The compound of claim 1 or a pharmaceutically acceptable salt thereof, wherein Cy is optionally substituted aryl or heteroaryl.

8. A compound or a pharmaceutically acceptable salt thereof, wherein the compound is selected from the group consisting of:

(R)—N-(2-Chloro-5-((1-(3-chlorophenyl)ethylamino)methyl)phenyl)-5-methylisoxazole-3-carboxamide;

N-(2-chloro-5-(((((1R)-1-phenylethyl)amino)methyl)phenyl)acetamide;

N-(2-chloro-5-((((1R)-1-phenylethyl)amino)methyl)phenyl)-2-furancarboxamide;

N-(2-chloro-5-((((1R)-1-phenylethyl)amino)methyl)phenyl) 1,3-dimethyl-1H-pyrazole-5-carboxamide;

N-(2-chloro-5-((((1R)-1-phenylethyl)amino)methyl)phenyl)-3-phenylpropanamide,

N-(2-chloro-5-((((1R)-1-phenylethyl)amino)methyl)phenyl)benzamide;

N-(2-chloro-5-(((((R)-1-phenylethyl)amino)methyl)phenyl)-2-thiophenecarboxamide;

N-(2-chloro-5-((((1R)-1-phenylethyl)amino)methyl)phenyl)-5-isoxazolecarboxamide;

N-(2-chloro-5-((((1R)-1-phenylethyl)amino)methyl)phenyl)-5-methyl-3-isoxazolecarboxamide;

N-(2-chloro-5-((((1R)-1-phenylethyl)amino)methyl)phenyl)-2-pyridinecarboxamide;

N-(2-chloro-5-((((1R)-1-phenylethyl)amino)methyl)phenyl)-3-pyridinecarboxamide;

N-(2-chloro-5-((((1R)-1-phenylethyl)amino)methyl)phenyl)-4-pyridinecarboxamide;

N-(2-chloro-5-((((1R)-1-phenylethyl)amino)methyl)phenyl)-2,5-dimethyl-1,3-oxazole-4-carboxamide;

N-(2-chloro-5-(((((1R)-1-phenylethyl)amino)methyl)phenyl)-4-methyl-1,2,3-thiadiazole-5-carboxamide;

N-(2-chloro-5-((((1R)-1-phenylethyl)amino)methyl)phenyl)-5-(2-methyl-1,3-thiazol-4-yl)-3-isoxazolecarboxamide;

N-(2-chloro-5-((((1R)-1-phenylethyl)amino)methyl)phenyl)-1-(1,1-dimethylethyl)-5-methyl-1H-pyrazole-3-carboxamide;

N-(2-chloro-5-((((1R)-1-phenylethyl)amino)methyl)phenyl)-5-phenyl-3-isoxazolecarboxamide;

6-chloro-N-(2-chloro-5-((((1R)-1-phenylethyl)amino)methyl)phenyl)-3-pyridinecarboxamide;

N-(2-chloro-5-((((1R)-1-phenylethyl)amino)methyl)phenyl)-3-thiophenecarboxamide;

N-(2-chloro-5-((((1R)-1-phenylethyl)amino)methyl)phenyl)-5-(2-pyridinyl)-2-thiophenecarboxamide;

N-(2-chloro-5-((((1R)-1-phenylethyl)amino)methyl)phenyl)-5-phenyl-2-thiophenecarboxamide;

N-(2-chloro-5-((((1R)-1-(1-naphthalenyl)ethyl)amino)methyl)phenyl)-2-pyridinecarboxamide;

(R)—N-(2-Chloro-5-((1-phenylethylamino)methyl)phenyl)-2-(pyrrolidin-1-yl)acetamide;

(R)—N-(2-chloro-5-((1-phenylethylamino)methyl)phenyl)-6-(dimethylamino)nicotinamide;

N-(2-chloro-5-((((1R)-1-phenylethyl)amino)methyl)phenyl)-6-(4-morpholinyl)-3-pyridinecarboxamide;

N-(2-chloro-5-((((1R)-1-phenylethyl)amino)methyl)phenyl)-6-(4-methyl-1-piperazinyl)-3-pyridinecarboxamide;

N-(2-chloro-5-((((1R)-1-phenylethyl)amino)methyl)phenyl)-6-((2-(dimethylamino)ethyl)amino)-3-pyridinecarboxamide;

N-(2-chloro-5-((((1R)-1-phenylethyl)amino)methyl)phenyl)-6-(methylamino)-3-pyridinecarboxamide;

N-(2-chloro-5-((((1R)-1-phenylethyl)amino)methyl)phenyl)-6-(phenylamino)-3-pyridinecarboxamide;

N-(2-chloro-5-((((1R)-1-phenyl)ethyl)amino)methyl)phenyl)-6-((phenylmethyl)amino)-3-pyridinecarboxamide;

N-(2-chloro-5-((((1R)-1-phenylethyl)amino)methyl)phenyl)-6-((2-phenylethyl)amino)-3-pyridinecarboxamide;

(R)-1-(2-(5-methylisoxazole-3-carboxamido)-4-((1-phenylethylamino)methyl)phenyl)piperidine-4-carboxamide;

(R)-2-Chloro-5-((1-phenylethylamino)methyl)-N-(pyridin-2-ylmethyl)benzenamine;

(1R)—N-(3-(1H-Benzo[d]imidazol-1-yl)-4-chlorobenzyl)-1-phenylethanamine;

(1R)—N-(4-chloro-3-(1H-1,2,4-triazol-1-yl)benzyl)-1-phenylethanamine;

N-(2-Chloro-5-(1-((R)-1-(3-chlorophenyl)ethylamino)ethyl)phenyl)-5-methylisoxazole-3-carboxamide;

(R)—N-(4-Methoxy-3-(pyrrolidin-1-yl)benzyl)-1-(3-fluorophenyl)ethanamine;

5-Methyl-isoxazole-3-carboxylic acid {3-[((S)-1-p-tolyl-ethylamino)-methyl]-phenyl}-amide;

5-Methyl-isoxazole-3-carboxylic acid {3-[((S)-1-naphthalen-1-yl-ethylamino)-methyl]-phenyl}-amide;

5-Methyl-isoxazole-3-carboxylic acid {3-[((S)-1-phenyl-ethylamino)-methyl]-phenyl}-amide;

Thiophene-2-carboxylic acid (3-{[(S)-1-(3-methoxy-phenyl)-ethylamino]-methyl}-phenyl)-amide;

Thiophene-2-carboxylic acid {3-[((S)-1-naphthalen-1-yl-ethylamino)-methyl]-phenyl}-amide;

5-Methyl-isoxazole-3-carboxylic acid (3-{[(S)-1-(3-methoxy-phenyl)-ethylamino]-methyl}-phenyl)-amide;

N-(3-{[(S)-1-(3-Methoxy-phenyl)-ethylamino]-methyl}-phenyl)-2-pyrrolidin-1-yl-acetamide;

N-{3-[((S)-1-Naphthalen-1-yl-ethylamino)-methyl]-phenyl}-2-pyrrolidin-1-yl-acetamide; and N-{2-Methoxy-5-[((R)-1-naphthalen-1-yl-ethylamino)-methyl]-phenyl}-N-methyl-benzamide.

9. A pharmaceutical composition comprising a compound of claim 8 or a pharmaceutically acceptable salt thereof and a pharmaceutically acceptable diluent or carrier.

10. The compound of claim 1 or a pharmaceutically acceptable salt thereof, wherein Cy is pyridine.

* * * * *